US005795762A

United States Patent [19]

Abramson et al.

[11] Patent Number: 5,795,762

[45] **Date of Patent: *Aug. 18, 1998**

[54] 5' TO 3' EXONUCLEASE MUTATIONS OF THERMOSTABLE DNA POLYMERASES

[75] Inventors: Richard D. Abramson; David H. Gelfand, both of Oakland, Calif.

[73] Assignee: Roche Molecular Systems, Inc., Branchburg, N.J.

[ * ] Notice: The term of this patent shall not extend beyond the expiration date of Pat. Nos. 5,405,774 and 5,455,170.

[21] Appl. No.: 458,819

[22] Filed: Jun. 2, 1995

Related U.S. Application Data

[63] Continuation of Ser. No. 977,434, Feb. 23, 1993, Pat. No. 5,466,591, which is a continuation-in-part of Ser. No. 746,121, Aug. 15, 1991, Pat. No. 5,310,652, Ser. No. 590,213, Sep. 28, 1990, abandoned, Ser. No. 590,466, Sep. 28, 1990, Pat. No. 5,455,170, and Ser. No. 590,490, Sep. 28, 1990, abandoned, said Ser. No. 590,213, Ser. No. 590,466, and Ser. No. 590,499, each is a continuation-in-part of Ser. No.523,394, May 15, 1990, Pat. No. 5,079,352, which is a continuation-in-part of Ser. No. 143,441, Jan. 12, 1988, Pat. No. 4,889,818, which is a continuation-in-part of Ser. No. 899,241, Aug. 22, 1986, said Ser. No. 746,121, is a continuation-in-part of Ser. No. 585,471, Sep. 20, 1990, abandoned, which is a continuation-in-part of Ser. No. 455,611, Dec. 22, 1989, Pat. No. 5,322,770, which is a continuation-in-part of Ser. No. 143,441, Jan. 12, 1988, said Ser. No. 746,121, is a continuation-in-part of Ser. No. 609,157, Nov. 2, 1990, abandoned, which is a continuation-in-part of Ser. No. 557,517, Jul. 24, 1990, abandoned.

[51] Int. Cl.$^6$ ..................... C12N 9/12

[52] U.S. Cl. ..................... 435/194

[58] Field of Search ..................... 435/194

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 5,079,352 | 1/1992 | Gelfand et al. | 536/27 |
| 5,108,892 | 4/1992 | Burke et al. | 435/6 |
| 5,210,015 | 5/1993 | Gelfand et al. | 435/6 |

FOREIGN PATENT DOCUMENTS

| | | |
|---|---|---|
| 0258017 | 3/1988 | European Pat. Off. . |
| 9109944 | 7/1991 | WIPO . |
| 9109950 | 7/1991 | WIPO . |
| 9206188 | 4/1992 | WIPO . |

OTHER PUBLICATIONS

Bernad et al., 1989, "A Conserved 3'–5' Exonuclease Active Site in Prokaryotic and Eukaryotic DNA Polymerases" Cell 59:219–228.

Lawyer et al., 1989, "Isolation, Characterization, and Expression in *Escherichia coli* of the DNA Polymerase Gene From *Thermus Aquaticus*" J. Biol. Chem 264(11):6427–6437.

Leavitt and Ito, 1989, "T5 DNA Polymerase: Structural–Functional Relationships to Other DNA Polymerases" Proc. Natl. Acad. Sci. USA 86:4465–4469.

*Primary Examiner*—Keith D. Hendricks
*Attorney, Agent, or Firm*—George W. Johnston; Dennis P. Tramaloni; Douglas A. Petry

[57] ABSTRACT

The present invention relates to thermostable DNA polymerases which exhibit a different level of 5' to 3' exonuclease activity than their respective native polymerases. Particular conserved amino acid domains in thermostable DNA polymerases are mutated or deleted to alter the 5' to 3' exonuclease activity of the polymerases. The present invention also relates to means for isolating and producing such altered polymerases.

13 Claims, No Drawings

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:

( A ) LENGTH: 2499 base pairs ( B ) TYPE: nucleic acid ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Thermus aquaticus ( i x ) FEATURE:
( A ) NAME/KEY: CDS
( B ) LOCATION: 1..2496

( x i ) SEQUENCE DESCRIPTION: SEQ ID NO:1:

ATG AGG GGG ATG CTG CCC CTC TTT GAG CCC AAG GGC CGG GTC CTC CTG 48
Met Arg Gly Met Leu Pro Leu Phe Glu Pro Lys Gly Arg Val Leu Leu
1 5 10 15

GTG GAC GGC CAC CAC CTG GCC TAC CGC ACC TTC CAC GCC CTG AAG GGC 96
Val Asp Gly His His Leu Ala Tyr Arg Thr Phe His Ala Leu Lys Gly
20 25 30

CTC ACC ACC AGC CGG GGG GAG CCG GTG CAG GCG GTC TAC GGC TTC GCC 144
Leu Thr Thr Ser Arg Gly Glu Pro Val Gln Ala Val Tyr Gly Phe Ala
35 40 45

AAG AGC CTC CTC AAG GCC CTC AAG GAG GAC GGG GAC GCG GTG ATC GTG 192
Lys Ser Leu Leu Lys Ala Leu Lys Glu Asp Gly Asp Ala Val Ile Val
50 55 60

GTC TTT GAC GCC AAG GCC CCC TCC TTC CGC CAC GAG GCC TAC GGG GGG 240
Val Phe Asp Ala Lys Ala Pro Ser Phe Arg His Glu Ala Tyr Gly Gly
65 70 75 80

TAC AAG GCG GGC CGG GCC CCC ACG CCG GAG GAC TTT CCC CGG CAA CTC 288
Tyr Lys Ala Gly Arg Ala Pro Thr Pro Glu Asp Phe Pro Arg Gln Leu
85 90 95

GCC CTC ATC AAG GAG CTG GTG GAC CTC CTG GGG CTG GCG CGC CTC GAG 336
Ala Leu Ile Lys Glu Leu Val Asp Leu Leu Gly Leu Ala Arg Leu Glu
100 105 110

GTC CCG GGC TAC GAG GCG GAC GAC GTC CTG GCC AGC CTG GCC AAG AAG 384
Val Pro Gly Tyr Glu Ala Asp Asp Val Leu Ala Ser Leu Ala Lys Lys
115 120 125

GCG GAA AAG GAG GGC TAC GAG GTC CGC ATC CTC ACC GCC GAC AAA GAC 432
Ala Glu Lys Glu Gly Tyr Glu Val Arg Ile Leu Thr Ala Asp Lys Asp
130 135 140

CTT TAC CAG CTC CTT TCC GAC CGC ATC CAC GTC CTC CAC CCC GAG GGG 480
Leu Tyr Gln Leu Leu Ser Asp Arg Ile His Val Leu His Pro Glu Gly
145 150 155 160

TAC CTC ATC ACC CCG GCC TGG CTT TGG GAA AAG TAC GGC CTG AGG CCC 528
Tyr Leu Ile Thr Pro Ala Trp Leu Trp Glu Lys Tyr Gly Leu Arg Pro
165 170 175

GAC CAG TGG GCC GAC TAC CGG GCC CTG ACC GGG GAC GAG TCC GAC AAC 576
Asp Gln Trp Ala Asp Tyr Arg Ala Leu Thr Gly Asp Glu Ser Asp Asn
180 185 190

CTT CCC GGG GTC AAG GGC ATC GGG GAG AAG ACG GCG AGG AAG CTT CTG 624
Leu Pro Gly Val Lys Gly Ile Gly Glu Lys Thr Ala Arg Lys Leu Leu
195 200 205

GAG GAG TGG GGG AGC CTG GAA GCC CTC CTC AAG AAC CTG GAC CGG CTG 672
Glu Glu Trp Gly Ser Leu Glu Ala Leu Leu Lys Asn Leu Asp Arg Leu
210 215 220

AAG CCC GCC ATC CGG GAG AAG ATC CTG GCC CAC ATG GAC GAT CTG AAG 720
Lys Pro Ala Ile Arg Glu Lys Ile Leu Ala His Met Asp Asp Leu Lys
225 230 235 240

CTC TCC TGG GAC CTG GCC AAG GTG CGC ACC GAC CTG CCC CTG GAG GTG 768
Leu Ser Trp Asp Leu Ala Lys Val Arg Thr Asp Leu Pro Leu Glu Val
245 250 255

GAC TTC GCC AAA AGG CGG GAG CCC GAC CGG GAG AGG CTT AGG GCC TTT 816
Asp Phe Ala Lys Arg Arg Glu Pro Asp Arg Glu Arg Leu Arg Ala Phe

-continued 260 265 270

CTG GAG AGG CTT GAG TTT GGC AGC CTC CTC CAC GAG TTC GGC CTT CTG 864
Leu Glu Arg Leu Glu Phe Gly Ser Leu Leu His Glu Phe Gly Leu Leu
275 280 285

GAA AGC CCC AAG GCC CTG GAG GAG GCC CCC TGG CCC CCG CCG GAA GGG 912
Glu Ser Pro Lys Ala Leu Glu Glu Ala Pro Trp Pro Pro Pro Glu Gly
290 295 300

GCC TTC GTG GGC TTT GTG CTT TCC CGC AAG GAG CCC ATG TGG GCC GAT 960
Ala Phe Val Gly Phe Val Leu Ser Arg Lys Glu Pro Met Trp Ala Asp
305 310 315 320

CTT CTG GCC CTG GCC GCC GCC AGG GGG GGC CGG GTC CAC CGG GCC CCC 1008
Leu Leu Ala Leu Ala Ala Ala Arg Gly Gly Arg Val His Arg Ala Pro
325 330 335

GAG CCT TAT AAA GCC CTC AGG GAC CTG AAG GAG GCG CGG GGG CTT CTC 1056
Glu Pro Tyr Lys Ala Leu Arg Asp Leu Lys Glu Ala Arg Gly Leu Leu
340 345 350

GCC AAA GAC CTG AGC GTT CTG GCC CTG AGG GAA GGC CTT GGC CTC CCG 1104
Ala Lys Asp Leu Ser Val Leu Ala Leu Arg Glu Gly Leu Gly Leu Pro
355 360 365

CCC GGC GAC GAC CCC ATG CTC CTC GCC TAC CTC CTG GAC CCT TCC AAC 1152
Pro Gly Asp Asp Pro Met Leu Leu Ala Tyr Leu Leu Asp Pro Ser Asn
370 375 380

ACC ACC CCC GAG GGG GTG GCC CGG CGC TAC GGC GGG GAG TGG ACG GAG 1200
Thr Thr Pro Glu Gly Val Ala Arg Arg Tyr Gly Gly Glu Trp Thr Glu
385 390 395 400

GAG GCG GGG GAG CGG GCC GCC CTT TCC GAG AGG CTC TTC GCC AAC CTG 1248
Glu Ala Gly Glu Arg Ala Ala Leu Ser Glu Arg Leu Phe Ala Asn Leu
405 410 415

TGG GGG AGG CTT GAG GGG GAG GAG AGG CTC CTT TGG CTT TAC CGG GAG 1296
Trp Gly Arg Leu Glu Gly Glu Glu Arg Leu Leu Trp Leu Tyr Arg Glu
420 425 430

GTG GAG AGG CCC CTT TCC GCT GTC CTG GCC CAC ATG GAG GCC ACG GGG 1344
Val Glu Arg Pro Leu Ser Ala Val Leu Ala His Met Glu Ala Thr Gly
435 440 445

GTG CGC CTG GAC GTG GCC TAT CTC AGG GCC TTG TCC CTG GAG GTG GCC 1392
Val Arg Leu Asp Val Ala Tyr Leu Arg Ala Leu Ser Leu Glu Val Ala
450 455 460

GAG GAG ATC GCC CGC CTC GAG GCC GAG GTC TTC CGC CTG GCC GGC CAC 1440
Glu Glu Ile Ala Arg Leu Glu Ala Glu Val Phe Arg Leu Ala Gly His
465 470 475 480

CCC TTC AAC CTC AAC TCC CGG GAC CAG CTG GAA AGG GTC CTC TTT GAC 1488
Pro Phe Asn Leu Asn Ser Arg Asp Gln Leu Glu Arg Val Leu Phe Asp
485 490 495

GAG CTA GGG CTT CCC GCC ATC GGC AAG ACG GAG AAG ACC GGC AAG CGC 1536
Glu Leu Gly Leu Pro Ala Ile Gly Lys Thr Glu Lys Thr Gly Lys Arg
500 505 510

TCC ACC AGC GCC GCC GTC CTG GAG GCC CTC CGC GAG GCC CAC CCC ATC 1584
Ser Thr Ser Ala Ala Val Leu Glu Ala Leu Arg Glu Ala His Pro Ile
515 520 525

GTG GAG AAG ATC CTG CAG TAC CGG GAG CTC ACC AAG CTG AAG AGC ACC 1632
Val Glu Lys Ile Leu Gln Tyr Arg Glu Leu Thr Lys Leu Lys Ser Thr
530 535 540

TAC ATT GAC CCC TTG CCG GAC CTC ATC CAC CCC AGG ACG GGC CGC CTC 1680
Tyr Ile Asp Pro Leu Pro Asp Leu Ile His Pro Arg Thr Gly Arg Leu
545 550 555 560

CAC ACC CGC TTC AAC CAG ACG GCC ACG GCC ACG GGC AGG CTA AGT AGC 1728
His Thr Arg Phe Asn Gln Thr Ala Thr Ala Thr Gly Arg Leu Ser Ser
565 570 575

TCC GAT CCC AAC CTC CAG AAC ATC CCC GTC CGC ACC CCG CTT GGG CAG 1776
Ser Asp Pro Asn Leu Gln Asn Ile Pro Val Arg Thr Pro Leu Gly Gln

-continued 580 585 590

AGG ATC CGC CGG GCC TTC ATC GCC GAG GAG GGG TGG CTA TTG GTG GCC 1824
Arg Ile Arg Arg Ala Phe Ile Ala Glu Glu Gly Trp Leu Leu Val Ala
595 600 605

CTG GAC TAT AGC CAG ATA GAG CTC AGG GTG CTG GCC CAC CTC TCC GGC 1872
Leu Asp Tyr Ser Gln Ile Glu Leu Arg Val Leu Ala His Leu Ser Gly
610 615 620

GAC GAG AAC CTG ATC CGG GTC TTC CAG GAG GGG CGG GAC ATC CAC ACG 1920
Asp Glu Asn Leu Ile Arg Val Phe Gln Glu Gly Arg Asp Ile His Thr
625 630 635 640

GAG ACC GCC AGC TGG ATG TTC GGC GTC CCC CGG GAG GCC GTG GAC CCC 1968
Glu Thr Ala Ser Trp Met Phe Gly Val Pro Arg Glu Ala Val Asp Pro
645 650 655

CTG ATG CGC CGG GCG GCC AAG ACC ATC AAC TTC GGG GTC CTC TAC GGC 2016
Leu Met Arg Arg Ala Ala Lys Thr Ile Asn Phe Gly Val Leu Tyr Gly
660 665 670

ATG TCG GCC CAC CGC CTC TCC CAG GAG CTA GCC ATC CCT TAC GAG GAG 2064
Met Ser Ala His Arg Leu Ser Gln Glu Leu Ala Ile Pro Tyr Glu Glu
675 680 685

GCC CAG GCC TTC ATT GAG CGC TAC TTT CAG AGC TTC CCC AAG GTG CGG 2112
Ala Gln Ala Phe Ile Glu Arg Tyr Phe Gln Ser Phe Pro Lys Val Arg
690 695 700

GCC TGG ATT GAG AAG ACC CTG GAG GAG GGC AGG AGG CGG GGG TAC GTG 2160
Ala Trp Ile Glu Lys Thr Leu Glu Glu Gly Arg Arg Arg Gly Tyr Val
705 710 715 720

GAG ACC CTC TTC GGC CGC CGC CGC TAC GTG CCA GAC CTA GAG GCC CGG 2208
Glu Thr Leu Phe Gly Arg Arg Arg Tyr Val Pro Asp Leu Glu Ala Arg
725 730 735

GTG AAG AGC GTG CGG GAG GCG GCC GAG CGC ATG GCC TTC AAC ATG CCC 2256
Val Lys Ser Val Arg Glu Ala Ala Glu Arg Met Ala Phe Asn Met Pro
740 745 750

GTC CAG GGC ACC GCC GCC GAC CTC ATG AAG CTG GCT ATG GTG AAG CTC 2304
Val Gln Gly Thr Ala Ala Asp Leu Met Lys Leu Ala Met Val Lys Leu
755 760 765

TTC CCC AGG CTG GAG GAA ATG GGG GCC AGG ATG CTC CTT CAG GTC CAC 2352
Phe Pro Arg Leu Glu Glu Met Gly Ala Arg Met Leu Leu Gln Val His
770 775 780

GAC GAG CTG GTC CTC GAG GCC CCA AAA GAG AGG GCG GAG GCC GTG GCC 2400
Asp Glu Leu Val Leu Glu Ala Pro Lys Glu Arg Ala Glu Ala Val Ala
785 790 795 800

CGG CTG GCC AAG GAG GTC ATG GAG GGG GTG TAT CCC CTG GCC GTG CCC 2448
Arg Leu Ala Lys Glu Val Met Glu Gly Val Tyr Pro Leu Ala Val Pro
805 810 815

CTG GAG GTG GAG GTG GGG ATA GGG GAG GAC TGG CTC TCC GCC AAG GAG 2496
Leu Glu Val Glu Val Gly Ile Gly Glu Asp Trp Leu Ser Ala Lys Glu
820 825 830

TGA 2499

( 2 ) INFORMATION FOR SEQ ID NO:2:

( i ) SEQUENCE CHARACTERISTICS:
( A ) LENGTH: 832 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Arg Gly Met Leu Pro Leu Phe Glu Pro Lys Gly Arg Val Leu Leu
1 5 10 15

Val Asp Gly His His Leu Ala Tyr Arg Thr Phe His Ala Leu Lys Gly

-continued 20 25 30

Leu Thr Thr Ser Arg Gly Glu Pro Val Gln Ala Val Tyr Gly Phe Ala
35 40 45

Lys Ser Leu Leu Lys Ala Leu Lys Glu Asp Gly Asp Ala Val Ile Val
50 55 60

Val Phe Asp Ala Lys Ala Pro Ser Phe Arg His Glu Ala Tyr Gly Gly
65 70 75 80

Tyr Lys Ala Gly Arg Ala Pro Thr Pro Glu Asp Phe Pro Arg Gln Leu
85 90 95

Ala Leu Ile Lys Glu Leu Val Asp Leu Leu Gly Leu Ala Arg Leu Glu
100 105 110

Val Pro Gly Tyr Glu Ala Asp Asp Val Leu Ala Ser Leu Ala Lys Lys
115 120 125

Ala Glu Lys Glu Gly Tyr Glu Val Arg Ile Leu Thr Ala Asp Lys Asp
130 135 140

Leu Tyr Gln Leu Leu Ser Asp Arg Ile His Val Leu His Pro Glu Gly
145 150 155 160

Tyr Leu Ile Thr Pro Ala Trp Leu Trp Glu Lys Tyr Gly Leu Arg Pro
165 170 175

Asp Gln Trp Ala Asp Tyr Arg Ala Leu Thr Gly Asp Glu Ser Asp Asn
180 185 190

Leu Pro Gly Val Lys Gly Ile Gly Glu Lys Thr Ala Arg Lys Leu Leu
195 200 205

Glu Glu Trp Gly Ser Leu Glu Ala Leu Leu Lys Asn Leu Asp Arg Leu
210 215 220

Lys Pro Ala Ile Arg Glu Lys Ile Leu Ala His Met Asp Asp Leu Lys
225 230 235 240

Leu Ser Trp Asp Leu Ala Lys Val Arg Thr Asp Leu Pro Leu Glu Val
245 250 255

Asp Phe Ala Lys Arg Arg Glu Pro Asp Arg Glu Arg Leu Arg Ala Phe
260 265 270

Leu Glu Arg Leu Glu Phe Gly Ser Leu Leu His Glu Phe Gly Leu Leu
275 280 285

Glu Ser Pro Lys Ala Leu Glu Glu Ala Pro Trp Pro Pro Pro Glu Gly
290 295 300

Ala Phe Val Gly Phe Val Leu Ser Arg Lys Glu Pro Met Trp Ala Asp
305 310 315 320

Leu Leu Ala Leu Ala Ala Ala Arg Gly Gly Arg Val His Arg Ala Pro
325 330 335

Glu Pro Tyr Lys Ala Leu Arg Asp Leu Lys Glu Ala Arg Gly Leu Leu
340 345 350

Ala Lys Asp Leu Ser Val Leu Ala Leu Arg Glu Gly Leu Gly Leu Pro
355 360 365

Pro Gly Asp Asp Pro Met Leu Leu Ala Tyr Leu Leu Asp Pro Ser Asn
370 375 380

Thr Thr Pro Glu Gly Val Ala Arg Arg Tyr Gly Gly Glu Trp Thr Glu
385 390 395 400

Glu Ala Gly Glu Arg Ala Ala Leu Ser Glu Arg Leu Phe Ala Asn Leu
405 410 415

Trp Gly Arg Leu Glu Gly Glu Glu Arg Leu Leu Trp Leu Tyr Arg Glu
420 425 430

Val Glu Arg Pro Leu Ser Ala Val Leu Ala His Met Glu Ala Thr Gly
435 440 445

-continued

Val Arg Leu Asp Val Ala Tyr Leu Arg Ala Leu Ser Leu Glu Val Ala
450 455 460

Glu Glu Ile Ala Arg Leu Glu Ala Glu Val Phe Arg Leu Ala Gly His
465 470 475 480

Pro Phe Asn Leu Asn Ser Arg Asp Gln Leu Glu Arg Val Leu Phe Asp
485 490 495

Glu Leu Gly Leu Pro Ala Ile Gly Lys Thr Glu Lys Thr Gly Lys Arg
500 505 510

Ser Thr Ser Ala Ala Val Leu Glu Ala Leu Arg Glu Ala His Pro Ile
515 520 525

Val Glu Lys Ile Leu Gln Tyr Arg Glu Leu Thr Lys Leu Lys Ser Thr
530 535 540

Tyr Ile Asp Pro Leu Pro Asp Leu Ile His Pro Arg Thr Gly Arg Leu
545 550 555 560

His Thr Arg Phe Asn Gln Thr Ala Thr Ala Thr Gly Arg Leu Ser Ser
565 570 575

Ser Asp Pro Asn Leu Gln Asn Ile Pro Val Arg Thr Pro Leu Gly Gln
580 585 590

Arg Ile Arg Arg Ala Phe Ile Ala Glu Glu Gly Trp Leu Leu Val Ala
595 600 605

Leu Asp Tyr Ser Gln Ile Glu Leu Arg Val Leu Ala His Leu Ser Gly
610 615 620

Asp Glu Asn Leu Ile Arg Val Phe Gln Glu Gly Arg Asp Ile His Thr
625 630 635 640

Glu Thr Ala Ser Trp Met Phe Gly Val Pro Arg Glu Ala Val Asp Pro
645 650 655

Leu Met Arg Arg Ala Ala Lys Thr Ile Asn Phe Gly Val Leu Tyr Gly
660 665 670

Met Ser Ala His Arg Leu Ser Gln Glu Leu Ala Ile Pro Tyr Glu Glu
675 680 685

Ala Gln Ala Phe Ile Glu Arg Tyr Phe Gln Ser Phe Pro Lys Val Arg
690 695 700

Ala Trp Ile Glu Lys Thr Leu Glu Glu Gly Arg Arg Arg Gly Tyr Val
705 710 715 720

Glu Thr Leu Phe Gly Arg Arg Arg Tyr Val Pro Asp Leu Glu Ala Arg
725 730 735

Val Lys Ser Val Arg Glu Ala Ala Glu Arg Met Ala Phe Asn Met Pro
740 745 750

Val Gln Gly Thr Ala Ala Asp Leu Met Lys Leu Ala Met Val Lys Leu
755 760 765

Phe Pro Arg Leu Glu Glu Met Gly Ala Arg Met Leu Leu Gln Val His
770 775 780

Asp Glu Leu Val Leu Glu Ala Pro Lys Glu Arg Ala Glu Ala Val Ala
785 790 795 800

Arg Leu Ala Lys Glu Val Met Glu Gly Val Tyr Pro Leu Ala Val Pro
805 810 815

Leu Glu Val Glu Val Gly Ile Gly Glu Asp Trp Leu Ser Ala Lys Glu
820 825 830

( 2 ) INFORMATION FOR SEQ ID NO:3:

( i ) SEQUENCE CHARACTERISTICS:

( A ) LENGTH: 2682 base pairs ( B ) TYPE: nucleic acid ( C ) STRANDEDNESS: single ( D ) TOPOLOGY: linear -continued ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Thermotoga maritima ( i x ) FEATURE:
( A ) NAME/KEY: CDS
( B ) LOCATION: 1..2679

( x i ) SEQUENCE DESCRIPTION: SEQ ID NO:3:

```
ATG GCG AGA CTA TTT CTC TTT GAT GGA ACT GCT CTG GCC TAC AGA GCG   48
Met Ala Arg Leu Phe Leu Phe Asp Gly Thr Ala Leu Ala Tyr Arg Ala
 1               5                  10                  15

TAC TAT GCG CTC GAT AGA TCG CTT TCT ACT TCC ACC GGC ATT CCC ACA   96
Tyr Tyr Ala Leu Asp Arg Ser Leu Ser Thr Ser Thr Gly Ile Pro Thr
            20                  25                  30

AAC GCC ACA TAC GGT GTG GCG AGG ATG CTG GTG AGA TTC ATC AAA GAC  144
Asn Ala Thr Tyr Gly Val Ala Arg Met Leu Val Arg Phe Ile Lys Asp
        35                  40                  45

CAT ATC ATT GTC GGA AAA GAC TAC GTT GCT GTG GCT TTC GAC AAA AAA  192
His Ile Ile Val Gly Lys Asp Tyr Val Ala Val Ala Phe Asp Lys Lys
    50                  55                  60

GCT GCC ACC TTC AGA CAC AAG CTC CTC GAG ACT TAC AAG GCT CAA AGA  240
Ala Ala Thr Phe Arg His Lys Leu Leu Glu Thr Tyr Lys Ala Gln Arg
 65                  70                  75                  80

CCA AAG ACT CCG GAT CTC CTG ATT CAG CAG CTT CCG TAC ATA AAG AAG  288
Pro Lys Thr Pro Asp Leu Leu Ile Gln Gln Leu Pro Tyr Ile Lys Lys
                85                  90                  95

CTG GTC GAA GCC CTT GGA ATG AAA GTG CTG GAG GTA GAA GGA TAC GAA  336
Leu Val Glu Ala Leu Gly Met Lys Val Leu Glu Val Glu Gly Tyr Glu
            100                 105                 110

GCG GAC GAT ATA ATT GCC ACT CTG GCT GTG AAG GGG CTT CCG CTT TTT  384
Ala Asp Asp Ile Ile Ala Thr Leu Ala Val Lys Gly Leu Pro Leu Phe
        115                 120                 125

GAT GAA ATA TTC ATA GTG ACC GGA GAT AAA GAC ATG CTT CAG CTT GTG  432
Asp Glu Ile Phe Ile Val Thr Gly Asp Lys Asp Met Leu Gln Leu Val
    130                 135                 140

AAC GAA AAG ATC AAG GTG TGG CGA ATC GTA AAA GGG ATA TCC GAT CTG  480
Asn Glu Lys Ile Lys Val Trp Arg Ile Val Lys Gly Ile Ser Asp Leu
145                 150                 155                 160

GAA CTT TAC GAT GCG CAG AAG GTG AAG GAA AAA TAC GGT GTT GAA CCC  528
Glu Leu Tyr Asp Ala Gln Lys Val Lys Glu Lys Tyr Gly Val Glu Pro
                165                 170                 175

CAG CAG ATC CCG GAT CTT CTG GCT CTA ACC GGA GAT GAA ATA GAC AAC  576
Gln Gln Ile Pro Asp Leu Leu Ala Leu Thr Gly Asp Glu Ile Asp Asn
            180                 185                 190

ATC CCC GGT GTA ACT GGG ATA GGT GAA AAG ACT GCT GTT CAG CTT CTA  624
Ile Pro Gly Val Thr Gly Ile Gly Glu Lys Thr Ala Val Gln Leu Leu
        195                 200                 205

GAG AAG TAC AAA GAC CTC GAA GAC ATA CTG AAT CAT GTT CGC GAA CTT  672
Glu Lys Tyr Lys Asp Leu Glu Asp Ile Leu Asn His Val Arg Glu Leu
    210                 215                 220

CCT CAA AAG GTG AGA AAA GCC CTG CTT CGA GAC AGA GAA AAC GCC ATT  720
Pro Gln Lys Val Arg Lys Ala Leu Leu Arg Asp Arg Glu Asn Ala Ile
225                 230                 235                 240

CTC AGC AAA AAG CTG GCG ATT CTG GAA ACA AAC GTT CCC ATT GAA ATA  768
Leu Ser Lys Lys Leu Ala Ile Leu Glu Thr Asn Val Pro Ile Glu Ile
                245                 250                 255
```

-continued

```
AAC TGG GAA GAA CTT CGC TAC CAG GGC TAC GAC AGA GAG AAA CTC TTA     816
Asn Trp Glu Glu Leu Arg Tyr Gln Gly Tyr Asp Arg Glu Lys Leu Leu
            260                 265                 270

CCA CTT TTG AAA GAA CTG GAA TTC GCA TCC ATC ATG AAG GAA CTT CAA     864
Pro Leu Leu Lys Glu Leu Glu Phe Ala Ser Ile Met Lys Glu Leu Gln
        275                 280                 285

CTG TAC GAA GAG TCC GAA CCC GTT GGA TAC AGA ATA GTG AAA GAC CTA     912
Leu Tyr Glu Glu Ser Glu Pro Val Gly Tyr Arg Ile Val Lys Asp Leu
    290                 295                 300

GTG GAA TTT GAA AAA CTC ATA GAG AAA CTG AGA GAA TCC CCT TCG TTC     960
Val Glu Phe Glu Lys Leu Ile Glu Lys Leu Arg Glu Ser Pro Ser Phe
305                 310                 315                 320

GCC ATA GAT CTT GAG ACG TCT TCC CTC GAT CCT TTC GAC TGC GAC ATT    1008
Ala Ile Asp Leu Glu Thr Ser Ser Leu Asp Pro Phe Asp Cys Asp Ile
                325                 330                 335

GTC GGT ATC TCT GTG TCT TTC AAA CCA AAG GAA GCG TAC TAC ATA CCA    1056
Val Gly Ile Ser Val Ser Phe Lys Pro Lys Glu Ala Tyr Tyr Ile Pro
            340                 345                 350

CTC CAT CAT AGA AAC GCC CAG AAC CTG GAC GAA AAA GAG GTT CTG AAA    1104
Leu His His Arg Asn Ala Gln Asn Leu Asp Glu Lys Glu Val Leu Lys
        355                 360                 365

AAG CTC AAA GAA ATT CTG GAG GAC CCC GGA GCA AAG ATC GTT GGT CAG    1152
Lys Leu Lys Glu Ile Leu Glu Asp Pro Gly Ala Lys Ile Val Gly Gln
    370                 375                 380

AAT TTG AAA TTC GAT TAC AAG GTG TTG ATG GTG AAG GGT GTT GAA CCT    1200
Asn Leu Lys Phe Asp Tyr Lys Val Leu Met Val Lys Gly Val Glu Pro
385                 390                 395                 400

GTT CCT CCT TAC TTC GAC ACG ATG ATA GCG GCT TAC CTT CTT GAG CCG    1248
Val Pro Pro Tyr Phe Asp Thr Met Ile Ala Ala Tyr Leu Leu Glu Pro
                405                 410                 415

AAC GAA AAG AAG TTC AAT CTG GAC GAT CTC GCA TTG AAA TTT CTT GGA    1296
Asn Glu Lys Lys Phe Asn Leu Asp Asp Leu Ala Leu Lys Phe Leu Gly
            420                 425                 430

TAC AAA ATG ACA TCT TAC CAA GAG CTC ATG TCC TTC TCT TTT CCG CTG    1344
Tyr Lys Met Thr Ser Tyr Gln Glu Leu Met Ser Phe Ser Phe Pro Leu
        435                 440                 445

TTT GGT TTC AGT TTT GCC GAT GTT CCT GTA GAA AAA GCA GCG AAC TAC    1392
Phe Gly Phe Ser Phe Ala Asp Val Pro Val Glu Lys Ala Ala Asn Tyr
    450                 455                 460

TCC TGT GAA GAT GCA GAC ATC ACC TAC AGA CTT TAC AAG ACC CTG AGC    1440
Ser Cys Glu Asp Ala Asp Ile Thr Tyr Arg Leu Tyr Lys Thr Leu Ser
465                 470                 475                 480

TTA AAA CTC CAC GAG GCA GAT CTG GAA AAC GTG TTC TAC AAG ATA GAA    1488
Leu Lys Leu His Glu Ala Asp Leu Glu Asn Val Phe Tyr Lys Ile Glu
                485                 490                 495

ATG CCC CTT GTG AAC GTG CTT GCA CGG ATG GAA CTG AAC GGT GTG TAT    1536
Met Pro Leu Val Asn Val Leu Ala Arg Met Glu Leu Asn Gly Val Tyr
            500                 505                 510

GTG GAC ACA GAG TTC CTG AAG AAA CTC TCA GAA GAG TAC GGA AAA AAA    1584
Val Asp Thr Glu Phe Leu Lys Lys Leu Ser Glu Glu Tyr Gly Lys Lys
        515                 520                 525

CTC GAA GAA CTG GCA GAG GAA ATA TAC AGG ATA GCT GGA GAG CCG TTC    1632
Leu Glu Glu Leu Ala Glu Glu Ile Tyr Arg Ile Ala Gly Glu Pro Phe
    530                 535                 540

AAC ATA AAC TCA CCG AAG CAG GTT TCA AGG ATC CTT TTT GAA AAA CTC    1680
Asn Ile Asn Ser Pro Lys Gln Val Ser Arg Ile Leu Phe Glu Lys Leu
545                 550                 555                 560

GGC ATA AAA CCA CGT GGT AAA ACG ACG AAA ACG GGA GAC TAT TCA ACA    1728
Gly Ile Lys Pro Arg Gly Lys Thr Thr Lys Thr Gly Asp Tyr Ser Thr
                565                 570                 575
```

-continued

```
CGC ATA GAA GTC CTC GAG GAA CTT GCC GGT GAA CAC GAA ATC ATT CCT   1776
Arg Ile Glu Val Leu Glu Glu Leu Ala Gly Glu His Glu Ile Ile Pro
            580                 585                 590

CTG ATT CTT GAA TAC AGA AAG ATA CAG AAA TTG AAA TCA ACC TAC ATA   1824
Leu Ile Leu Glu Tyr Arg Lys Ile Gln Lys Leu Lys Ser Thr Tyr Ile
        595                 600                 605

GAC GCT CTT CCC AAG ATG GTC AAC CCA AAG ACC GGA AGG ATT CAT GCT   1872
Asp Ala Leu Pro Lys Met Val Asn Pro Lys Thr Gly Arg Ile His Ala
    610                 615                 620

TCT TTC AAT CAA ACG GGG ACT GCC ACT GGA AGA CTT AGC AGC AGC GAT   1920
Ser Phe Asn Gln Thr Gly Thr Ala Thr Gly Arg Leu Ser Ser Ser Asp
625                 630                 635                 640

CCC AAT CTT CAG AAC CTC CCG ACG AAA AGT GAA GAG GGA AAA GAA ATC   1968
Pro Asn Leu Gln Asn Leu Pro Thr Lys Ser Glu Glu Gly Lys Glu Ile
                645                 650                 655

AGG AAA GCG ATA GTT CCT CAG GAT CCA AAC TGG TGG ATC GTC AGT GCC   2016
Arg Lys Ala Ile Val Pro Gln Asp Pro Asn Trp Trp Ile Val Ser Ala
            660                 665                 670

GAC TAC TCC CAA ATA GAA CTG AGG ATC CTC GCC CAT CTC AGT GGT GAT   2064
Asp Tyr Ser Gln Ile Glu Leu Arg Ile Leu Ala His Leu Ser Gly Asp
        675                 680                 685

GAG AAT CTT TTG AGG GCA TTC GAA GAG GGC ATC GAC GTC CAC ACT CTA   2112
Glu Asn Leu Leu Arg Ala Phe Glu Glu Gly Ile Asp Val His Thr Leu
    690                 695                 700

ACA GCT TCC AGA ATA TTC AAC GTG AAA CCC GAA GAA GTA ACC GAA GAA   2160
Thr Ala Ser Arg Ile Phe Asn Val Lys Pro Glu Glu Val Thr Glu Glu
705                 710                 715                 720

ATG CGC CGC GCT GGT AAA ATG GTT AAT TTT TCC ATC ATA TAC GGT GTA   2208
Met Arg Arg Ala Gly Lys Met Val Asn Phe Ser Ile Ile Tyr Gly Val
                725                 730                 735

ACA CCT TAC GGT CTG TCT GTG AGG CTT GGA GTA CCT GTG AAA GAA GCA   2256
Thr Pro Tyr Gly Leu Ser Val Arg Leu Gly Val Pro Val Lys Glu Ala
            740                 745                 750

GAA AAG ATG ATC GTC AAC TAC TTC GTC CTC TAC CCA AAG GTG CGC GAT   2304
Glu Lys Met Ile Val Asn Tyr Phe Val Leu Tyr Pro Lys Val Arg Asp
        755                 760                 765

TAC ATT CAG AGG GTC GTA TCG GAA GCG AAA GAA AAA GGC TAT GTT AGA   2352
Tyr Ile Gln Arg Val Val Ser Glu Ala Lys Glu Lys Gly Tyr Val Arg
    770                 775                 780

ACG CTG TTT GGA AGA AAA AGA GAC ATA CCA CAG CTC ATG GCC CGG GAC   2400
Thr Leu Phe Gly Arg Lys Arg Asp Ile Pro Gln Leu Met Ala Arg Asp
785                 790                 795                 800

AGG AAC ACA CAG GCT GAA GGA GAA CGA ATT GCC ATA AAC ACT CCC ATA   2448
Arg Asn Thr Gln Ala Glu Gly Glu Arg Ile Ala Ile Asn Thr Pro Ile
                805                 810                 815

CAG GGT ACA GCA GCG GAT ATA ATA AAG CTG GCT ATG ATA GAA ATA GAC   2496
Gln Gly Thr Ala Ala Asp Ile Ile Lys Leu Ala Met Ile Glu Ile Asp
            820                 825                 830

AGG GAA CTG AAA GAA AGA AAA ATG AGA TCG AAG ATG ATC ATA CAG GTC   2544
Arg Glu Leu Lys Glu Arg Lys Met Arg Ser Lys Met Ile Ile Gln Val
        835                 840                 845

CAC GAC GAA CTG GTT TTT GAA GTG CCC AAT GAG GAA AAG GAC GCG CTC   2592
His Asp Glu Leu Val Phe Glu Val Pro Asn Glu Glu Lys Asp Ala Leu
    850                 855                 860

GTC GAG CTG GTG AAA GAC AGA ATG ACG AAT GTG GTA AAG CTT TCA GTG   2640
Val Glu Leu Val Lys Asp Arg Met Thr Asn Val Val Lys Leu Ser Val
865                 870                 875                 880

CCG CTC GAA GTG GAT GTA ACC ATC GGC AAA ACA TGG TCG TGA           2682
Pro Leu Glu Val Asp Val Thr Ile Gly Lys Thr Trp Ser
                885                 890
```

( 2 ) INFORMATION FOR SEQ ID NO:4:

( i ) SEQUENCE CHARACTERISTICS:
( A ) LENGTH: 893 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met Ala Arg Leu Phe Leu Phe Asp Gly Thr Ala Leu Ala Tyr Arg Ala
1 5 10 15

Tyr Tyr Ala Leu Asp Arg Ser Leu Ser Thr Ser Thr Gly Ile Pro Thr
20 25 30

Asn Ala Thr Tyr Gly Val Ala Arg Met Leu Val Arg Phe Ile Lys Asp
35 40 45

His Ile Ile Val Gly Lys Asp Tyr Val Ala Val Ala Phe Asp Lys Lys
50 55 60

Ala Ala Thr Phe Arg His Lys Leu Leu Glu Thr Tyr Lys Ala Gln Arg
65 70 75 80

Pro Lys Thr Pro Asp Leu Leu Ile Gln Gln Leu Pro Tyr Ile Lys Lys
85 90 95

Leu Val Glu Ala Leu Gly Met Lys Val Leu Glu Val Glu Gly Tyr Glu
100 105 110

Ala Asp Asp Ile Ile Ala Thr Leu Ala Val Lys Gly Leu Pro Leu Phe
115 120 125

Asp Glu Ile Phe Ile Val Thr Gly Asp Lys Asp Met Leu Gln Leu Val
130 135 140

Asn Glu Lys Ile Lys Val Trp Arg Ile Val Lys Gly Ile Ser Asp Leu
145 150 155 160

Glu Leu Tyr Asp Ala Gln Lys Val Lys Glu Lys Tyr Gly Val Glu Pro
165 170 175

Gln Gln Ile Pro Asp Leu Leu Ala Leu Thr Gly Asp Glu Ile Asp Asn
180 185 190

Ile Pro Gly Val Thr Gly Ile Gly Glu Lys Thr Ala Val Gln Leu Leu
195 200 205

Glu Lys Tyr Lys Asp Leu Glu Asp Ile Leu Asn His Val Arg Glu Leu
210 215 220

Pro Gln Lys Val Arg Lys Ala Leu Leu Arg Asp Arg Glu Asn Ala Ile
225 230 235 240

Leu Ser Lys Lys Leu Ala Ile Leu Glu Thr Asn Val Pro Ile Glu Ile
245 250 255

Asn Trp Glu Glu Leu Arg Tyr Gln Gly Tyr Asp Arg Glu Lys Leu Leu
260 265 270

Pro Leu Leu Lys Glu Leu Glu Phe Ala Ser Ile Met Lys Glu Leu Gln
275 280 285

Leu Tyr Glu Glu Ser Glu Pro Val Gly Tyr Arg Ile Val Lys Asp Leu
290 295 300

Val Glu Phe Glu Lys Leu Ile Glu Lys Leu Arg Glu Ser Pro Ser Phe
305 310 315 320

Ala Ile Asp Leu Glu Thr Ser Ser Leu Asp Pro Phe Asp Cys Asp Ile
325 330 335

Val Gly Ile Ser Val Ser Phe Lys Pro Lys Glu Ala Tyr Tyr Ile Pro
340 345 350

Leu His His Arg Asn Ala Gln Asn Leu Asp Glu Lys Glu Val Leu Lys
355 360 365

-continued

| | | | | | | | | | | | | | | | |
|---|---|---|---|---|---|---|---|---|---|---|---|---|---|---|---|
| Lys | Leu | Lys | Glu | Ile | Leu | Glu | Asp | Pro | Gly | Ala | Lys | Ile | Val | Gly | Gln |
| | 370 | | | | | 375 | | | | | 380 | | | | |
| Asn | Leu | Lys | Phe | Asp | Tyr | Lys | Val | Leu | Met | Val | Lys | Gly | Val | Glu | Pro |
| 385 | | | | | 390 | | | | | 395 | | | | | 400 |
| Val | Pro | Pro | Tyr | Phe | Asp | Thr | Met | Ile | Ala | Ala | Tyr | Leu | Leu | Glu | Pro |
| | | | | 405 | | | | | 410 | | | | | 415 | |
| Asn | Glu | Lys | Lys | Phe | Asn | Leu | Asp | Asp | Leu | Ala | Leu | Lys | Phe | Leu | Gly |
| | | | 420 | | | | | 425 | | | | | 430 | | |
| Tyr | Lys | Met | Thr | Ser | Tyr | Gln | Glu | Leu | Met | Ser | Phe | Ser | Phe | Pro | Leu |
| | | 435 | | | | | 440 | | | | | 445 | | | |
| Phe | Gly | Phe | Ser | Phe | Ala | Asp | Val | Pro | Val | Glu | Lys | Ala | Ala | Asn | Tyr |
| | 450 | | | | | 455 | | | | | 460 | | | | |
| Ser | Cys | Glu | Asp | Ala | Asp | Ile | Thr | Tyr | Arg | Leu | Tyr | Lys | Thr | Leu | Ser |
| 465 | | | | | 470 | | | | | 475 | | | | | 480 |
| Leu | Lys | Leu | His | Glu | Ala | Asp | Leu | Glu | Asn | Val | Phe | Tyr | Lys | Ile | Glu |
| | | | | 485 | | | | | 490 | | | | | 495 | |
| Met | Pro | Leu | Val | Asn | Val | Leu | Ala | Arg | Met | Glu | Leu | Asn | Gly | Val | Tyr |
| | | | 500 | | | | | 505 | | | | | 510 | | |
| Val | Asp | Thr | Glu | Phe | Leu | Lys | Lys | Leu | Ser | Glu | Glu | Tyr | Gly | Lys | Lys |
| | | 515 | | | | | 520 | | | | | 525 | | | |
| Leu | Glu | Glu | Leu | Ala | Glu | Glu | Ile | Tyr | Arg | Ile | Ala | Gly | Glu | Pro | Phe |
| | 530 | | | | | 535 | | | | | 540 | | | | |
| Asn | Ile | Asn | Ser | Pro | Lys | Gln | Val | Ser | Arg | Ile | Leu | Phe | Glu | Lys | Leu |
| 545 | | | | | 550 | | | | | 555 | | | | | 560 |
| Gly | Ile | Lys | Pro | Arg | Gly | Lys | Thr | Thr | Lys | Thr | Gly | Asp | Tyr | Ser | Thr |
| | | | | 565 | | | | | 570 | | | | | 575 | |
| Arg | Ile | Glu | Val | Leu | Glu | Glu | Leu | Ala | Gly | Glu | His | Glu | Ile | Ile | Pro |
| | | | 580 | | | | | 585 | | | | | 590 | | |
| Leu | Ile | Leu | Glu | Tyr | Arg | Lys | Ile | Gln | Lys | Leu | Lys | Ser | Thr | Tyr | Ile |
| | | 595 | | | | | 600 | | | | | 605 | | | |
| Asp | Ala | Leu | Pro | Lys | Met | Val | Asn | Pro | Lys | Thr | Gly | Arg | Ile | His | Ala |
| | 610 | | | | | 615 | | | | | 620 | | | | |
| Ser | Phe | Asn | Gln | Thr | Gly | Thr | Ala | Thr | Gly | Arg | Leu | Ser | Ser | Ser | Asp |
| 625 | | | | | 630 | | | | | 635 | | | | | 640 |
| Pro | Asn | Leu | Gln | Asn | Leu | Pro | Thr | Lys | Ser | Glu | Glu | Gly | Lys | Glu | Ile |
| | | | | 645 | | | | | 650 | | | | | 655 | |
| Arg | Lys | Ala | Ile | Val | Pro | Gln | Asp | Pro | Asn | Trp | Trp | Ile | Val | Ser | Ala |
| | | | 660 | | | | | 665 | | | | | 670 | | |
| Asp | Tyr | Ser | Gln | Ile | Glu | Leu | Arg | Ile | Leu | Ala | His | Leu | Ser | Gly | Asp |
| | | 675 | | | | | 680 | | | | | 685 | | | |
| Glu | Asn | Leu | Leu | Arg | Ala | Phe | Glu | Glu | Gly | Ile | Asp | Val | His | Thr | Leu |
| | 690 | | | | | 695 | | | | | 700 | | | | |
| Thr | Ala | Ser | Arg | Ile | Phe | Asn | Val | Lys | Pro | Glu | Glu | Val | Thr | Glu | Glu |
| 705 | | | | | 710 | | | | | 715 | | | | | 720 |
| Met | Arg | Arg | Ala | Gly | Lys | Met | Val | Asn | Phe | Ser | Ile | Ile | Tyr | Gly | Val |
| | | | | 725 | | | | | 730 | | | | | 735 | |
| Thr | Pro | Tyr | Gly | Leu | Ser | Val | Arg | Leu | Gly | Val | Pro | Val | Lys | Glu | Ala |
| | | | 740 | | | | | 745 | | | | | 750 | | |
| Glu | Lys | Met | Ile | Val | Asn | Tyr | Phe | Val | Leu | Tyr | Pro | Lys | Val | Arg | Asp |
| | | 755 | | | | | 760 | | | | | 765 | | | |
| Tyr | Ile | Gln | Arg | Val | Val | Ser | Glu | Ala | Lys | Glu | Lys | Gly | Tyr | Val | Arg |
| | 770 | | | | | 775 | | | | | 780 | | | | |
| Thr | Leu | Phe | Gly | Arg | Lys | Arg | Asp | Ile | Pro | Gln | Leu | Met | Ala | Arg | Asp |

-continued

```
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
        835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890
```

( 2 ) INFORMATION FOR SEQ ID NO:5:

( i ) SEQUENCE CHARACTERISTICS:
( A ) LENGTH: 2493 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Thermus species sps17

( i x ) FEATURE:
( A ) NAME/KEY: CDS
( B ) LOCATION: 1..2490

( x i ) SEQUENCE DESCRIPTION: SEQ ID NO:5:

```
ATG CTG CCC CTC TTT GAG CCC AAG GGC CGG GTC CTC CTG GTG GAC GGC     48
Met Leu Pro Leu Phe Glu Pro Lys Gly Arg Val Leu Leu Val Asp Gly
  1               5                  10                  15

CAC CAC CTG GCC TAC CGC ACC TTT TTC GCC CTC AAG GGC CTC ACC ACC     96
His His Leu Ala Tyr Arg Thr Phe Phe Ala Leu Lys Gly Leu Thr Thr
            20                  25                  30

AGC CGG GGC GAG CCC GTG CAG GCG GTT TAT GGC TTC GCC AAA AGC CTC    144
Ser Arg Gly Glu Pro Val Gln Ala Val Tyr Gly Phe Ala Lys Ser Leu
        35                  40                  45

CTC AAG GCC CTG AAG GAG GAT GGG GAG GTG GCC ATC GTG GTC TTT GAC    192
Leu Lys Ala Leu Lys Glu Asp Gly Glu Val Ala Ile Val Val Phe Asp
    50                  55                  60

GCC AAG GCC CCC TCC TTC CGC CAC GAG GCC TAC GAG GCC TAC AAG GCG    240
Ala Lys Ala Pro Ser Phe Arg His Glu Ala Tyr Glu Ala Tyr Lys Ala
 65                  70                  75                  80

GGC CGG GCC CCC ACC CCG GAG GAC TTT CCC CGG CAG CTC GCC CTC ATC    288
Gly Arg Ala Pro Thr Pro Glu Asp Phe Pro Arg Gln Leu Ala Leu Ile
                85                  90                  95

AAG GAG CTG GTG GAC CTT TTG GGC CTC GTG CGC CTT GAG GTC CCG GGC    336
Lys Glu Leu Val Asp Leu Leu Gly Leu Val Arg Leu Glu Val Pro Gly
            100                 105                 110

TTT GAG GCG GAC GAT GTC CTC GCC ACC CTG GCC AAG AAG GCA GAA AGG    384
Phe Glu Ala Asp Asp Val Leu Ala Thr Leu Ala Lys Lys Ala Glu Arg
        115                 120                 125

GAG GGG TAC GAG GTG CGC ATC CTG AGC GCG GAC CGC GAC CTC TAC CAG    432
Glu Gly Tyr Glu Val Arg Ile Leu Ser Ala Asp Arg Asp Leu Tyr Gln
    130                 135                 140
```

-continued

```
CTC CTT TCC GAC CGG ATC CAC CTC CTC CAC CCC GAG GGG GAG GTC CTG      480
Leu Leu Ser Asp Arg Ile His Leu Leu His Pro Glu Gly Glu Val Leu
145                 150                 155                 160

ACC CCC GGG TGG CTC CAG GAG CGC TAC GGC CTC TCC CCG GAG AGG TGG      528
Thr Pro Gly Trp Leu Gln Glu Arg Tyr Gly Leu Ser Pro Glu Arg Trp
                165                 170                 175

GTG GAG TAC CGG GCC CTG GTG GGG GAC CCT TCG GAC AAC CTC CCC GGG      576
Val Glu Tyr Arg Ala Leu Val Gly Asp Pro Ser Asp Asn Leu Pro Gly
            180                 185                 190

GTG CCC GGC ATC GGG GAG AAG ACC GCC CTG AAG CTC CTG AAG GAG TGG      624
Val Pro Gly Ile Gly Glu Lys Thr Ala Leu Lys Leu Leu Lys Glu Trp
        195                 200                 205

GGT AGC CTG GAA GCG ATT CTA AAG AAC CTG GAC CAG GTG AAG CCG GAA      672
Gly Ser Leu Glu Ala Ile Leu Lys Asn Leu Asp Gln Val Lys Pro Glu
    210                 215                 220

AGG GTG CGG GAG GCC ATC CGG AAT AAC CTG GAT AAG CTC CAG ATG TCC      720
Arg Val Arg Glu Ala Ile Arg Asn Asn Leu Asp Lys Leu Gln Met Ser
225                 230                 235                 240

CTG GAG CTT TCC CGC CTC CGC ACC GAC CTC CCC CTG GAG GTG GAC TTC      768
Leu Glu Leu Ser Arg Leu Arg Thr Asp Leu Pro Leu Glu Val Asp Phe
                245                 250                 255

GCC AAG AGG CGG GAG CCC GAC TGG GAG GGG CTT AAG GCC TTT TTG GAG      816
Ala Lys Arg Arg Glu Pro Asp Trp Glu Gly Leu Lys Ala Phe Leu Glu
            260                 265                 270

CGG CTT GAG TTC GGA AGC CTC CTC CAC GAG TTC GGC CTT CTG GAG GCC      864
Arg Leu Glu Phe Gly Ser Leu Leu His Glu Phe Gly Leu Leu Glu Ala
        275                 280                 285

CCC AAG GAG GCG GAG GAG GCC CCC TGG CCC CCG CCT GGA GGG GCC TTT      912
Pro Lys Glu Ala Glu Glu Ala Pro Trp Pro Pro Pro Gly Gly Ala Phe
    290                 295                 300

TTG GGC TTC CTC CTC TCC CGC CCC GAG CCC ATG TGG GCG GAG CTT TTG      960
Leu Gly Phe Leu Leu Ser Arg Pro Glu Pro Met Trp Ala Glu Leu Leu
305                 310                 315                 320

GCC CTG GCG GGG GCC AAG GAG GGG CGG GTC CAT CGG GCG GAA GAC CCC     1008
Ala Leu Ala Gly Ala Lys Glu Gly Arg Val His Arg Ala Glu Asp Pro
                325                 330                 335

GTG GGG GCC CTA AAG GAC CTG AAG GAG ATC CGG GGC CTC CTC GCC AAG     1056
Val Gly Ala Leu Lys Asp Leu Lys Glu Ile Arg Gly Leu Leu Ala Lys
            340                 345                 350

GAC CTC TCG GTC CTG GCC CTG AGG GAG GGC CGG GAG ATC CCG CCG GGG     1104
Asp Leu Ser Val Leu Ala Leu Arg Glu Gly Arg Glu Ile Pro Pro Gly
        355                 360                 365

GAC GAC CCC ATG CTC CTC GCC TAC CTC CTG GAC CCG GGG AAC ACC AAC     1152
Asp Asp Pro Met Leu Leu Ala Tyr Leu Leu Asp Pro Gly Asn Thr Asn
    370                 375                 380

CCC GAG GGG GTG GCC CGG CGG TAC GGG GGG GAG TGG AAG GAG GAC GCC     1200
Pro Glu Gly Val Ala Arg Arg Tyr Gly Gly Glu Trp Lys Glu Asp Ala
385                 390                 395                 400

GCC GCC CGG GCC CTC CTT TCG GAA AGG CTC TGG CAG GCC CTT TAC CCC     1248
Ala Ala Arg Ala Leu Leu Ser Glu Arg Leu Trp Gln Ala Leu Tyr Pro
                405                 410                 415

CGG GTG GCG GAG GAG GAA AGG CTC CTT TGG CTC TAC CGG GAG GTG GAG     1296
Arg Val Ala Glu Glu Glu Arg Leu Leu Trp Leu Tyr Arg Glu Val Glu
            420                 425                 430

CGG CCC CTC GCC CAG GTC CTC GCC CAC ATG GAG GCC ACG GGG GTG CGG     1344
Arg Pro Leu Ala Gln Val Leu Ala His Met Glu Ala Thr Gly Val Arg
        435                 440                 445

CTG GAT GTG CCC TAC CTG GAG GCC CTT TCC CAG GAG GTG GCC TTT GAG     1392
Leu Asp Val Pro Tyr Leu Glu Ala Leu Ser Gln Glu Val Ala Phe Glu
    450                 455                 460
```

-continued

```
CTG GAG CGC CTC GAG GCC GAG GTC CAC CGC CTG GCG GGC CAC CCC TTC     1440
Leu Glu Arg Leu Glu Ala Glu Val His Arg Leu Ala Gly His Pro Phe
465                 470                 475                 480

AAC CTG AAC TCT AGG GAC CAG CTG GAG CGG GTC CTC TTT GAC GAG CTC     1488
Asn Leu Asn Ser Arg Asp Gln Leu Glu Arg Val Leu Phe Asp Glu Leu
                485                 490                 495

GGC CTA CCC CCC ATC GGC AAG ACG GAG AAG ACG GGC AAG CGC TCC ACC     1536
Gly Leu Pro Pro Ile Gly Lys Thr Glu Lys Thr Gly Lys Arg Ser Thr
            500                 505                 510

AGC GCC GCC GTC CTG GAG CTC TTA AGG GAG GCC CAC CCC ATC GTG GGG     1584
Ser Ala Ala Val Leu Glu Leu Leu Arg Glu Ala His Pro Ile Val Gly
        515                 520                 525

CGG ATC CTG GAG TAC CGG GAG CTC ATG AAG CTC AAG AGC ACC TAC ATA     1632
Arg Ile Leu Glu Tyr Arg Glu Leu Met Lys Leu Lys Ser Thr Tyr Ile
    530                 535                 540

GAC CCC CTC CCC AGG CTG GTC CAC CCC AAA ACC GGC CGG CTC CAC ACC     1680
Asp Pro Leu Pro Arg Leu Val His Pro Lys Thr Gly Arg Leu His Thr
545                 550                 555                 560

CGC TTC AAC CAG ACG GCC ACC GCC ACG GGC CGC CTC TCC AGC TCC GAC     1728
Arg Phe Asn Gln Thr Ala Thr Ala Thr Gly Arg Leu Ser Ser Ser Asp
                565                 570                 575

CCC AAC CTG CAG AAC ATC CCC GTG CGC ACC CCC TTA GGC CAG CGC ATC     1776
Pro Asn Leu Gln Asn Ile Pro Val Arg Thr Pro Leu Gly Gln Arg Ile
            580                 585                 590

CGC AAG GCC TTC ATT GCC GAG GAG GGC CAT CTC CTG GTG GCC CTG GAC     1824
Arg Lys Ala Phe Ile Ala Glu Glu Gly His Leu Leu Val Ala Leu Asp
        595                 600                 605

TAT AGC CAG ATC GAG CTC CGG GTC CTC GCC CAC CTC TCG GGG GAC GAG     1872
Tyr Ser Gln Ile Glu Leu Arg Val Leu Ala His Leu Ser Gly Asp Glu
    610                 615                 620

AAC CTC ATC CGG GTC TTC CGG GAA GGG AAG GAC ATC CAC ACC GAG ACC     1920
Asn Leu Ile Arg Val Phe Arg Glu Gly Lys Asp Ile His Thr Glu Thr
625                 630                 635                 640

GCC GCC TGG ATG TTC GGC GTG CCC CCC GAG GGG GTG GAC GGG GCC ATG     1968
Ala Ala Trp Met Phe Gly Val Pro Pro Glu Gly Val Asp Gly Ala Met
                645                 650                 655

CGC CGG GCG GCC AAG ACG GTG AAC TTC GGG GTG CTC TAC GGG ATG TCC     2016
Arg Arg Ala Ala Lys Thr Val Asn Phe Gly Val Leu Tyr Gly Met Ser
            660                 665                 670

GCC CAC CGC CTC TCC CAG GAG CTC TCC ATC CCC TAC GAG GAG GCG GCG     2064
Ala His Arg Leu Ser Gln Glu Leu Ser Ile Pro Tyr Glu Glu Ala Ala
        675                 680                 685

GCC TTC ATC GAG CGC TAC TTC CAG AGC TTC CCC AAG GTG CGG GCC TGG     2112
Ala Phe Ile Glu Arg Tyr Phe Gln Ser Phe Pro Lys Val Arg Ala Trp
    690                 695                 700

ATC GCC AAA ACC TTG GAG GAG GGG CGG AAG AAG GGG TAC GTG GAG ACC     2160
Ile Ala Lys Thr Leu Glu Glu Gly Arg Lys Lys Gly Tyr Val Glu Thr
705                 710                 715                 720

CTC TTC GGC CGC CGC CGC TAC GTG CCC GAC CTC AAC GCC CGG GTG AAG     2208
Leu Phe Gly Arg Arg Arg Tyr Val Pro Asp Leu Asn Ala Arg Val Lys
                725                 730                 735

AGC GTG CGG GAG GCG GCG GAG CGC ATG GCC TTC AAC ATG CCC GTG CAG     2256
Ser Val Arg Glu Ala Ala Glu Arg Met Ala Phe Asn Met Pro Val Gln
            740                 745                 750

GGC ACC GCC GCG GAC CTC ATG AAG CTG GCC ATG GTG AAG CTC TTC CCC     2304
Gly Thr Ala Ala Asp Leu Met Lys Leu Ala Met Val Lys Leu Phe Pro
        755                 760                 765

AGG CTC AGG CCC TTG GGC GTT CGC ATC CTC CTC CAG GTG CAC GAC GAG     2352
Arg Leu Arg Pro Leu Gly Val Arg Ile Leu Leu Gln Val His Asp Glu
    770                 775                 780
```

-continued

CTG GTC TTG GAG GCC CCA AAG GCG CGG GCG GAG GAG GCC GCC CAG TTG 2400
Leu Val Leu Glu Ala Pro Lys Ala Arg Ala Glu Glu Ala Ala Gln Leu
785 790 795 800

GCC AAG GAG ACC ATG GAA GGG GTT TAC CCC CTC TCC GTC CCC CTG GAG 2448
Ala Lys Glu Thr Met Glu Gly Val Tyr Pro Leu Ser Val Pro Leu Glu
805 810 815

GTG GAG GTG GGG ATG GGG GAG GAC TGG CTT TCC GCC AAG GCC 2490
Val Glu Val Gly Met Gly Glu Asp Trp Leu Ser Ala Lys Ala
820 825 830

TAG 2493

( 2 ) INFORMATION FOR SEQ ID NO:6:

( i ) SEQUENCE CHARACTERISTICS:
( A ) LENGTH: 830 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Leu Pro Leu Phe Glu Pro Lys Gly Arg Val Leu Leu Val Asp Gly
1 5 10 15

His His Leu Ala Tyr Arg Thr Phe Phe Ala Leu Lys Gly Leu Thr Thr
20 25 30

Ser Arg Gly Glu Pro Val Gln Ala Val Tyr Gly Phe Ala Lys Ser Leu
35 40 45

Leu Lys Ala Leu Lys Glu Asp Gly Glu Val Ala Ile Val Val Phe Asp
50 55 60

Ala Lys Ala Pro Ser Phe Arg His Glu Ala Tyr Glu Ala Tyr Lys Ala
65 70 75 80

Gly Arg Ala Pro Thr Pro Glu Asp Phe Pro Arg Gln Leu Ala Leu Ile
85 90 95

Lys Glu Leu Val Asp Leu Leu Gly Leu Val Arg Leu Glu Val Pro Gly
100 105 110

Phe Glu Ala Asp Asp Val Leu Ala Thr Leu Ala Lys Lys Ala Glu Arg
115 120 125

Glu Gly Tyr Glu Val Arg Ile Leu Ser Ala Asp Arg Asp Leu Tyr Gln
130 135 140

Leu Leu Ser Asp Arg Ile His Leu Leu His Pro Glu Gly Glu Val Leu
145 150 155 160

Thr Pro Gly Trp Leu Gln Glu Arg Tyr Gly Leu Ser Pro Glu Arg Trp
165 170 175

Val Glu Tyr Arg Ala Leu Val Gly Asp Pro Ser Asp Asn Leu Pro Gly
180 185 190

Val Pro Gly Ile Gly Glu Lys Thr Ala Leu Lys Leu Leu Lys Glu Trp
195 200 205

Gly Ser Leu Glu Ala Ile Leu Lys Asn Leu Asp Gln Val Lys Pro Glu
210 215 220

Arg Val Arg Glu Ala Ile Arg Asn Asn Leu Asp Lys Leu Gln Met Ser
225 230 235 240

Leu Glu Leu Ser Arg Leu Arg Thr Asp Leu Pro Leu Glu Val Asp Phe
245 250 255

Ala Lys Arg Arg Glu Pro Asp Trp Glu Gly Leu Lys Ala Phe Leu Glu
260 265 270

Arg Leu Glu Phe Gly Ser Leu Leu His Glu Phe Gly Leu Leu Glu Ala
275 280 285

-continued

```
Pro Lys Glu Ala Glu Glu Ala Pro Trp Pro Pro Pro Gly Gly Ala Phe
    290                 295                 300

Leu Gly Phe Leu Leu Ser Arg Pro Glu Pro Met Trp Ala Glu Leu Leu
305                 310                 315                 320

Ala Leu Ala Gly Ala Lys Glu Gly Arg Val His Arg Ala Glu Asp Pro
                325                 330                 335

Val Gly Ala Leu Lys Asp Leu Lys Glu Ile Arg Gly Leu Leu Ala Lys
            340                 345                 350

Asp Leu Ser Val Leu Ala Leu Arg Glu Gly Arg Glu Ile Pro Pro Gly
        355                 360                 365

Asp Asp Pro Met Leu Leu Ala Tyr Leu Leu Asp Pro Gly Asn Thr Asn
    370                 375                 380

Pro Glu Gly Val Ala Arg Arg Tyr Gly Gly Glu Trp Lys Glu Asp Ala
385                 390                 395                 400

Ala Ala Arg Ala Leu Leu Ser Glu Arg Leu Trp Gln Ala Leu Tyr Pro
                405                 410                 415

Arg Val Ala Glu Glu Glu Arg Leu Leu Trp Leu Tyr Arg Glu Val Glu
            420                 425                 430

Arg Pro Leu Ala Gln Val Leu Ala His Met Glu Ala Thr Gly Val Arg
        435                 440                 445

Leu Asp Val Pro Tyr Leu Glu Ala Leu Ser Gln Glu Val Ala Phe Glu
    450                 455                 460

Leu Glu Arg Leu Glu Ala Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510

Ser Ala Ala Val Leu Glu Leu Leu Arg Glu Ala His Pro Ile Val Gly
        515                 520                 525

Arg Ile Leu Glu Tyr Arg Glu Leu Met Lys Leu Lys Ser Thr Tyr Ile
    530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590

Arg Lys Ala Phe Ile Ala Glu Glu Gly His Leu Leu Val Ala Leu Asp
        595                 600                 605

Tyr Ser Gln Ile Glu Leu Arg Val Leu Ala His Leu Ser Gly Asp Glu
    610                 615                 620

Asn Leu Ile Arg Val Phe Arg Glu Gly Lys Asp Ile His Thr Glu Thr
625                 630                 635                 640

Ala Ala Trp Met Phe Gly Val Pro Pro Glu Gly Val Asp Gly Ala Met
                645                 650                 655

Arg Arg Ala Ala Lys Thr Val Asn Phe Gly Val Leu Tyr Gly Met Ser
            660                 665                 670

Ala His Arg Leu Ser Gln Glu Leu Ser Ile Pro Tyr Glu Glu Ala Ala
        675                 680                 685

Ala Phe Ile Glu Arg Tyr Phe Gln Ser Phe Pro Lys Val Arg Ala Trp
    690                 695                 700

Ile Ala Lys Thr Leu Glu Glu Gly Arg Lys Lys Gly Tyr Val Glu Thr
705                 710                 715                 720
```

-continued

Leu Phe Gly Arg Arg Arg Tyr Val Pro Asp Leu Asn Ala Arg Val Lys
725 730 735

Ser Val Arg Glu Ala Ala Glu Arg Met Ala Phe Asn Met Pro Val Gln
740 745 750

Gly Thr Ala Ala Asp Leu Met Lys Leu Ala Met Val Lys Leu Phe Pro
755 760 765

Arg Leu Arg Pro Leu Gly Val Arg Ile Leu Leu Gln Val His Asp Glu
770 775 780

Leu Val Leu Glu Ala Pro Lys Ala Arg Ala Glu Glu Ala Ala Gln Leu
785 790 795 800

Ala Lys Glu Thr Met Glu Gly Val Tyr Pro Leu Ser Val Pro Leu Glu
805 810 815

Val Glu Val Gly Met Gly Glu Asp Trp Leu Ser Ala Lys Ala
820 825 830

( 2 ) INFORMATION FOR SEQ ID NO:7:

( i ) SEQUENCE CHARACTERISTICS:
( A ) LENGTH: 2505 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Thermus species Z05

( i x ) FEATURE:
( A ) NAME/KEY: CDS
( B ) LOCATION: 1..2502

( x i ) SEQUENCE DESCRIPTION: SEQ ID NO:7:

ATG AAG GCG ATG CTT CCG CTC TTT GAA CCC AAA GGC CGG GTT CTC CTG 48
Met Lys Ala Met Leu Pro Leu Phe Glu Pro Lys Gly Arg Val Leu Leu
1 5 10 15

GTG GAC GGC CAC CAC CTG GCC TAC CGC ACC TTC TTC GCC CTA AAG GGC 96
Val Asp Gly His His Leu Ala Tyr Arg Thr Phe Phe Ala Leu Lys Gly
20 25 30

CTC ACC ACG AGC CGG GGC GAA CCG GTG CAG GCG GTT TAC GGC TTC GCC 144
Leu Thr Thr Ser Arg Gly Glu Pro Val Gln Ala Val Tyr Gly Phe Ala
35 40 45

AAG AGC CTC CTC AAG GCC CTG AAG GAG GAC GGG TAC AAG GCC GTC TTC 192
Lys Ser Leu Leu Lys Ala Leu Lys Glu Asp Gly Tyr Lys Ala Val Phe
50 55 60

GTG GTC TTT GAC GCC AAG GCC CCT TCC TTC CGC CAC GAG GCC TAC GAG 240
Val Val Phe Asp Ala Lys Ala Pro Ser Phe Arg His Glu Ala Tyr Glu
65 70 75 80

GCC TAC AAG GCA GGC CGC GCC CCG ACC CCC GAG GAC TTC CCC CGG CAG 288
Ala Tyr Lys Ala Gly Arg Ala Pro Thr Pro Glu Asp Phe Pro Arg Gln
85 90 95

CTC GCC CTC ATC AAG GAG CTG GTG GAC CTC CTG GGG TTT ACT CGC CTC 336
Leu Ala Leu Ile Lys Glu Leu Val Asp Leu Leu Gly Phe Thr Arg Leu
100 105 110

GAG GTT CCG GGC TTT GAG GCG GAC GAC GTC CTC GCC ACC CTG GCC AAG 384
Glu Val Pro Gly Phe Glu Ala Asp Asp Val Leu Ala Thr Leu Ala Lys
115 120 125

AAG GCG GAA AGG GAG GGG TAC GAG GTG CGC ATC CTC ACC GCC GAC CGG 432
Lys Ala Glu Arg Glu Gly Tyr Glu Val Arg Ile Leu Thr Ala Asp Arg

-continued 130 135 140

GAC CTT TAC CAG CTC GTC TCC GAC CGC GTC GCC GTC CTC CAC CCC GAG 480
Asp Leu Tyr Gln Leu Val Ser Asp Arg Val Ala Val Leu His Pro Glu
145 150 155 160

GGC CAC CTC ATC ACC CCG GAG TGG CTT TGG GAG AAG TAC GGC CTT AAG 528
Gly His Leu Ile Thr Pro Glu Trp Leu Trp Glu Lys Tyr Gly Leu Lys
165 170 175

CCG GAG CAG TGG GTG GAC TTC CGC GCC CTC GTG GGG GAC CCC TCC GAC 576
Pro Glu Gln Trp Val Asp Phe Arg Ala Leu Val Gly Asp Pro Ser Asp
180 185 190

AAC CTC CCC GGG GTC AAG GGC ATC GGG GAG AAG ACC GCC CTC AAG CTC 624
Asn Leu Pro Gly Val Lys Gly Ile Gly Glu Lys Thr Ala Leu Lys Leu
195 200 205

CTC AAG GAG TGG GGA AGC CTG GAA AAT ATC CTC AAG AAC CTG GAC CGG 672
Leu Lys Glu Trp Gly Ser Leu Glu Asn Ile Leu Lys Asn Leu Asp Arg
210 215 220

GTG AAG CCG GAA AGC GTC CGG GAA AGG ATC AAG GCC CAC CTG GAA GAC 720
Val Lys Pro Glu Ser Val Arg Glu Arg Ile Lys Ala His Leu Glu Asp
225 230 235 240

CTT AAG CTC TCC TTG GAG CTT TCC CGG GTG CGC TCG GAC CTC CCC CTG 768
Leu Lys Leu Ser Leu Glu Leu Ser Arg Val Arg Ser Asp Leu Pro Leu
245 250 255

GAG GTG GAC TTC GCC CGG AGG CGG GAG CCT GAC CGG GAA GGG CTT CGG 816
Glu Val Asp Phe Ala Arg Arg Arg Glu Pro Asp Arg Glu Gly Leu Arg
260 265 270

GCC TTT TTG GAG CGC TTG GAG TTC GGC AGC CTC CTC CAC GAG TTC GGC 864
Ala Phe Leu Glu Arg Leu Glu Phe Gly Ser Leu Leu His Glu Phe Gly
275 280 285

CTC CTC GAG GCC CCC GCC CCC CTG GAG GAG GCC CCC TGG CCC CCG CCG 912
Leu Leu Glu Ala Pro Ala Pro Leu Glu Glu Ala Pro Trp Pro Pro Pro
290 295 300

GAA GGG GCC TTC GTG GGC TTC GTC CTC TCC CGC CCC GAG CCC ATG TGG 960
Glu Gly Ala Phe Val Gly Phe Val Leu Ser Arg Pro Glu Pro Met Trp
305 310 315 320

GCG GAG CTT AAA GCC CTG GCC GCC TGC AAG GAG GGC CGG GTG CAC CGG 1008
Ala Glu Leu Lys Ala Leu Ala Ala Cys Lys Glu Gly Arg Val His Arg
325 330 335

GCA AAG GAC CCC TTG GCG GGG CTA AAG GAC CTC AAG GAG GTC CGA GGC 1056
Ala Lys Asp Pro Leu Ala Gly Leu Lys Asp Leu Lys Glu Val Arg Gly
340 345 350

CTC CTC GCC AAG GAC CTC GCC GTT TTG GCC CTT CGC GAG GGG CTG GAC 1104
Leu Leu Ala Lys Asp Leu Ala Val Leu Ala Leu Arg Glu Gly Leu Asp
355 360 365

CTC GCG CCT TCG GAC GAC CCC ATG CTC CTC GCC TAC CTC CTG GAC CCC 1152
Leu Ala Pro Ser Asp Asp Pro Met Leu Leu Ala Tyr Leu Leu Asp Pro
370 375 380

TCC AAC ACC ACC CCC GAG GGG GTG GCC CGG CGC TAC GGG GGG GAG TGG 1200
Ser Asn Thr Thr Pro Glu Gly Val Ala Arg Arg Tyr Gly Gly Glu Trp
385 390 395 400

ACG GAG GAC GCC GCC CAC CGG GCC CTC CTC GCC GAG CGG CTC CAG CAA 1248
Thr Glu Asp Ala Ala His Arg Ala Leu Leu Ala Glu Arg Leu Gln Gln
405 410 415

AAC CTC TTG GAA CGC CTC AAG GGA GAG GAA AAG CTC CTT TGG CTC TAC 1296
Asn Leu Leu Glu Arg Leu Lys Gly Glu Glu Lys Leu Leu Trp Leu Tyr
420 425 430

CAA GAG GTG GAA AAG CCC CTC TCC CGG GTC CTG GCC CAC ATG GAG GCC 1344
Gln Glu Val Glu Lys Pro Leu Ser Arg Val Leu Ala His Met Glu Ala
435 440 445

ACC GGG GTA AGG CTG GAC GTG GCC TAT CTA AAG GCC CTT TCC CTG GAG 1392
Thr Gly Val Arg Leu Asp Val Ala Tyr Leu Lys Ala Leu Ser Leu Glu

-continued

```
        450                     455                     460

CTT GCG GAG GAG ATT CGC CGC CTC GAG GAG GAG GTC TTC CGC CTG GCG     1440
Leu Ala Glu Glu Ile Arg Arg Leu Glu Glu Glu Val Phe Arg Leu Ala
465                 470                     475                 480

GGC CAC CCC TTC AAC CTG AAC TCC CGT GAC CAG CTA GAG CGG GTG CTC     1488
Gly His Pro Phe Asn Leu Asn Ser Arg Asp Gln Leu Glu Arg Val Leu
                485                     490                 495

TTT GAC GAG CTT AGG CTT CCC GCC CTG GGC AAG ACG CAA AAG ACG GGG     1536
Phe Asp Glu Leu Arg Leu Pro Ala Leu Gly Lys Thr Gln Lys Thr Gly
            500                     505                 510

AAG CGC TCC ACC AGC GCC GCG GTG CTG GAG GCC CTC AGG GAG GCC CAC     1584
Lys Arg Ser Thr Ser Ala Ala Val Leu Glu Ala Leu Arg Glu Ala His
        515                     520                 525

CCC ATC GTG GAG AAG ATC CTC CAG CAC CGG GAG CTC ACC AAG CTC AAG     1632
Pro Ile Val Glu Lys Ile Leu Gln His Arg Glu Leu Thr Lys Leu Lys
    530                     535                 540

AAC ACC TAC GTG GAC CCC CTC CCG GGC CTC GTC CAC CCG AGG ACG GGC     1680
Asn Thr Tyr Val Asp Pro Leu Pro Gly Leu Val His Pro Arg Thr Gly
545                 550                     555                 560

CGC CTC CAC ACC CGC TTC AAC CAG ACA GCC ACG GCC ACG GGA AGG CTC     1728
Arg Leu His Thr Arg Phe Asn Gln Thr Ala Thr Ala Thr Gly Arg Leu
                565                     570                 575

TCT AGC TCC GAC CCC AAC CTG CAG AAC ATC CCC ATC CGC ACC CCC TTG     1776
Ser Ser Ser Asp Pro Asn Leu Gln Asn Ile Pro Ile Arg Thr Pro Leu
            580                     585                 590

GGC CAG AGG ATC CGC CGG GCC TTC GTG GCC GAG GCG GGA TGG GCG TTG     1824
Gly Gln Arg Ile Arg Arg Ala Phe Val Ala Glu Ala Gly Trp Ala Leu
        595                     600                 605

GTG GCC CTG GAC TAT AGC CAG ATA GAG CTC CGG GTC CTC GCC CAC CTC     1872
Val Ala Leu Asp Tyr Ser Gln Ile Glu Leu Arg Val Leu Ala His Leu
    610                     615                 620

TCC GGG GAC GAG AAC CTG ATC AGG GTC TTC CAG GAG GGG AAG GAC ATC     1920
Ser Gly Asp Glu Asn Leu Ile Arg Val Phe Gln Glu Gly Lys Asp Ile
625                 630                     635                 640

CAC ACC CAG ACC GCA AGC TGG ATG TTC GGC GTC TCC CCG GAG GCC GTG     1968
His Thr Gln Thr Ala Ser Trp Met Phe Gly Val Ser Pro Glu Ala Val
                645                     650                 655

GAC CCC CTG ATG CGC CGG GCG GCC AAG ACG GTG AAC TTC GGC GTC CTC     2016
Asp Pro Leu Met Arg Arg Ala Ala Lys Thr Val Asn Phe Gly Val Leu
            660                     665                 670

TAC GGC ATG TCC GCC CAT AGG CTC TCC CAG GAG CTT GCC ATC CCC TAC     2064
Tyr Gly Met Ser Ala His Arg Leu Ser Gln Glu Leu Ala Ile Pro Tyr
        675                     680                 685

GAG GAG GCG GTG GCC TTT ATA GAG CGC TAC TTC CAA AGC TTC CCC AAG     2112
Glu Glu Ala Val Ala Phe Ile Glu Arg Tyr Phe Gln Ser Phe Pro Lys
    690                     695                 700

GTG CGG GCC TGG ATA GAA AAG ACC CTG GAG GAG GGG AGG AAG CGG GGC     2160
Val Arg Ala Trp Ile Glu Lys Thr Leu Glu Glu Gly Arg Lys Arg Gly
705                 710                     715                 720

TAC GTG GAA ACC CTC TTC GGA AGA AGG CGC TAC GTG CCC GAC CTC AAC     2208
Tyr Val Glu Thr Leu Phe Gly Arg Arg Arg Tyr Val Pro Asp Leu Asn
                725                     730                 735

GCC CGG GTG AAG AGC GTC AGG GAG GCC GCG GAG CGC ATG GCC TTC AAC     2256
Ala Arg Val Lys Ser Val Arg Glu Ala Ala Glu Arg Met Ala Phe Asn
            740                     745                 750

ATG CCC GTC CAG GGC ACC GCC GCC GAC CTC ATG AAG CTC GCC ATG GTG     2304
Met Pro Val Gln Gly Thr Ala Ala Asp Leu Met Lys Leu Ala Met Val
        755                     760                 765

AAG CTC TTC CCC CAC CTC CGG GAG ATG GGG GCC CGC ATG CTC CTC CAG     2352
Lys Leu Phe Pro His Leu Arg Glu Met Gly Ala Arg Met Leu Leu Gln
```

-continued

```
              770                                       775                                       780

GTC CAC GAC GAG CTC CTC CTG GAG GCC CCC CAA GCG CGG GCC GAG GAG     2400
Val His Asp Glu Leu Leu Leu Glu Ala Pro Gln Ala Arg Ala Glu Glu
785                     790                     795                 800

GTG GCG GCT TTG GCC AAG GAG GCC ATG GAG AAG GCC TAT CCC CTC GCC     2448
Val Ala Ala Leu Ala Lys Glu Ala Met Glu Lys Ala Tyr Pro Leu Ala
                805                     810                     815

GTG CCC CTG GAG GTG GAG GTG GGG ATC GGG GAG GAC TGG CTT TCC GCC     2496
Val Pro Leu Glu Val Glu Val Gly Ile Gly Glu Asp Trp Leu Ser Ala
            820                     825                     830

AAG GGC TGA                                                         2505
Lys Gly
```

( 2 ) INFORMATION FOR SEQ ID NO:8:

( i ) SEQUENCE CHARACTERISTICS:
( A ) LENGTH: 834 amino acids
( B ) TYPE: amino acid
( D ) TOPOLOGY: linear ( i i ) MOLECULE TYPE: protein ( x i ) SEQUENCE DESCRIPTION: SEQ ID NO:8:

```
Met Lys Ala Met Leu Pro Leu Phe Glu Pro Lys Gly Arg Val Leu Leu
  1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270
```

-continued

```
Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Lys Glu Gly Arg Val His Arg
                325                 330                 335

Ala Lys Asp Pro Leu Ala Gly Leu Lys Asp Leu Lys Glu Val Arg Gly
            340                 345                 350

Leu Leu Ala Lys Asp Leu Ala Val Leu Ala Leu Arg Glu Gly Leu Asp
        355                 360                 365

Leu Ala Pro Ser Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ala Glu Arg Leu Gln Gln
                405                 410                 415

Asn Leu Leu Glu Arg Leu Lys Gly Glu Glu Lys Leu Leu Trp Leu Tyr
            420                 425                 430

Gln Glu Val Glu Lys Pro Leu Ser Arg Val Leu Ala His Met Glu Ala
        435                 440                 445

Thr Gly Val Arg Leu Asp Val Ala Tyr Leu Lys Ala Leu Ser Leu Glu
    450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Gly Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Ile Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Ser Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700
```

Val Arg Ala Trp Ile Glu Lys Thr Leu Glu Glu Gly Arg Lys Arg Gly
705 710 715 720

Tyr Val Glu Thr Leu Phe Gly Arg Arg Arg Tyr Val Pro Asp Leu Asn
725 730 735

Ala Arg Val Lys Ser Val Arg Glu Ala Ala Glu Arg Met Ala Phe Asn
740 745 750

Met Pro Val Gln Gly Thr Ala Ala Asp Leu Met Lys Leu Ala Met Val
755 760 765

Lys Leu Phe Pro His Leu Arg Glu Met Gly Ala Arg Met Leu Leu Gln
770 775 780

Val His Asp Glu Leu Leu Leu Glu Ala Pro Gln Ala Arg Ala Glu Glu
785 790 795 800

Val Ala Ala Leu Ala Lys Glu Ala Met Glu Lys Ala Tyr Pro Leu Ala
805 810 815

Val Pro Leu Glu Val Glu Val Gly Ile Gly Glu Asp Trp Leu Ser Ala
820 825 830

Lys Gly ( 2 ) INFORMATION FOR SEQ ID NO:9:

( i ) SEQUENCE CHARACTERISTICS:
( A ) LENGTH: 2505 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Thermus thermophilus ( i x ) FEATURE:
( A ) NAME/KEY: CDS
( B ) LOCATION: 1..2502

( x i ) SEQUENCE DESCRIPTION: SEQ ID NO:9:

ATG GAG GCG ATG CTT CCG CTC TTT GAA CCC AAA GGC CGG GTC CTC CTG 48
Met Glu Ala Met Leu Pro Leu Phe Glu Pro Lys Gly Arg Val Leu Leu
1 5 10 15

GTG GAC GGC CAC CAC CTG GCC TAC CGC ACC TTC TTC GCC CTG AAG GGC 96
Val Asp Gly His His Leu Ala Tyr Arg Thr Phe Phe Ala Leu Lys Gly
20 25 30

CTC ACC ACG AGC CGG GGC GAA CCG GTG CAG GCG GTC TAC GGC TTC GCC 144
Leu Thr Thr Ser Arg Gly Glu Pro Val Gln Ala Val Tyr Gly Phe Ala
35 40 45

AAG AGC CTC CTC AAG GCC CTG AAG GAG GAC GGG TAC AAG GCC GTC TTC 192
Lys Ser Leu Leu Lys Ala Leu Lys Glu Asp Gly Tyr Lys Ala Val Phe
50 55 60

GTG GTC TTT GAC GCC AAG GCC CCC TCC TTC CGC CAC GAG GCC TAC GAG 240
Val Val Phe Asp Ala Lys Ala Pro Ser Phe Arg His Glu Ala Tyr Glu
65 70 75 80

GCC TAC AAG GCG GGG AGG GCC CCG ACC CCC GAG GAC TTC CCC CGG CAG 288
Ala Tyr Lys Ala Gly Arg Ala Pro Thr Pro Glu Asp Phe Pro Arg Gln
85 90 95

CTC GCC CTC ATC AAG GAG CTG GTG GAC CTC CTG GGG TTT ACC CGC CTC 336
Leu Ala Leu Ile Lys Glu Leu Val Asp Leu Leu Gly Phe Thr Arg Leu
100 105 110

GAG GTC CCC GGC TAC GAG GCG GAC GAC GTT CTC GCC ACC CTG GCC AAG 384

-continued

Glu Val Pro Gly Tyr Glu Ala Asp Asp Val Leu Ala Thr Leu Ala Lys
115 120 125

AAG GCG GAA AAG GAG GGG TAC GAG GTG CGC ATC CTC ACC GCC GAC CGC 432
Lys Ala Glu Lys Glu Gly Tyr Glu Val Arg Ile Leu Thr Ala Asp Arg
130 135 140

GAC CTC TAC CAA CTC GTC TCC GAC CGC GTC GCC GTC CTC CAC CCC GAG 480
Asp Leu Tyr Gln Leu Val Ser Asp Arg Val Ala Val Leu His Pro Glu
145 150 155 160

GGC CAC CTC ATC ACC CCG GAG TGG CTT TGG GAG AAG TAC GGC CTC AGG 528
Gly His Leu Ile Thr Pro Glu Trp Leu Trp Glu Lys Tyr Gly Leu Arg
165 170 175

CCG GAG CAG TGG GTG GAC TTC CGC GCC CTC GTG GGG GAC CCC TCC GAC 576
Pro Glu Gln Trp Val Asp Phe Arg Ala Leu Val Gly Asp Pro Ser Asp
180 185 190

AAC CTC CCC GGG GTC AAG GGC ATC GGG GAG AAG ACC GCC CTC AAG CTC 624
Asn Leu Pro Gly Val Lys Gly Ile Gly Glu Lys Thr Ala Leu Lys Leu
195 200 205

CTC AAG GAG TGG GGA AGC CTG GAA AAC CTC CTC AAG AAC CTG GAC CGG 672
Leu Lys Glu Trp Gly Ser Leu Glu Asn Leu Leu Lys Asn Leu Asp Arg
210 215 220

GTA AAG CCA GAA AAC GTC CGG GAG AAG ATC AAG GCC CAC CTG GAA GAC 720
Val Lys Pro Glu Asn Val Arg Glu Lys Ile Lys Ala His Leu Glu Asp
225 230 235 240

CTC AGG CTC TCC TTG GAG CTC TCC CGG GTG CGC ACC GAC CTC CCC CTG 768
Leu Arg Leu Ser Leu Glu Leu Ser Arg Val Arg Thr Asp Leu Pro Leu
245 250 255

GAG GTG GAC CTC GCC CAG GGG CGG GAG CCC GAC CGG GAG GGG CTT AGG 816
Glu Val Asp Leu Ala Gln Gly Arg Glu Pro Asp Arg Glu Gly Leu Arg
260 265 270

GCC TTC CTG GAG AGG CTG GAG TTC GGC AGC CTC CTC CAC GAG TTC GGC 864
Ala Phe Leu Glu Arg Leu Glu Phe Gly Ser Leu Leu His Glu Phe Gly
275 280 285

CTC CTG GAG GCC CCC GCC CCC CTG GAG GAG GCC CCC TGG CCC CCG CCG 912
Leu Leu Glu Ala Pro Ala Pro Leu Glu Glu Ala Pro Trp Pro Pro Pro
290 295 300

GAA GGG GCC TTC GTG GGC TTC GTC CTC TCC CGC CCC GAG CCC ATG TGG 960
Glu Gly Ala Phe Val Gly Phe Val Leu Ser Arg Pro Glu Pro Met Trp
305 310 315 320

GCG GAG CTT AAA GCC CTG GCC GCC TGC AGG GAC GGC CGG GTG CAC CGG 1008
Ala Glu Leu Lys Ala Leu Ala Ala Cys Arg Asp Gly Arg Val His Arg
325 330 335

GCA GCA GAC CCC TTG GCG GGG CTA AAG GAC CTC AAG GAG GTC CGG GGC 1056
Ala Ala Asp Pro Leu Ala Gly Leu Lys Asp Leu Lys Glu Val Arg Gly
340 345 350

CTC CTC GCC AAG GAC CTC GCC GTC TTG GCC TCG AGG GAG GGG CTA GAC 1104
Leu Leu Ala Lys Asp Leu Ala Val Leu Ala Ser Arg Glu Gly Leu Asp
355 360 365

CTC GTG CCC GGG GAC GAC CCC ATG CTC CTC GCC TAC CTC CTG GAC CCC 1152
Leu Val Pro Gly Asp Asp Pro Met Leu Leu Ala Tyr Leu Leu Asp Pro
370 375 380

TCC AAC ACC ACC CCC GAG GGG GTG GCG CGG CGC TAC GGG GGG GAG TGG 1200
Ser Asn Thr Thr Pro Glu Gly Val Ala Arg Arg Tyr Gly Gly Glu Trp
385 390 395 400

ACG GAG GAC GCC GCC CAC CGG GCC CTC CTC TCG GAG AGG CTC CAT CGG 1248
Thr Glu Asp Ala Ala His Arg Ala Leu Leu Ser Glu Arg Leu His Arg
405 410 415

AAC CTC CTT AAG CGC CTC GAG GGG GAG GAG AAG CTC CTT TGG CTC TAC 1296
Asn Leu Leu Lys Arg Leu Glu Gly Glu Glu Lys Leu Leu Trp Leu Tyr
420 425 430

CAC GAG GTG GAA AAG CCC CTC TCC CGG GTC CTG GCC CAC ATG GAG GCC 1344

-continued

```
His Glu Val Glu Lys Pro Leu Ser Arg Val Leu Ala His Met Glu Ala
        435                 440                 445

ACC GGG GTA CGG CTG GAC GTG GCC TAC CTT CAG GCC CTT TCC CTG GAG     1392
Thr Gly Val Arg Leu Asp Val Ala Tyr Leu Gln Ala Leu Ser Leu Glu
    450                 455                 460

CTT GCG GAG GAG ATC CGC CGC CTC GAG GAG GAG GTC TTC CGC TTG GCG     1440
Leu Ala Glu Glu Ile Arg Arg Leu Glu Glu Glu Val Phe Arg Leu Ala
465                 470                 475                 480

GGC CAC CCC TTC AAC CTC AAC TCC CGG GAC CAG CTG GAA AGG GTG CTC     1488
Gly His Pro Phe Asn Leu Asn Ser Arg Asp Gln Leu Glu Arg Val Leu
                485                 490                 495

TTT GAC GAG CTT AGG CTT CCC GCC TTG GGG AAG ACG CAA AAG ACA GGC     1536
Phe Asp Glu Leu Arg Leu Pro Ala Leu Gly Lys Thr Gln Lys Thr Gly
            500                 505                 510

AAG CGC TCC ACC AGC GCC GCG GTG CTG GAG GCC CTA CGG GAG GCC CAC     1584
Lys Arg Ser Thr Ser Ala Ala Val Leu Glu Ala Leu Arg Glu Ala His
        515                 520                 525

CCC ATC GTG GAG AAG ATC CTC CAG CAC CGG GAG CTC ACC AAG CTC AAG     1632
Pro Ile Val Glu Lys Ile Leu Gln His Arg Glu Leu Thr Lys Leu Lys
    530                 535                 540

AAC ACC TAC GTG GAC CCC CTC CCA AGC CTC GTC CAC CCG AGG ACG GGC     1680
Asn Thr Tyr Val Asp Pro Leu Pro Ser Leu Val His Pro Arg Thr Gly
545                 550                 555                 560

CGC CTC CAC ACC CGC TTC AAC CAG ACG GCC ACG GCC ACG GGG AGG CTT     1728
Arg Leu His Thr Arg Phe Asn Gln Thr Ala Thr Ala Thr Gly Arg Leu
                565                 570                 575

AGT AGC TCC GAC CCC AAC CTG CAG AAC ATC CCC GTC CGC ACC CCC TTG     1776
Ser Ser Ser Asp Pro Asn Leu Gln Asn Ile Pro Val Arg Thr Pro Leu
            580                 585                 590

GGC CAG AGG ATC CGC CGG GCC TTC GTG GCC GAG GCG GGT TGG GCG TTG     1824
Gly Gln Arg Ile Arg Arg Ala Phe Val Ala Glu Ala Gly Trp Ala Leu
        595                 600                 605

GTG GCC CTG GAC TAT AGC CAG ATA GAG CTC CGC GTC CTC GCC CAC CTC     1872
Val Ala Leu Asp Tyr Ser Gln Ile Glu Leu Arg Val Leu Ala His Leu
    610                 615                 620

TCC GGG GAC GAA AAC CTG ATC AGG GTC TTC CAG GAG GGG AAG GAC ATC     1920
Ser Gly Asp Glu Asn Leu Ile Arg Val Phe Gln Glu Gly Lys Asp Ile
625                 630                 635                 640

CAC ACC CAG ACC GCA AGC TGG ATG TTC GGC GTC CCC CCG GAG GCC GTG     1968
His Thr Gln Thr Ala Ser Trp Met Phe Gly Val Pro Pro Glu Ala Val
                645                 650                 655

GAC CCC CTG ATG CGC CGG GCG GCC AAG ACG GTG AAC TTC GGC GTC CTC     2016
Asp Pro Leu Met Arg Arg Ala Ala Lys Thr Val Asn Phe Gly Val Leu
            660                 665                 670

TAC GGC ATG TCC GCC CAT AGG CTC TCC CAG GAG CTT GCC ATC CCC TAC     2064
Tyr Gly Met Ser Ala His Arg Leu Ser Gln Glu Leu Ala Ile Pro Tyr
        675                 680                 685

GAG GAG GCG GTG GCC TTT ATA GAG CGC TAC TTC CAA AGC TTC CCC AAG     2112
Glu Glu Ala Val Ala Phe Ile Glu Arg Tyr Phe Gln Ser Phe Pro Lys
    690                 695                 700

GTG CGG GCC TGG ATA GAA AAG ACC CTG GAG GAG GGG AGG AAG CGG GGC     2160
Val Arg Ala Trp Ile Glu Lys Thr Leu Glu Glu Gly Arg Lys Arg Gly
705                 710                 715                 720

TAC GTG GAA ACC CTC TTC GGA AGA AGG CGC TAC GTG CCC GAC CTC AAC     2208
Tyr Val Glu Thr Leu Phe Gly Arg Arg Arg Tyr Val Pro Asp Leu Asn
                725                 730                 735

GCC CGG GTG AAG AGC GTC AGG GAG GCC GCG GAG CGC ATG GCC TTC AAC     2256
Ala Arg Val Lys Ser Val Arg Glu Ala Ala Glu Arg Met Ala Phe Asn
            740                 745                 750

ATG CCC GTC CAG GGC ACC GCC GCC GAC CTC ATG AAG CTC GCC ATG GTG     2304
```

-continued

```
Met Pro Val Gln Gly Thr Ala Ala Asp Leu Met Lys Leu Ala Met Val
        755                 760                 765

AAG CTC TTC CCC CGC CTC CGG GAG ATG GGG GCC CGC ATG CTC CTC CAG     2352
Lys Leu Phe Pro Arg Leu Arg Glu Met Gly Ala Arg Met Leu Leu Gln
    770                 775                 780

GTC CAC GAC GAG CTC CTC CTG GAG GCC CCC CAA GCG CGG GCC GAG GAG     2400
Val His Asp Glu Leu Leu Leu Glu Ala Pro Gln Ala Arg Ala Glu Glu
785                 790                 795                 800

GTG GCG GCT TTG GCC AAG GAG GCC ATG GAG AAG GCC TAT CCC CTC GCC     2448
Val Ala Ala Leu Ala Lys Glu Ala Met Glu Lys Ala Tyr Pro Leu Ala
                805                 810                 815

GTG CCC CTG GAG GTG GAG GTG GGG ATG GGG GAG GAC TGG CTT TCC GCC     2496
Val Pro Leu Glu Val Glu Val Gly Met Gly Glu Asp Trp Leu Ser Ala
            820                 825                 830

AAG GGT TAG                                                         2505
Lys Gly
```

( 2 ) INFORMATION FOR SEQ ID NO:10:

( i ) SEQUENCE CHARACTERISTICS:
( A ) LENGTH: 834 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
```

-continued 245 250 255

Glu Val Asp Leu Ala Gln Gly Arg Glu Pro Asp Arg Glu Gly Leu Arg
260 265 270

Ala Phe Leu Glu Arg Leu Glu Phe Gly Ser Leu Leu His Glu Phe Gly
275 280 285

Leu Leu Glu Ala Pro Ala Pro Leu Glu Glu Ala Pro Trp Pro Pro Pro
290 295 300

Glu Gly Ala Phe Val Gly Phe Val Leu Ser Arg Pro Glu Pro Met Trp
305 310 315 320

Ala Glu Leu Lys Ala Leu Ala Ala Cys Arg Asp Gly Arg Val His Arg
325 330 335

Ala Ala Asp Pro Leu Ala Gly Leu Lys Asp Leu Lys Glu Val Arg Gly
340 345 350

Leu Leu Ala Lys Asp Leu Ala Val Leu Ala Ser Arg Glu Gly Leu Asp
355 360 365

Leu Val Pro Gly Asp Asp Pro Met Leu Leu Ala Tyr Leu Leu Asp Pro
370 375 380

Ser Asn Thr Thr Pro Glu Gly Val Ala Arg Arg Tyr Gly Gly Glu Trp
385 390 395 400

Thr Glu Asp Ala Ala His Arg Ala Leu Leu Ser Glu Arg Leu His Arg
405 410 415

Asn Leu Leu Lys Arg Leu Glu Gly Glu Glu Lys Leu Leu Trp Leu Tyr
420 425 430

His Glu Val Glu Lys Pro Leu Ser Arg Val Leu Ala His Met Glu Ala
435 440 445

Thr Gly Val Arg Leu Asp Val Ala Tyr Leu Gln Ala Leu Ser Leu Glu
450 455 460

Leu Ala Glu Glu Ile Arg Arg Leu Glu Glu Glu Val Phe Arg Leu Ala
465 470 475 480

Gly His Pro Phe Asn Leu Asn Ser Arg Asp Gln Leu Glu Arg Val Leu
485 490 495

Phe Asp Glu Leu Arg Leu Pro Ala Leu Gly Lys Thr Gln Lys Thr Gly
500 505 510

Lys Arg Ser Thr Ser Ala Ala Val Leu Glu Ala Leu Arg Glu Ala His
515 520 525

Pro Ile Val Glu Lys Ile Leu Gln His Arg Glu Leu Thr Lys Leu Lys
530 535 540

Asn Thr Tyr Val Asp Pro Leu Pro Ser Leu Val His Pro Arg Thr Gly
545 550 555 560

Arg Leu His Thr Arg Phe Asn Gln Thr Ala Thr Ala Thr Gly Arg Leu
565 570 575

Ser Ser Ser Asp Pro Asn Leu Gln Asn Ile Pro Val Arg Thr Pro Leu
580 585 590

Gly Gln Arg Ile Arg Arg Ala Phe Val Ala Glu Ala Gly Trp Ala Leu
595 600 605

Val Ala Leu Asp Tyr Ser Gln Ile Glu Leu Arg Val Leu Ala His Leu
610 615 620

Ser Gly Asp Glu Asn Leu Ile Arg Val Phe Gln Glu Gly Lys Asp Ile
625 630 635 640

His Thr Gln Thr Ala Ser Trp Met Phe Gly Val Pro Pro Glu Ala Val
645 650 655

Asp Pro Leu Met Arg Arg Ala Ala Lys Thr Val Asn Phe Gly Val Leu
660 665 670

-continued

Tyr Gly Met Ser Ala His Arg Leu Ser Gln Glu Leu Ala Ile Pro Tyr
675 680 685

Glu Glu Ala Val Ala Phe Ile Glu Arg Tyr Phe Gln Ser Phe Pro Lys
690 695 700

Val Arg Ala Trp Ile Glu Lys Thr Leu Glu Glu Gly Arg Lys Arg Gly
705 710 715 720

Tyr Val Glu Thr Leu Phe Gly Arg Arg Arg Tyr Val Pro Asp Leu Asn
725 730 735

Ala Arg Val Lys Ser Val Arg Glu Ala Ala Glu Arg Met Ala Phe Asn
740 745 750

Met Pro Val Gln Gly Thr Ala Ala Asp Leu Met Lys Leu Ala Met Val
755 760 765

Lys Leu Phe Pro Arg Leu Arg Glu Met Gly Ala Arg Met Leu Leu Gln
770 775 780

Val His Asp Glu Leu Leu Leu Glu Ala Pro Gln Ala Arg Ala Glu Glu
785 790 795 800

Val Ala Ala Leu Ala Lys Glu Ala Met Glu Lys Ala Tyr Pro Leu Ala
805 810 815

Val Pro Leu Glu Val Glu Val Gly Met Gly Glu Asp Trp Leu Ser Ala
820 825 830

Lys Gly ( 2 ) INFORMATION FOR SEQ ID NO:11:

( i ) SEQUENCE CHARACTERISTICS:
( A ) LENGTH: 2679 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Thermosipho africanus ( i x ) FEATURE:
( A ) NAME/KEY: CDS
( B ) LOCATION: 1..2676

( x i ) SEQUENCE DESCRIPTION: SEQ ID NO:11:

ATG GGA AAG ATG TTT CTA TTT GAT GGA ACT GGA TTA GTA TAC AGA GCA 48
Met Gly Lys Met Phe Leu Phe Asp Gly Thr Gly Leu Val Tyr Arg Ala
1 5 10 15

TTT TAT GCT ATA GAT CAA TCT CTT CAA ACT TCG TCT GGT TTA CAC ACT 96
Phe Tyr Ala Ile Asp Gln Ser Leu Gln Thr Ser Ser Gly Leu His Thr
20 25 30

AAT GCT GTA TAC GGA CTT ACT AAA ATG CTT ATA AAA TTT TTA AAA GAA 144
Asn Ala Val Tyr Gly Leu Thr Lys Met Leu Ile Lys Phe Leu Lys Glu
35 40 45

CAT ATC AGT ATT GGA AAA GAT GCT TGT GTT TTT GTT TTA GAT TCA AAA 192
His Ile Ser Ile Gly Lys Asp Ala Cys Val Phe Val Leu Asp Ser Lys
50 55 60

GGT GGT AGC AAA AAA AGA AAG GAT ATT CTT GAA ACA TAT AAA GCA AAT 240
Gly Gly Ser Lys Lys Arg Lys Asp Ile Leu Glu Thr Tyr Lys Ala Asn
65 70 75 80

AGG CCA TCA ACG CCT GAT TTA CTT TTA GAG CAA ATT CCA TAT GTA GAA 288
Arg Pro Ser Thr Pro Asp Leu Leu Leu Glu Gln Ile Pro Tyr Val Glu
85 90 95

-continued

```
GAA CTT GTT GAT GCT CTT GGA ATA AAA GTT TTA AAA ATA GAA GGC TTT        336
Glu Leu Val Asp Ala Leu Gly Ile Lys Val Leu Lys Ile Glu Gly Phe
            100                 105                 110

GAA GCT GAT GAC ATT ATT GCT ACG CTT TCT AAA AAA TTT GAA AGT GAT        384
Glu Ala Asp Asp Ile Ile Ala Thr Leu Ser Lys Lys Phe Glu Ser Asp
        115                 120                 125

TTT GAA AAG GTA AAC ATA ATA ACT GGA GAT AAA GAT CTT TTA CAA CTT        432
Phe Glu Lys Val Asn Ile Ile Thr Gly Asp Lys Asp Leu Leu Gln Leu
    130                 135                 140

GTT TCT GAT AAG GTT TTT GTT TGG AGA GTA GAA AGA GGA ATA ACA GAT        480
Val Ser Asp Lys Val Phe Val Trp Arg Val Glu Arg Gly Ile Thr Asp
145                 150                 155                 160

TTG GTA TTG TAC GAT AGA AAT AAA GTG ATT GAA AAA TAT GGA ATC TAC        528
Leu Val Leu Tyr Asp Arg Asn Lys Val Ile Glu Lys Tyr Gly Ile Tyr
                165                 170                 175

CCA GAA CAA TTC AAA GAT TAT TTA TCT CTT GTC GGT GAT CAG ATT GAT        576
Pro Glu Gln Phe Lys Asp Tyr Leu Ser Leu Val Gly Asp Gln Ile Asp
            180                 185                 190

AAT ATC CCA GGA GTT AAA GGA ATA GGA AAG AAA ACA GCT GTT TCG CTT        624
Asn Ile Pro Gly Val Lys Gly Ile Gly Lys Lys Thr Ala Val Ser Leu
        195                 200                 205

TTG AAA AAA TAT AAT AGC TTG GAA AAT GTA TTA AAA AAT ATT AAC CTT        672
Leu Lys Lys Tyr Asn Ser Leu Glu Asn Val Leu Lys Asn Ile Asn Leu
    210                 215                 220

TTG ACG GAA AAA TTA AGA AGG CTT TTG GAA GAT TCA AAG GAA GAT TTG        720
Leu Thr Glu Lys Leu Arg Arg Leu Leu Glu Asp Ser Lys Glu Asp Leu
225                 230                 235                 240

CAA AAA AGT ATA GAA CTT GTG GAG TTG ATA TAT GAT GTA CCA ATG GAT        768
Gln Lys Ser Ile Glu Leu Val Glu Leu Ile Tyr Asp Val Pro Met Asp
                245                 250                 255

GTG GAA AAA GAT GAA ATA ATT TAT AGA GGG TAT AAT CCA GAT AAG CTT        816
Val Glu Lys Asp Glu Ile Ile Tyr Arg Gly Tyr Asn Pro Asp Lys Leu
            260                 265                 270

TTA AAG GTA TTA AAA AAG TAC GAA TTT TCA TCT ATA ATT AAG GAG TTA        864
Leu Lys Val Leu Lys Lys Tyr Glu Phe Ser Ser Ile Ile Lys Glu Leu
        275                 280                 285

AAT TTA CAA GAA AAA TTA GAA AAG GAA TAT ATA CTG GTA GAT AAT GAA        912
Asn Leu Gln Glu Lys Leu Glu Lys Glu Tyr Ile Leu Val Asp Asn Glu
    290                 295                 300

GAT AAA TTG AAA AAA CTT GCA GAA GAG ATA GAA AAA TAC AAA ACT TTT        960
Asp Lys Leu Lys Lys Leu Ala Glu Glu Ile Glu Lys Tyr Lys Thr Phe
305                 310                 315                 320

TCA ATT GAT ACG GAA ACA ACT TCA CTT GAT CCA TTT GAA GCT AAA CTG       1008
Ser Ile Asp Thr Glu Thr Thr Ser Leu Asp Pro Phe Glu Ala Lys Leu
                325                 330                 335

GTT GGG ATC TCT ATT TCC ACA ATG GAA GGG AAG GCG TAT TAT ATT CCG       1056
Val Gly Ile Ser Ile Ser Thr Met Glu Gly Lys Ala Tyr Tyr Ile Pro
            340                 345                 350

GTG TCT CAT TTT GGA GCT AAG AAT ATT TCC AAA AGT TTA ATA GAT AAA       1104
Val Ser His Phe Gly Ala Lys Asn Ile Ser Lys Ser Leu Ile Asp Lys
        355                 360                 365

TTT CTA AAA CAA ATT TTG CAA GAG AAG GAT TAT AAT ATC GTT GGT CAG       1152
Phe Leu Lys Gln Ile Leu Gln Glu Lys Asp Tyr Asn Ile Val Gly Gln
    370                 375                 380

AAT TTA AAA TTT GAC TAT GAG ATT TTT AAA AGC ATG GGT TTT TCT CCA       1200
Asn Leu Lys Phe Asp Tyr Glu Ile Phe Lys Ser Met Gly Phe Ser Pro
385                 390                 395                 400

AAT GTT CCG CAT TTT GAT ACG ATG ATT GCA GCC TAT CTT TTA AAT CCA       1248
Asn Val Pro His Phe Asp Thr Met Ile Ala Ala Tyr Leu Leu Asn Pro
                405                 410                 415
```

-continued

```
GAT GAA AAA CGT TTT AAT CTT GAA GAG CTA TCC TTA AAA TAT TTA GGT    1296
Asp Glu Lys Arg Phe Asn Leu Glu Glu Leu Ser Leu Lys Tyr Leu Gly
            420                 425                 430

TAT AAA ATG ATC TCG TTT GAT GAA TTA GTA AAT GAA AAT GTA CCA TTG    1344
Tyr Lys Met Ile Ser Phe Asp Glu Leu Val Asn Glu Asn Val Pro Leu
        435                 440                 445

TTT GGA AAT GAC TTT TCG TAT GTT CCA CTA GAA AGA GCC GTT GAG TAT    1392
Phe Gly Asn Asp Phe Ser Tyr Val Pro Leu Glu Arg Ala Val Glu Tyr
    450                 455                 460

TCC TGT GAA GAT GCC GAT GTG ACA TAC AGA ATA TTT AGA AAG CTT GGT    1440
Ser Cys Glu Asp Ala Asp Val Thr Tyr Arg Ile Phe Arg Lys Leu Gly
465                 470                 475                 480

AGG AAG ATA TAT GAA AAT GAG ATG GAA AAG TTG TTT TAC GAA ATT GAG    1488
Arg Lys Ile Tyr Glu Asn Glu Met Glu Lys Leu Phe Tyr Glu Ile Glu
                485                 490                 495

ATG CCC TTA ATT GAT GTT CTT TCA GAA ATG GAA CTA AAT GGA GTG TAT    1536
Met Pro Leu Ile Asp Val Leu Ser Glu Met Glu Leu Asn Gly Val Tyr
            500                 505                 510

TTT GAT GAG GAA TAT TTA AAA GAA TTA TCA AAA AAA TAT CAA GAA AAA    1584
Phe Asp Glu Glu Tyr Leu Lys Glu Leu Ser Lys Lys Tyr Gln Glu Lys
        515                 520                 525

ATG GAT GGA ATT AAG GAA AAA GTT TTT GAG ATA GCT GGT GAA ACT TTC    1632
Met Asp Gly Ile Lys Glu Lys Val Phe Glu Ile Ala Gly Glu Thr Phe
    530                 535                 540

AAT TTA AAC TCT TCA ACT CAA GTA GCA TAT ATA CTA TTT GAA AAA TTA    1680
Asn Leu Asn Ser Ser Thr Gln Val Ala Tyr Ile Leu Phe Glu Lys Leu
545                 550                 555                 560

AAT ATT GCT CCT TAC AAA AAA ACA GCG ACT GGT AAG TTT TCA ACT AAT    1728
Asn Ile Ala Pro Tyr Lys Lys Thr Ala Thr Gly Lys Phe Ser Thr Asn
                565                 570                 575

GCG GAA GTT TTA GAA GAA CTT TCA AAA GAA CAT GAA ATT GCA AAA TTG    1776
Ala Glu Val Leu Glu Glu Leu Ser Lys Glu His Glu Ile Ala Lys Leu
            580                 585                 590

TTG CTG GAG TAT CGA AAG TAT CAA AAA TTA AAA AGT ACA TAT ATT GAT    1824
Leu Leu Glu Tyr Arg Lys Tyr Gln Lys Leu Lys Ser Thr Tyr Ile Asp
        595                 600                 605

TCA ATA CCG TTA TCT ATT AAT CGA AAA ACA AAC AGG GTC CAT ACT ACT    1872
Ser Ile Pro Leu Ser Ile Asn Arg Lys Thr Asn Arg Val His Thr Thr
    610                 615                 620

TTT CAT CAA ACA GGA ACT TCT ACT GGA AGA TTA AGT AGT TCA AAT CCA    1920
Phe His Gln Thr Gly Thr Ser Thr Gly Arg Leu Ser Ser Ser Asn Pro
625                 630                 635                 640

AAT TTG CAA AAT CTT CCA ACA AGA AGC GAA GAA GGA AAA GAA ATA AGA    1968
Asn Leu Gln Asn Leu Pro Thr Arg Ser Glu Glu Gly Lys Glu Ile Arg
                645                 650                 655

AAA GCA GTA AGA CCT CAA AGA CAA GAT TGG TGG ATT TTA GGT GCT GAC    2016
Lys Ala Val Arg Pro Gln Arg Gln Asp Trp Trp Ile Leu Gly Ala Asp
            660                 665                 670

TAT TCT CAG ATA GAA CTA AGG GTT TTA GCG CAT GTA AGT AAA GAT GAA    2064
Tyr Ser Gln Ile Glu Leu Arg Val Leu Ala His Val Ser Lys Asp Glu
        675                 680                 685

AAT CTA CTT AAA GCA TTT AAA GAA GAT TTA GAT ATT CAT ACA ATT ACT    2112
Asn Leu Leu Lys Ala Phe Lys Glu Asp Leu Asp Ile His Thr Ile Thr
    690                 695                 700

GCT GCC AAA ATT TTT GGT GTT TCA GAG ATG TTT GTT AGT GAA CAA ATG    2160
Ala Ala Lys Ile Phe Gly Val Ser Glu Met Phe Val Ser Glu Gln Met
705                 710                 715                 720

AGA AGA GTT GGA AAG ATG GTA AAT TTT GCA ATT ATT TAT GGA GTT TCA    2208
Arg Arg Val Gly Lys Met Val Asn Phe Ala Ile Ile Tyr Gly Val Ser
                725                 730                 735
```

CCT TAT GGT CTT TCA AAG AGA ATT GGT CTT AGT GTT TCA GAG ACT AAA 2256
Pro Tyr Gly Leu Ser Lys Arg Ile Gly Leu Ser Val Ser Glu Thr Lys
740 745 750

AAA ATA ATA GAT AAC TAT TTT AGA TAC TAT AAA GGA GTT TTT GAA TAT 2304
Lys Ile Ile Asp Asn Tyr Phe Arg Tyr Tyr Lys Gly Val Phe Glu Tyr
755 760 765

TTA AAA AGG ATG AAA GAT GAA GCA AGG AAA AAA GGT TAT GTT ACA ACG 2352
Leu Lys Arg Met Lys Asp Glu Ala Arg Lys Lys Gly Tyr Val Thr Thr
770 775 780

CTT TTT GGA AGG CGC AGA TAT ATT CCA CAG TTA AGA TCG AAA AAT GGT 2400
Leu Phe Gly Arg Arg Arg Tyr Ile Pro Gln Leu Arg Ser Lys Asn Gly
785 790 795 800

AAT AGA GTT CAA GAA GGA GAA AGA ATA GCT GTA AAC ACT CCA ATT CAA 2448
Asn Arg Val Gln Glu Gly Glu Arg Ile Ala Val Asn Thr Pro Ile Gln
805 810 815

GGA ACA GCA GCT GAT ATA ATA AAG ATA GCT ATG ATT AAT ATT CAT AAT 2496
Gly Thr Ala Ala Asp Ile Ile Lys Ile Ala Met Ile Asn Ile His Asn
820 825 830

AGA TTG AAG AAG GAA AAT CTA CGT TCA AAA ATG ATA TTG CAG GTT CAT 2544
Arg Leu Lys Lys Glu Asn Leu Arg Ser Lys Met Ile Leu Gln Val His
835 840 845

GAC GAG TTA GTT TTT GAA GTG CCC GAT AAT GAA CTG GAG ATT GTA AAA 2592
Asp Glu Leu Val Phe Glu Val Pro Asp Asn Glu Leu Glu Ile Val Lys
850 855 860

GAT TTA GTA AGA GAT GAG ATG GAA AAT GCA GTT AAG CTA GAC GTT CCT 2640
Asp Leu Val Arg Asp Glu Met Glu Asn Ala Val Lys Leu Asp Val Pro
865 870 875 880

TTA AAA GTA GAT GTT TAT TAT GGA AAA GAG TGG GAA TAA 2679
Leu Lys Val Asp Val Tyr Tyr Gly Lys Glu Trp Glu
885 890

( 2 ) INFORMATION FOR SEQ ID NO:12:

( i ) SEQUENCE CHARACTERISTICS:
( A ) LENGTH: 892 amino acids
( B ) TYPE: amino acid
( D ) TOPOLOGY: linear ( i i ) MOLECULE TYPE: protein ( x i ) SEQUENCE DESCRIPTION: SEQ ID NO:12:

Met Gly Lys Met Phe Leu Phe Asp Gly Thr Gly Leu Val Tyr Arg Ala
1 5 10 15

Phe Tyr Ala Ile Asp Gln Ser Leu Gln Thr Ser Ser Gly Leu His Thr
20 25 30

Asn Ala Val Tyr Gly Leu Thr Lys Met Leu Ile Lys Phe Leu Lys Glu
35 40 45

His Ile Ser Ile Gly Lys Asp Ala Cys Val Phe Val Leu Asp Ser Lys
50 55 60

Gly Gly Ser Lys Lys Arg Lys Asp Ile Leu Glu Thr Tyr Lys Ala Asn
65 70 75 80

Arg Pro Ser Thr Pro Asp Leu Leu Leu Glu Gln Ile Pro Tyr Val Glu
85 90 95

Glu Leu Val Asp Ala Leu Gly Ile Lys Val Leu Lys Ile Glu Gly Phe
100 105 110

Glu Ala Asp Asp Ile Ile Ala Thr Leu Ser Lys Lys Phe Glu Ser Asp
115 120 125

Phe Glu Lys Val Asn Ile Ile Thr Gly Asp Lys Asp Leu Leu Gln Leu
130 135 140

Val Ser Asp Lys Val Phe Val Trp Arg Val Glu Arg Gly Ile Thr Asp

-continued 145 150 155 160

Leu Val Leu Tyr Asp Arg Asn Lys Val Ile Glu Lys Tyr Gly Ile Tyr
165 170 175

Pro Glu Gln Phe Lys Asp Tyr Leu Ser Leu Val Gly Asp Gln Ile Asp
180 185 190

Asn Ile Pro Gly Val Lys Gly Ile Gly Lys Lys Thr Ala Val Ser Leu
195 200 205

Leu Lys Lys Tyr Asn Ser Leu Glu Asn Val Leu Lys Asn Ile Asn Leu
210 215 220

Leu Thr Glu Lys Leu Arg Arg Leu Leu Glu Asp Ser Lys Glu Asp Leu
225 230 235 240

Gln Lys Ser Ile Glu Leu Val Glu Leu Ile Tyr Asp Val Pro Met Asp
245 250 255

Val Glu Lys Asp Glu Ile Ile Tyr Arg Gly Tyr Asn Pro Asp Lys Leu
260 265 270

Leu Lys Val Leu Lys Lys Tyr Glu Phe Ser Ser Ile Ile Lys Glu Leu
275 280 285

Asn Leu Gln Glu Lys Leu Glu Lys Glu Tyr Ile Leu Val Asp Asn Glu
290 295 300

Asp Lys Leu Lys Lys Leu Ala Glu Glu Ile Glu Lys Tyr Lys Thr Phe
305 310 315 320

Ser Ile Asp Thr Glu Thr Thr Ser Leu Asp Pro Phe Glu Ala Lys Leu
325 330 335

Val Gly Ile Ser Ile Ser Thr Met Glu Gly Lys Ala Tyr Tyr Ile Pro
340 345 350

Val Ser His Phe Gly Ala Lys Asn Ile Ser Lys Ser Leu Ile Asp Lys
355 360 365

Phe Leu Lys Gln Ile Leu Gln Glu Lys Asp Tyr Asn Ile Val Gly Gln
370 375 380

Asn Leu Lys Phe Asp Tyr Glu Ile Phe Lys Ser Met Gly Phe Ser Pro
385 390 395 400

Asn Val Pro His Phe Asp Thr Met Ile Ala Ala Tyr Leu Leu Asn Pro
405 410 415

Asp Glu Lys Arg Phe Asn Leu Glu Glu Leu Ser Leu Lys Tyr Leu Gly
420 425 430

Tyr Lys Met Ile Ser Phe Asp Glu Leu Val Asn Glu Asn Val Pro Leu
435 440 445

Phe Gly Asn Asp Phe Ser Tyr Val Pro Leu Glu Arg Ala Val Glu Tyr
450 455 460

Ser Cys Glu Asp Ala Asp Val Thr Tyr Arg Ile Phe Arg Lys Leu Gly
465 470 475 480

Arg Lys Ile Tyr Glu Asn Glu Met Glu Lys Leu Phe Tyr Glu Ile Glu
485 490 495

Met Pro Leu Ile Asp Val Leu Ser Glu Met Glu Leu Asn Gly Val Tyr
500 505 510

Phe Asp Glu Glu Tyr Leu Lys Glu Leu Ser Lys Lys Tyr Gln Glu Lys
515 520 525

Met Asp Gly Ile Lys Glu Lys Val Phe Glu Ile Ala Gly Glu Thr Phe
530 535 540

Asn Leu Asn Ser Ser Thr Gln Val Ala Tyr Ile Leu Phe Glu Lys Leu
545 550 555 560

Asn Ile Ala Pro Tyr Lys Lys Thr Ala Thr Gly Lys Phe Ser Thr Asn
565 570 575

-continued

| | | | | | | | | | | | | | | | |
|---|---|---|---|---|---|---|---|---|---|---|---|---|---|---|---|
| Ala | Glu | Val | Leu | Glu | Glu | Leu | Ser | Lys | Glu | His | Glu | Ile | Ala | Lys | Leu |
| | | | 580 | | | | | 585 | | | | | 590 | | |
| Leu | Leu | Glu | Tyr | Arg | Lys | Tyr | Gln | Lys | Leu | Lys | Ser | Thr | Tyr | Ile | Asp |
| | | 595 | | | | | 600 | | | | | 605 | | | |
| Ser | Ile | Pro | Leu | Ser | Ile | Asn | Arg | Lys | Thr | Asn | Arg | Val | His | Thr | Thr |
| | 610 | | | | | 615 | | | | | 620 | | | | |
| Phe | His | Gln | Thr | Gly | Thr | Ser | Thr | Gly | Arg | Leu | Ser | Ser | Ser | Asn | Pro |
| 625 | | | | | 630 | | | | | 635 | | | | | 640 |
| Asn | Leu | Gln | Asn | Leu | Pro | Thr | Arg | Ser | Glu | Glu | Gly | Lys | Glu | Ile | Arg |
| | | | | 645 | | | | | 650 | | | | | 655 | |
| Lys | Ala | Val | Arg | Pro | Gln | Arg | Gln | Asp | Trp | Trp | Ile | Leu | Gly | Ala | Asp |
| | | | 660 | | | | | 665 | | | | | 670 | | |
| Tyr | Ser | Gln | Ile | Glu | Leu | Arg | Val | Leu | Ala | His | Val | Ser | Lys | Asp | Glu |
| | | 675 | | | | | 680 | | | | | 685 | | | |
| Asn | Leu | Leu | Lys | Ala | Phe | Lys | Glu | Asp | Leu | Asp | Ile | His | Thr | Ile | Thr |
| | 690 | | | | | 695 | | | | | 700 | | | | |
| Ala | Ala | Lys | Ile | Phe | Gly | Val | Ser | Glu | Met | Phe | Val | Ser | Glu | Gln | Met |
| 705 | | | | | 710 | | | | | 715 | | | | | 720 |
| Arg | Arg | Val | Gly | Lys | Met | Val | Asn | Phe | Ala | Ile | Ile | Tyr | Gly | Val | Ser |
| | | | | 725 | | | | | 730 | | | | | 735 | |
| Pro | Tyr | Gly | Leu | Ser | Lys | Arg | Ile | Gly | Leu | Ser | Val | Ser | Glu | Thr | Lys |
| | | | 740 | | | | | 745 | | | | | 750 | | |
| Lys | Ile | Ile | Asp | Asn | Tyr | Phe | Arg | Tyr | Tyr | Lys | Gly | Val | Phe | Glu | Tyr |
| | | 755 | | | | | 760 | | | | | 765 | | | |
| Leu | Lys | Arg | Met | Lys | Asp | Glu | Ala | Arg | Lys | Lys | Gly | Tyr | Val | Thr | Thr |
| | 770 | | | | | 775 | | | | | 780 | | | | |
| Leu | Phe | Gly | Arg | Arg | Arg | Tyr | Ile | Pro | Gln | Leu | Arg | Ser | Lys | Asn | Gly |
| 785 | | | | | 790 | | | | | 795 | | | | | 800 |
| Asn | Arg | Val | Gln | Glu | Gly | Glu | Arg | Ile | Ala | Val | Asn | Thr | Pro | Ile | Gln |
| | | | | 805 | | | | | 810 | | | | | 815 | |
| Gly | Thr | Ala | Ala | Asp | Ile | Ile | Lys | Ile | Ala | Met | Ile | Asn | Ile | His | Asn |
| | | | 820 | | | | | 825 | | | | | 830 | | |
| Arg | Leu | Lys | Lys | Glu | Asn | Leu | Arg | Ser | Lys | Met | Ile | Leu | Gln | Val | His |
| | | 835 | | | | | 840 | | | | | 845 | | | |
| Asp | Glu | Leu | Val | Phe | Glu | Val | Pro | Asp | Asn | Glu | Leu | Glu | Ile | Val | Lys |
| | 850 | | | | | 855 | | | | | 860 | | | | |
| Asp | Leu | Val | Arg | Asp | Glu | Met | Glu | Asn | Ala | Val | Lys | Leu | Asp | Val | Pro |
| 865 | | | | | 870 | | | | | 875 | | | | | 880 |
| Leu | Lys | Val | Asp | Val | Tyr | Tyr | Gly | Lys | Glu | Trp | Glu | | | | |
| | | | | 885 | | | | | 890 | | | | | | |

( 2 ) INFORMATION FOR SEQ ID NO:13:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: DNA probe BW33

( i i i ) HYPOTHETICAL: NO ( i v ) ANTI-SENSE: NO ( x i ) SEQUENCE DESCRIPTION: SEQ ID NO:13:

GATCGCTGCG CGTAACCACC ACACCCGCCG CGC 33

( 2 ) INFORMATION FOR SEQ ID NO:14:

( i ) SEQUENCE CHARACTERISTICS:
( A ) LENGTH: 30 nucleotides
( B ) TYPE: nucleic acid
( C ) STRANDEDNESS: single
( D ) TOPOLOGY: linear ( i i ) MOLECULE TYPE: DNA primer BW37

( i i i ) HYPOTHETICAL: NO ( i v ) ANTI-SENSE: NO ( x i ) SEQUENCE DESCRIPTION: SEQ ID NO:14:

GCGCTAGGGC GCTGGCAAGT GTAGCGGTCA 30

( 2 ) INFORMATION FOR SEQ ID NO:15:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i i i ) HYPOTHETICAL: YES ( i v ) ANTI-SENSE: NO ( i x ) FEATURE:
( A ) NAME/KEY: Peptide
( B ) LOCATION: 1..4
( D ) OTHER INFORMATION: /label=Xaa
/ note= "Xaa = Val or Thr"

( x i ) SEQUENCE DESCRIPTION: SEQ ID NO:15:

Ala Xaa Tyr Gly
1

( 2 ) INFORMATION FOR SEQ ID NO:16:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

His Glu Ala Tyr Gly
1 5

( 2 ) INFORMATION FOR SEQ ID NO:17:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:17:

His Glu Ala Tyr Glu
1 5

( 2 ) INFORMATION FOR SEQ ID NO:18:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Peptide
( B ) LOCATION: 1..4
( D ) OTHER INFORMATION: /label=Xaa
/ note= "Xaa = Leu or Ile"

( x i ) SEQUENCE DESCRIPTION: SEQ ID NO:18:

Xaa Leu Glu Thr
1

( 2 ) INFORMATION FOR SEQ ID NO:19:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Peptide
( B ) LOCATION: 1..7
( D ) OTHER INFORMATION: /label=Xaa
/ note= "Xaa = Leu or Ile"

( x i ) SEQUENCE DESCRIPTION: SEQ ID NO:19:

Xaa Leu Glu Thr Tyr Lys Ala
1 5

( 2 ) INFORMATION FOR SEQ ID NO:20:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Peptide
( B ) LOCATION: 1..7
( D ) OTHER INFORMATION: /label=Xaa1-4
/ note= "Xaa1 = Ile or Leu or Ala; Xaa2-4, each = any amino acid"

( x i ) SEQUENCE DESCRIPTION: SEQ ID NO:20:

Xaa Xaa Xaa Xaa Tyr Lys Ala
1 5

( 2 ) INFORMATION FOR SEQ ID NO:21:

( i ) SEQUENCE CHARACTERISTICS:
( A ) LENGTH: 22 nucleotides
( B ) TYPE: nucleic acid
( C ) STRANDEDNESS: single
( D ) TOPOLOGY: linear ( i i ) MOLECULE TYPE: DNA primer MK61

( i i i ) HYPOTHETICAL: NO ( i v ) ANTI-SENSE: NO ( x i ) SEQUENCE DESCRIPTION: SEQ ID NO:21:

AGGACTACAA CTGCCACACA CC 22

( 2 ) INFORMATION FOR SEQ ID NO:22:

( i ) SEQUENCE CHARACTERISTICS:
( A ) LENGTH: 38 nucleotides
( B ) TYPE: nucleic acid
( C ) STRANDEDNESS: single
( D ) TOPOLOGY: linear ( i i ) MOLECULE TYPE: DNA primer RA01

( i i i ) HYPOTHETICAL: NO ( i v ) ANTI-SENSE: NO ( x i ) SEQUENCE DESCRIPTION: SEQ ID NO:22:

CGAGGCGCGC CAGCCCCAGG AGATCTACCA GCTCCTTG 38

( 2 ) INFORMATION FOR SEQ ID NO:23:

( i ) SEQUENCE CHARACTERISTICS:
( A ) LENGTH: 20 nucleotides
( B ) TYPE: nucleic acid
( C ) STRANDEDNESS: single
( D ) TOPOLOGY: linear ( i i ) MOLECULE TYPE: DNA primer DG29

( i i i ) HYPOTHETICAL: NO ( i v ) ANTI-SENSE: NO ( x i ) SEQUENCE DESCRIPTION: SEQ ID NO:23:

AGCTTATGTC TCCAAAAGCT 20

( 2 ) INFORMATION FOR SEQ ID NO:24:

( i ) SEQUENCE CHARACTERISTICS:
( A ) LENGTH: 16 nucleotides
( B ) TYPE: nucleic acid
( C ) STRANDEDNESS: single
( D ) TOPOLOGY: linear ( i i ) MOLECULE TYPE: DNA primer DG30

( i i i ) HYPOTHETICAL: NO ( i v ) ANTI-SENSE: NO ( x i ) SEQUENCE DESCRIPTION: SEQ ID NO:24:

-continued

AGCTTTTGGA GACATA 16

( 2 ) INFORMATION FOR SEQ ID NO:25:

( i ) SEQUENCE CHARACTERISTICS:
( A ) LENGTH: 25 nucleotides
( B ) TYPE: nucleic acid
( C ) STRANDEDNESS: single
( D ) TOPOLOGY: linear ( i i ) MOLECULE TYPE: DNA primer PL10

( i i i ) HYPOTHETICAL: NO ( i v ) ANTI-SENSE: NO ( x i ) SEQUENCE DESCRIPTION: SEQ ID NO:25:

GGCGTACCTT TGTCTCACGG GCAAC 25

( 2 ) INFORMATION FOR SEQ ID NO:26:

( i ) SEQUENCE CHARACTERISTICS:
( A ) LENGTH: 28 nucleotides
( B ) TYPE: nucleic acid
( C ) STRANDEDNESS: single
( D ) TOPOLOGY: linear ( i i ) MOLECULE TYPE: DNA primer FL63

( i i i ) HYPOTHETICAL: NO ( i v ) ANTI-SENSE: NO ( x i ) SEQUENCE DESCRIPTION: SEQ ID NO:26:

GATAAAGGCA TGCTTCAGCT TGTGAACG 28

( 2 ) INFORMATION FOR SEQ ID NO:27:

( i ) SEQUENCE CHARACTERISTICS:
( A ) LENGTH: 27 nucleotides
( B ) TYPE: nucleic acid
( C ) STRANDEDNESS: single
( D ) TOPOLOGY: linear ( i i ) MOLECULE TYPE: DNA primer FL69

( i i i ) HYPOTHETICAL: NO ( i v ) ANTI-SENSE: NO ( x i ) SEQUENCE DESCRIPTION: SEQ ID NO:27:

TGTACTTCTC TAGAAGCTGA ACAGCAG 27

( 2 ) INFORMATION FOR SEQ ID NO:28:

( i ) SEQUENCE CHARACTERISTICS:
( A ) LENGTH: 36 nucleotides
( B ) TYPE: nucleic acid
( C ) STRANDEDNESS: single
( D ) TOPOLOGY: linear ( i i ) MOLECULE TYPE: DNA primer FL64

( i i i ) HYPOTHETICAL: NO ( i v ) ANTI-SENSE: NO ( x i ) SEQUENCE DESCRIPTION: SEQ ID NO:28:

CTGAAGCATG TCTTTGTCAC CGGTTACTAT CAATAT 36

-continued ( 2 ) INFORMATION FOR SEQ ID NO:29:

( i ) SEQUENCE CHARACTERISTICS:
( A ) LENGTH: 18 nucleotides
( B ) TYPE: nucleic acid
( C ) STRANDEDNESS: single
( D ) TOPOLOGY: linear ( i i ) MOLECULE TYPE: DNA primer FL65

( i i i ) HYPOTHETICAL: NO ( i v ) ANTI-SENSE: NO ( x i ) SEQUENCE DESCRIPTION: SEQ ID NO:29:

TAGTAACCGG TGACAAAG 18

( 2 ) INFORMATION FOR SEQ ID NO:30:

( i ) SEQUENCE CHARACTERISTICS:
( A ) LENGTH: 31 nucleotides
( B ) TYPE: nucleic acid
( C ) STRANDEDNESS: single
( D ) TOPOLOGY: linear ( i i ) MOLECULE TYPE: DNA primer FL66

( i i i ) HYPOTHETICAL: NO ( i v ) ANTI-SENSE: NO ( x i ) SEQUENCE DESCRIPTION: SEQ ID NO:30:

CTATGCCATG GATAGATCGC TTTCTACTTC C 31

( 2 ) INFORMATION FOR SEQ ID NO:31:

( i ) SEQUENCE CHARACTERISTICS:
( A ) LENGTH: 31 nucleotides
( B ) TYPE: nucleic acid
( C ) STRANDEDNESS: single
( D ) TOPOLOGY: linear ( i i ) MOLECULE TYPE: DNA primer FL67

( i i i ) HYPOTHETICAL: NO ( i v ) ANTI-SENSE: NO ( x i ) SEQUENCE DESCRIPTION: SEQ ID NO:31:

CAAGCCCATG GAAACTTACA AGGCTCAAAG A 31

( 2 ) INFORMATION FOR SEQ ID NO:32:

( i ) SEQUENCE CHARACTERISTICS:
( A ) LENGTH: 49 nucleotides
( B ) TYPE: nucleic acid
( C ) STRANDEDNESS: single
( D ) TOPOLOGY: linear ( i i ) MOLECULE TYPE: DNA primer TZA292

( i i i ) HYPOTHETICAL: NO ( i v ) ANTI-SENSE: NO ( x i ) SEQUENCE DESCRIPTION: SEQ ID NO:32:

GTCGGCATAT GGCTCCTGCT CCTCTTGAGG AGGCCCCCTG GCCCCCGCC 49

( 2 ) INFORMATION FOR SEQ ID NO:33:

( i ) SEQUENCE CHARACTERISTICS:
( A ) LENGTH: 37 nucleotides (B) TYPE: nucleic acid
(C) STRANDEDNESS: single
(D) TOPOLOGY: linear (ii) MOLECULE TYPE: DNA primer TZR01

(iii) HYPOTHETICAL: NO (iv) ANTI-SENSE: NO (xi) SEQUENCE DESCRIPTION: SEQ ID NO:33:

GACGCAGATC TCAGCCCTTG GCGGAAAGCC AGTCCTC 37

(2) INFORMATION FOR SEQ ID NO:34:

(i) SEQUENCE CHARACTERISTICS:
(A) LENGTH: 49 nucleotides
(B) TYPE: nucleic acid
(C) STRANDEDNESS: single
(D) TOPOLOGY: linear (ii) MOLECULE TYPE: DNA primer TSA288

(iii) HYPOTHETICAL: NO (iv) ANTI-SENSE: NO (xi) SEQUENCE DESCRIPTION: SEQ ID NO:34:

GTCGGCATAT GGCTCCTAAA GAAGCTGAGG AGGCCCCCTG GCCCCCGCC 49

(2) INFORMATION FOR SEQ ID NO:35:

(i) SEQUENCE CHARACTERISTICS:
(A) LENGTH: 37 nucleotides
(B) TYPE: nucleic acid
(C) STRANDEDNESS: single
(D) TOPOLOGY: linear (ii) MOLECULE TYPE: DNA primer TSR01

(iii) HYPOTHETICAL: NO (iv) ANTI-SENSE: NO (xi) SEQUENCE DESCRIPTION: SEQ ID NO:35:

GACGCAGATC TCAGGCCTTG GCGGAAAGCC AGTCCTC 37

(2) INFORMATION FOR SEQ ID NO:36:

(i) SEQUENCE CHARACTERISTICS:
(A) LENGTH: 41 nucleotides
(B) TYPE: nucleic acid
(C) STRANDEDNESS: single
(D) TOPOLOGY: linear (ii) MOLECULE TYPE: DNA primer DG122

(iii) HYPOTHETICAL: NO (iv) ANTI-SENSE: NO (xi) SEQUENCE DESCRIPTION: SEQ ID NO:36:

CCTCTAAACG GCAGATCTGA TATCAACCCT TGGCGGAAAG C 41

(2) INFORMATION FOR SEQ ID NO:37:

(i) SEQUENCE CHARACTERISTICS:
(A) LENGTH: 48 nucleotides
(B) TYPE: nucleic acid
(C) STRANDEDNESS: single
(D) TOPOLOGY: linear -continued ( i i ) MOLECULE TYPE: DNA primer TAFI285

( i i i ) HYPOTHETICAL: NO ( i v ) ANTI-SENSE: NO ( x i ) SEQUENCE DESCRIPTION: SEQ ID NO:37:

GTCGGCATAT GATTAAAGAA CTTAATTTAC AAGAAAAATT AGAAAAGG 48

( 2 ) INFORMATION FOR SEQ ID NO:38:

( i ) SEQUENCE CHARACTERISTICS:
( A ) LENGTH: 46 nucleotides
( B ) TYPE: nucleic acid
( C ) STRANDEDNESS: single
( D ) TOPOLOGY: linear ( i i ) MOLECULE TYPE: DNA primer TAFR01

( i i i ) HYPOTHETICAL: NO ( i v ) ANTI-SENSE: NO ( x i ) SEQUENCE DESCRIPTION: SEQ ID NO:38:

CCTTTACCCC AGGATCCTCA TTCCCACTCT TTTCCATAAT AAACAT 46

5' TO 3' EXONUCLEASE MUTATIONS OF THERMOSTABLE DNA POLYMERASES

CROSS-REFERENCE TO RELATED APPLICATIONS

This application is a continuation of application Ser. No. 07/977,434, filed Feb. 23, 1993, which is a continuation-in-part (CIP) of Ser. Nos. 07/590,213, now abandoned in favor of continuation application U.S. Ser. No. 08/119,754, filed Sep. 10, 1993, now U.S. Pat. No. 5,405,774, 07/590,466 now abandoned in favor of continuation application U.S. Ser. No. 08/113,531, filed Aug. 27, 1993, now U.S. Pat. No. 5,455,170 and 07/590,490 all of which were filed on Sep. 28, 1990, and all of which are CIPs of Ser. No. 07/523,394, filed May 15, 1990, which issued as U.S. Pat. No. 5,079,352 and which is a CIP of abandoned Ser. No. 07/143,441, filed Jan. 12, 1988, now abandoned in favor of continuation application U.S. Ser. No. 07/873,897, filed Apr. 24, 1992, and which is a CIP of Ser. No. 07/063,509, filed Jun. 17, 1987, which issued as U.S. Pat. No. 4,889,818 and which is a CIP of abandoned Ser. No. 06/899,241, filed Aug. 22, 1986.

Said Ser. No. 07/977,434 a also a CIP of Ser. No. 07/746,121 filed Aug. 15, 1991 now abandoned in favor of continuation application U.S. Ser. No. 08/082,182, filed Jun. 24, 1993, which issued as U.S. Pat. No. 5,310,652 and, which is a CIP of: 1) PCT/US90/07641, filed Dec. 21, 1990, which is a CIP of Ser. No. 07/585,471, filed Sep. 20, 1990, now abandoned in favor of U.S. Ser. No. 08/080,243, filed Jun. 17, 1993, which issued as U.S. Pat. No. 5,407,800, which is a CIP of Ser. No. 07/455,611, filed Dec. 22, 1989, which issued as U.S. Pat. No. 5,322,770 which is a CIP of Ser. No. 07/143,441, filed Jan. 12, 1988 now abandoned in favor of continuation application U.S. Ser. No. 07/873,897, filed Apr. 24, 1992, and its ancestors as described above; and 2) Ser. No. 07/609,157, filed Nov. 2, 1990 now abandoned, which is a CIP of Ser. No. 07/557,517, filed Jul. 24, 1990 now abandoned.

All of the patent applications referenced in this section are incorporated herein by reference.

BACKGROUND OF THE INVENTION

1. Field of the Invention

The present invention relates to thermostable DNA polymerases which have been altered or mutated such that a different level of 5' to 3' exonuclease activity is exhibited from that which is exhibited by the native enzyme. The present invention also relates to means for isolating and producing such altered polymerases. Thermostable DNA polymerases are useful in many recombinant DNA techniques, especially nucleic acid amplification by the polymerase chain reaction (PCR) self-sustained sequence replication (3SR), and high temperature DNA sequencing.

2. Background Art

Extensive research has been conducted on the isolation of DNA polymerases from mesophilic microorganisms such as *E. coli*. See, for example, Bessman et al., 1957, *J. Biol. Chem.* 223:171–177 and Buttin and Kornberg, 1966, *J. Biol. Chem.* 241:5419–5427.

Somewhat less investigation has been made on the isolation and purification of DNA polymerases from thermophiles such as *Thermus aquaticus, Thermus thermophilus, Thermotoga maritima*, Thermus species sps 17, Thermus species Z05 and *Thermosipho africanus*.

The use of thermostable enzymes to amplify existing nucleic acid sequences in amounts that are large compared to the amount initially present was described in U.S. Pat. Nos. 4,683,195 and 4,683,202, which describe the PCR process, both disclosures of which are incorporated herein by reference. Primers, template, nucleoside triphosphates, the appropriate buffer and reaction conditions, and polymerase are used in the PCR process, which involves denaturation of target DNA, hybridization of primers, and synthesis of complementary strands. The extension product of each primer becomes a template for the production of the desired nucleic acid sequence. The two patents disclose that, if the polymerase employed is a thermostable enzyme, then polymerase need not be added after every denaturation step, because heat will not destroy the polymerase activity.

U.S. Pat. No. 4,889,818, European Patent Publication No. 258,017 and PCT Publication No. 89/06691, the disclosures of which are incorporated herein by reference, all describe the isolation and recombinant expression of an ~94 kDa thermostable DNA polymerase from *Thermus aquaticus* and the use of that polymerase in PCR. Although *T. aquaticus* DNA polymerase is especially preferred for use in PCR and other recombinant DNA techniques, there remains a need for other thermostable polymerases.

SUMMARY OF THE INVENTION

In addressing the need for other thermostable polymerases, the present inventors found that some thermostable DNA polymerases such as that isolated from *Thermus aquaticus* (*Taq*) display a 5' to 3' exonuclease or structure-dependent single-stranded endonuclease (SDSSE) activity. As is explained in greater detail below, such 5' to 3' exonuclease activity is undesirable in an enzyme to be used in PCR, because it may limit the amount of product produced and contribute to the plateau phenomenon in the normally exponential accumulation of product. Furthermore, the presence of 5' to 3' nuclease activity in a thermostable DNA polymerase may contribute to an impaired ability to efficiently generate long PCR products greater than or equal to 10 kb particularly for G+C-rich targets. In DNA sequencing applications and cycle sequencing applitions, the presence of 5' to 3' nuclease activity may contribute to reduction in desired band intensities and/or generation of spurious or background bands. Finally, the absence of 5' to 3' nuclease activity may facilitate higher sensitivity allelic discrimination in a combined polymerase ligase chain reaction (PLCR) assay.

However, an enhanced or greater amount of 5' to 3' exonuclease activity in a thermostable DNA polymerase may be desirable in such an enzyme which is used in a homogeneous assay system for the concurrent amplification and detection of a target nucleic acid sequence. Generally, an enhanced 5' to 3' exonuclease activity is defined as an enhanced rate of exonuclease cleavage or an enhanced rate of nick-translation synthesis or by the displacement of a larger nucleotide fragment before cleavage of the fragment.

Accordingly, the present invention was developed to meet the needs of the prior art by providing thermostable DNA polymerases which exhibit altered 5' to 3' exonuclease activity. Depending on the purpose for which the thermostable DNA polymerase will be used, the 5' to 3' exonuclease activity of the polymerase may be altered such that a range of 5' to 3' exonuclease activity may be expressed. This range of 5' to 3' exonuclease activity extends from an enhanced activity to a complete lack of activity. Although enhanced activity is useful in certain PCR applications, e. g. a homogeneous assay, as little 5' to 3' exonuclease activity as possible is desired in thermostable DNA polymerases utilized in most other PCR applications.

It was also found that both site directed mutagenesis as well as deletion mutagenesis may result in the desired altered 5' to 3' exonuclease activity in the thermostable DNA polymerases of the present invention. Some mutations which alter the exonuclease activity have been shown to alter the processivity of the DNA polymerase. In many applications (e.g. amplification of moderate sized targets in the presence of a large amount of high complexity genomic DNA) reduced processivity may simplify the optimization of PCRs and contribute to enhanced specificity at high enzyme concentration. Some mutations which eliminate 5' to 3' exonuclease activity do not reduce and may enhance the processivity of the thermostable DNA polymerase and accordingly, these mutant enzymes may be preferred in other applications (e.g. generation of long PCR products). Some mutations which eliminate the 5' to 3' exonuclease activity simultaneously enhance, relative to the wild type, the thermoresistance of the mutant thermostable polymerase, and thus, these mutant enzymes find additional utility in the amplification of G+C-rich or otherwise difficult to denature targets.

Particular common regions or domains of thermostable DNA polymerase genomes have been identified as preferred sites for mutagenesis to affect the enzyme's 5' to 3' exonuclease. These domains can be isolated and inserted into a thermostable DNA polymerase having none or little natural 5' to 3' exonuclease activity to enhance its activity. Thus, methods of preparing chimeric thermostable DNA polymerases with altered 5' to 3' exonuclease are also encompassed by the present invention.

DETAILED DESCRIPTION OF THE INVENTION

The present invention provides DNA sequences and expression vectors that encode thermostable DNA polymerases which have been mutated to alter the expression of 5' to 3' exonuclease. To facilitate understanding of the invention, a number of terms are defined below.

The terms "cell", "cell line", and "cell culture" an be used interchangeably and all such designations include progeny. Thus, the words "transformants" or "transformed cells" include the primary transformed ell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly other sequences. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full length coding sequence or by any portion of the coding sequence so long as the enzymatic activity is retained.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The term "mixture" as it relates to mixtures containing thermostable polymerases refers to a collection of materials which includes a desired thermostable polymerase but which can also include other proteins. If the desired thermostable polymerase is derived from recombinant host cells, the other proteins will ordinarily be those associated with the host. Where the host is bacterial, the contaminating proteins will, of course, be bacterial proteins.

The term "non-ionic polymeric detergents" refers to surface-active agents that have no ionic charge and that are characterized for purposes of this invention, by an ability to stabilize thermostable polymerase enzymes at a pH range of from about 3.5 to about 9.5, preferably from 4 to 8.5.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be derived synthetically or by cloning.

The term "primer" as used herein refers to an oligonucleotide which is capable of acting as a point of initiation of synthesis when placed under conditions in which primer extension is initiated. An oligonucleotide "primer" may occur naturally, as in a purified restriction digest or be produced synthetically. Synthesis of a primer extension product which is complementary to a nucleic acid strand is initiated in the presence of four different nucleoside triphosphates and a thermostable polymerase enzyme in an appropriate buffer at a suitable temperature. A "buffer" includes cofactors (such as divalent metal ions) and salt (to provide the appropriate ionic strength), adjusted to the desired pH.

A primer is single-stranded for maximum efficiency in amplification, but may alternatively be double-stranded. If double-stranded, the primer is first treated to separate its strands before being used to prepare extension products. The primer is usually an oligodeoxyribonucleotide. The primer must be sufficiently long to prime the synthesis of extension products in the presence of the polymerase enzyme. The exact length of a primer will depend on many factors, such as source of primer and result desired, and the reaction temperature must be adjusted depending on primer length and nucleotide sequence to ensure proper annealing of primer to template. Depending on the complexity of the target sequence, an oligonucleotide primer typically contains 15 to 35 nucleotides. Short primer molecules generally require lower temperatures to form sufficiently stable complexes with template.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The terms "restriction endonucleases" and "restriction enzymes" refer to bacterial enzymes which cut double-stranded DNA at or near a specific nucleotide sequence.

The term "thermostable polymerase enzyme" refers to an enzyme which is stable to heat and is heat resistant and catalyzes (facilitates) combination of the nucleotides in the proper manner to form primer extension products that are complementary to a template nucleic acid strand. Generally, synthesis of a primer extension product begins at the 3' end of the primer and proceeds in the 5' direction along the template strand, until synthesis terminates.

In order to further facilitate understanding of the invention, specific thermostable DNA polymerase enzymes are referred to throughout the specification to exemplify the broad concepts of the invention, and these references are not intended to limit the scope of the invention. The specific enzymes which are frequently referenced are set forth below with a common abbreviation which will be used in the specification and their respective nucleotide and amino acid Sequence ID numbers.

| Thermostable DNA Polymerase | Common Abbr. | SEQ. ID NO: |
|---|---|---|
| *Thermus aquaticus* | Taq | SEQ ID NO: 1 (nuc)<br>SEQ ID NO: 2 (a.a.) |
| *Thermotoga maritima* | Tma | SEQ ID NO: 3 (nuc)<br>SEQ ID NO: 4 (a.a.) |
| Thermus species sps17 | Tsps17 | SEQ ID NO: 5 (nuc)<br>SEQ ID NO: 6 (a.a.) |
| Thermus species Z05 | TZ05 | SEQ ID NO: 7 (nuc)<br>SEQ ID NO: 8 (a.a.) |
| *Thermus thermophilus* | Tth | SEQ ID NO: 9 (nuc)<br>SEQ ID NO: 10 (a.a.) |
| *Thermosipho africanus* | Taf | SEQ ID NO: 11 (nuc)<br>SEQ ID NO: 12 (a.a.) |

As summarized above, the present invention relates to thermostable DNA polymerases which exhibit altered 5' to 3' exonuclease activity from that of the native polymerase. Thus, the polymerases of the invention exhibit either an enhanced 5' to 3' exonuclease activity or an attenuated 5' to 3' exonuclease activity from that of the native polymerase.

Thermostable DNA Polymerases With Attenuated 5' to 3' Exonuclease Activity

DNA polymerases often possess multiple functions.

In addition to the polymerization of nucleotides *E. coli* DNA polymerase I (pol I), for example, catalyzes the pyrophosphorolysis of DNA as well as the hydrolysis of phosphodiester bonds. Two such hydrolytic activities have been characterized for pol I; one is a 3' to 5' exonuclease activity and the other a 5' to 3' exonuclease activity. The two exonuclease activities 40 are associated with two different domains of the pol I molecule. However, the 5' to 3' exonuclease activity of pol I differs from that of thermostable DNA polymerases in that the 5' to 3' exonuclease activity of thermostable DNA polymerases has stricter structural requirements for the substrate on which it acts.

An appropriate and sensitive assay for the 5' to 3' exonuclease activity of thermostable DNA polymerases takes advantage of the discovery of the structural requirement of the activity. An important feature of the design of the assay is an upstream oligonucleotide primer which positions the polymerase appropriately for exonuclease cleavage of a labeled downstream oligonucleotide probe. For an assay of polymerization-independent exonuclease activity (i.e., an assay performed in the absence of deoxynucleoside triphosphates) the probe must be positioned such that the region of probe complementary to the template is immediately adjacent to the 3'-end of the primer.

Additionally, the probe should contain at least one, but preferably 2–10, or most preferably 3–5 nucleotides at the 5'-end of the probe which are not complementary to the template. The combination of the primer and probe when annealed to the template creates a double stranded structure containing a nick with a 3'-hydroxyl 5' of the nick, and a displaced single strand 3' of the nick. Alternatively, the assay can be performed as a polymerization-dependent reaction, in which case each deoxynucleoside triphosphate should be included at a concentration of between 1 μM and 2 mM, preferably between 10 μM and 200 μM, although limited dNTP addition (and thus limited dNTP inclusion) may be involved as dictated by the template sequence. When the assay is performed in the presence of dNTPs, the necessary structural requirements are an upstream oligonucleotide primer to direct the synthesis of the complementary strand of the template by the polymerase, and a labeled downstream oligonucleotide probe which will be contacted by the polymerase in the process of extending the upstream primer. An example of a polymerization-independent thermostable DNA polymerase 5' to 3' exonuclease assay follows.

The synthetic 3' phosphorylated oligonucleotide probe (phosphorylated to preclude polymerase extension) BW33 (GATCGCTGCGCGTAACCACCACACCCGCCGCGCp) (SEQ ID NO:13) (100 pmol) was $^{32}$P-labeled at the 5' end with gamma-[$^{32}$P] ATP (3000 Ci/mmol) and T4 polynucleotide kinase. The reaction mixture was extracted with phenol:chloroform:isoamyl alcohol, followed by ethanol precipitation. The $^{32}$P-labeled oligonucleotide probe was redissolved in 100 μl of TE buffer, and unincorporated ATP was removed by gel filtration chromatography on a Sephadex G-50 spin column. Five pmol of $^{32}$P-labeled BW33 probe, was annealed to 5 pmol of single-strand M13mp10w DNA, in the presence of 5 pmol of the synthetic oligonucleotide primer BW37 (GCGCTAGGGCGCTGGCAAGTGTAGCGGTCA) (SEQ ID NO:14) in a 100 μl reaction containing 10 mM Tris-HCl (pH 8.3), 50 mM KCl, and 3 mM $MgCl_2$. The annealing mixture was heated to 95° C. for 5 minutes, cooled to 70° C. over 10 minutes, incubated at 70° C. for an additional 10 minutes, and then cooled to 25° C. over a 30 minute period in a Perkin-Elmer Cetus DNA Thermal Cycler. Exonuclease reactions containing 10 μl of the annealing mixture were pre-incubated at 70° C. for 1 minute. Thermostable DNA polymerase enzyme (approximately 0.01 to 1 unit of DNA polymerase activity, or 0.0005 to 0.05 pmol of enzyme) was added in a 2.5 μl volume to the pre-incubation reaction, and the reaction mixture was incubated at 70° C. Aliquots (5 μl) were removed after 1 minute and 5 minutes, and stopped by the addition of 1 μl of 60 mM EDTA. The reaction products were analyzed by homochromatography and exonuclease activity was quantified following autoradiography. Chromatography was carried out in a homochromatography mix containing 2% partially hydrolyzed yeast RNA in 7M urea on Polygram CEL 300 DEAE cellulose thin layer chromatography plates. The presence of 5' to 3' exonuclease activity results in the generation of small $^{32}$P-labeled oligomers, which migrate up the TLC plate, and are easily differentiated on the autoradiogram from undegraded probe, which remains at the origin.

The 5' to 3' exonuclease activity of the thermostable DNA polymerases excises 5' terminal regions of double-stranded DNA releasing 5'-mono- and oligonucleotides in a sequential manner. The preferred substrate for the exonuclease is displaced single-stranded DNA, with hydrolysis of the phosphodiester bond occurring between the displaced single-stranded DNA and the double-helical DNA. The preferred exonuclease cleavage site is a phosphodiester bond in the double helical region. Thus, the exonuclease activity can be better described as a structure-dependent single-stranded endonuclease (SDSSE).

Many thermostable polymerases exhibit this 5' to 3' exonuclease activity, including the DNA polymerases of *Taq*, *Tma*, Tsps17, TZ05, *Tth* and *Taf*. When thermostable polymerases which have 5' to 3' exonuclease activity are utilized in the PCR process, a variety of undesirable results have been observed including a limitation of the amount of product produced, an impaired ability to generate long PCR products or amplify regions containing significant secondary structure, the production of shadow bands or the attenuation in signal strength of desired termination bands during DNA sequencing, the degradation of the 5'-end of oligonucleotide primers in the context of double-stranded primer-template complex, nick-translation synthesis during oligonucleotide-directed mutagenesis and the degradation of the RNA component of RNA:DNA hybrids.

The limitation of the amount of PCR product produced is attributable to a plateau phenomenon in the otherwise exponential accumulation of product. Such a plateau phenomenon occurs in part because 5' to 3' exonuclease activity causes-the hydrolysis or cleavage of phosphodiester bonds when a polymerase with 5' to 3' exonuclease activity encounters a forked structure on a PCR substrate.

Such forked structures commonly exist in certain G- and C-rich DNA templates. The cleavage of these phosphodiester bonds under these circumstances is undesirable as it precludes the amplification of certain G- and C-rich targets by the PCR process. Furthermore, the phosphodiester bond cleavage also contributes to the plateau phenomenon in the generation of the later cycles of PCR when product strand concentration and renaturation kinetics result in forked structure substrates.

In the context of DNA sequencing, the 5' to 3' exonuclease activity of DNA polymerases is again a hinderance with forked structure templates because the phosphodiester bond cleavage during the DNA extension reactions results in "false stops". These "false stops" in turn contribute to shadow bands, and in extreme circumstances may result in the absence of accurate and interpretable sequence data.

When utilized in a PCR process with double-stranded primer-template complex, the 5' to 3' exonuclease activity of a DNA polymerase may result in the degradation of the 5'-end of the oligonucleotide primers. This activity is not only undesirable in PCR, but also in second-strand cDNA synthesis and sequencing processes.

During optimally efficient oligonucleotide-directed mutagenesis processes, the DNA polymerase which is utilized must not have strand-displacement synthesis and/or nick-translation capability. Thus, the presence of 5' to 3' exonuclease activity in a polymerase used for oligonucleotide-directed mutagenesis is also undesirable.

Finally, the 5' to 3' exonuclease activity of polymerases generally also contains an inherent RNase H activity. However, when the polymerase is also to be used as a reverse transcriptase, as in a PCR process including an RNA:DNA hybrid, such an inherent RNase H activity may be disadvantageous.

Thus, one aspect of this invention involves the generation of thermostable DNA polymerase mutants displaying greatly reduced, attenuated or completely eliminated 5' to 3' exonuclease activity. Such mutant thermostable DNA polymerases will be more suitable and desirable for use in processes such as PCR, second-strand cDNA synthesis, sequencing and oligonucleotide-directed mutagenesis.

The production of thermostable DNA polymerase mutants with attenuated or eliminated 5' to 3' exonuclease activity may be accomplished by processes such as site-directed mutagenesis and deletion mutagenesis.

For example, a site-directed mutation of G to A in the second position of the codon for Gly at residue 46 in the *Taq* DNA polymerase amino acid sequence (i.e. mutation of G(137) to A in the DNA sequence has been found to result in an approximately 1000-fold reduction of 5' to 3' exonuclease activity with no apparent change in polymerase activity, processivity or extension rate. This site-directed mutation of the *Taq* DNA polymerase nucleotide sequence results in an amino acid change of Gly (46) to Asp.

Glycine 46 of *Taq* DNA polymerase is conserved in Thermus species sps17 DNA polymerase, but is located at residue 43, and the same Gly to Asp mutation has a similar effect on the 5' to 3' exonuclease activity of Tsps17 DNA polymerase. Such a mutation of the conserved Gly of *Tth* (Gly 46), TZ05 (Gly 46), *Tma* (Gly 37) and *Taf* (Gly 37) DNA polymerases to Asp also has a similar attenuating effect on the 5' to 3' exonuclease activities of those polymerases.

*Tsps*17 Gly 43, *Tth* Gly 46, TZ05 Gly 46, *Taf* Gly 37 and *Tma* Gly 37 are also found in a conserved A(V/T)YG (SEQ ID NO:15) sequence domain, and changing the glycine to aspartic acid within this conserved sequence domain of any polymerase is also expected to attenuate 5' to 3' exonuclease activity. Specifically, *Tsps*17 Gly 43, *Tth* Gly 46, TZ05 Gly 46, and *Taf* Gly 37 share the AVYG sequence domain, and *Tma* Gly 37 is found in the ATYG domain. Mutations of glycine to aspartic acid in other thermostable DNA polymerases containing the conserved A(V/T)YG (SEQ ID NO:15) domain can be accomplished utilizing the same principles and techniques used for the site-directed mutagenesis of *Taq* polymerase. Exemplary of such site-directed mutagenesis techniques are Example 5 of U.S. Ser. No. 523,394, filed May 15, 1990, which issued as U.S. Pat. No. 5,079,352, PCT/US91/07076, which published on Apr. 16, 1992, Docket No. 2583.1 filed Sep. 27, 1991, Examples 4 and 5 of U.S. Ser. No. 455,967, filed Dec. 22, 1989, which was filed in the PCT as PCT/US90/07639, and which published on Jul. 11, 1991, and Examples 5 and 8 of PCT Application No. 91/05753, filed Aug. 13, 1991, which published on Mar. 5, 1992, each of which are incorporated herein by reference.

Such site-directed mutagenesis is generally accomplished by site-specific primer-directed mutagenesis. This technique is now standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phasmid or phage, and the resulting double-stranded DNA is transformed into a phage-supporting host bacterium. Cultures of the transformed bacteria are plated in top agar, permitting plaque formation from single cells that harbor the phage or plated on drug selective media for phasmid vectors.

Theoretically, 50% of the new plaques will contain the phage having, as a single strand, the mutated form; 50% will have the original sequence. The plaques are transferred to nitrocellulose filters and the "lifts" hybridized with kinased synthetic primer at a temperature that permits hybridization of an exact match, but at which the mismatches with the original strand are sufficient to prevent hybridization. Plaques that hybridize with the probe are then picked and cultured, and the DNA is recovered.

In the constructions set forth below, correct ligations for plasmid construction are confirmed by first transforming *E. coli* strains DG98, DG101, DG116, or other suitable hosts, with the ligation mixture. Successful transformants are selected by ampicillin, tetracycline or other antibiotic resistance or using other markers, depending on the mode of plasmid construction, as is understood in the art. Plasmids from the transformants are then prepared according to the method of Clewell, D. B., et al., *Proc. Natl. Acad. Sci.* (USA) (1969) 62:1159, optionally following chloramphenicol amplification (Clewell, D. B., *J. Bacteriol.* (1972) 110: 667). The isolated DNA is analyzed by restriction and/or sequenced by the dideoxy method of Sanger, F., et al., *Proc. Natl. Acad. Sci.* (*USA*) (1977) 74:5463 as further described by Messing, et al., *Nucleic Acids Res.* (1981) 9:309, or by the method of Maxam, et al., *Methods in Enzymology* (1980) 65:499.

For cloning and sequencing, and for expression of constructions under control of most lac or $P_L$ promoters, *E. coli* strains DG98, DG101, DG116 were used as the host. For expression under control of the $P_LN_{RBS}$ promoter, *E. coli* strain K12 MC1000 lambda lysogen, $N_7N_{53}cI857$ $SusP_{80}$, ATCC 39531 may be used. Exemplary hosts used herein for expression of the thermostable DNA polymerases with altered 5' to 3' exonuclease activity are *E. coli* DG116, which was deposited with ATCC (ATCC 53606) on Apr. 7, 1987 and *E. coli* KB2, which was deposited with ATCC (ATCC 53075) on Mar. 29, 1985.

For M13 phage recombinants, *E. coli* strains susceptible to phage infection, such as *E. coli* K12 strain DG98, are employed. The DG98 strain has been deposited with ATCC Jul. 13, 1984 and has accession number 39768.

Mammalian expression can be accomplished in COS-7 COS-A2, CV-1, and murine cells, and insect cell-based expression in *Spodoptera frugipeida.*

The thermostable DNA polymerases of the present invention are generally purified from *E. coli* strain DG116 containing the features of plasmid pLSG33. The primary features are a temperature regulated promoter ($\lambda P_L$ promoter), a temperature regulated plasmid vector, a positive retroregulatory element (PRE) (see U.S. Pat. No. 4,666,848, issued May 19, 1987), and a modified form of a thermostable DNA polymerase gene. As described at page 46 of the specification of U.S patent application Ser. No. 455,967, which was filed in the PCT as PCT/US90/07639, and which published on Jul. 11, 1991, pLSG33 was prepared by ligating the NdeI-BamHI restriction fragment of pLSG24 into expression vector pDG178. The resulting plasmids are ampicillin resistant and capable of expressing 5' to 3' exonuclease deficient forms of the thermostable DNA polymerases of the present invention. The seed flask for a 10 liter fermentation contains tryptone (20 g/l), yeast extract (10 g/l), NaCl (10 g/l) and 0.005% ampicillin. The seed flask is inoculated from colonies from an agar plate, or a frozen glycerol culture stock can be used. The seed is grown to between 0.5 and 1.0 O.D. ($A_{680}$). The volume of seed culture inoculated into the fermentation is calculated such that the final concentration of bacteria will be 1 mg dry weight/liter. The 10 liter growth medium contained 25 mM $KH_2PO_4$, 10 mM $(NH_4)_2SO_4$, 4 mM sodium citrate, 0.4 mM $FeCl_2$, 0.04 mM $ZnCl_2$, 0.03 mM $CoCl_2$, 0.03 mM $CuCl_2$, and 0.03 mM $H_3BO_3$. The following sterile components are added: 4 mM $MgSO_4$, 20 g/l glucose, 20 mg/l thiamine-HCl and 50 mg/l ampicillin. The pH was adjusted to 6.8 with NaOH and controlled during the fermentation by added $NH_4OH$. Glucose is continually added during the fermentation by coupling to $NH_4OH$ addition. Foaming is controlled by the addition of polypropylene glycol as necessary, as an antifoaming agent. Dissolved oxygen concentration is maintained at 40%.

The fermentation is inoculated as described above and the culture is grown at 30° C. until an optical density of 21 ($A_{680}$) is reached. The temperature is then raised to 37° C. to induce synthesis of the desired polymerase. Growth continues for eight hours after induction, and the cells are then harvested by concentration using cross flow filtration followed by centrifugation. The resulting cell paste is frozen at −70° C. and yields about 500 grams of cell paste. Unless otherwise indicated, all purification steps are conducted at 4° C.

A portion of the frozen (−70° C.) *E. coli* K12 strain DG116 harboring plasmid pLSG33 or other suitable host as described above is warmed overnight to −20° C. To the cell pellet the following reagents are added: 1 volume of 2× TE (100 mM Tris-HCl, pH 7.5, 20 mM EDTA), 1 mg/ml leupeptin and 144 mM PMSF (in dimethyl formamide). The final concentration of leupeptin was 1 μg/ml and for PMSF, 2.4 mM. Preferably, dithiothreitol (DTT) is included in TE to provide a final concentration of 1 mM DTT. The mixture is homogenized at low speed in a blender. All glassware is baked prior to use, and solutions used in the purification are autoclaved, if possible, prior to use. The cells are lysed by passage twice through a Microfluidizer at 10,000 psi.

The lysate is diluted with 1× TE containing 1 mM DTT to a final volume of 5.5× cell wet weight. Leupeptin is added to 1 μg/ml and PMSF is added to 2.4 mM. The final volume (Fraction I) is approximately 1540 ml.

Ammonium sulfate is gradually added to 0.2M (26.4 g/l) and the lysate stirred. Upon addition of ammonium sulfate, a precipitate forms which is removed prior to the polyethylenimine (PEI) precipitation step, described below. The ammonium sulfate precipitate is removed by centrifugation of the suspension at 15,000–20,000×g in a JA-14 rotor for 20 minutes. The supernatant is decanted and retained. The ammonium sulfate supernatant is then stirred on a heating plate until the supernatant reaches 75° C. and then is placed in a 77° C. bath and held there for 15 minutes with occasional stirring. The supernatant is then cooled in an ice bath to 20° C. and a 10 ml aliquot is removed for PEI titration.

PEI titration and agarose gel electrophoresis are used to determine that 0.3% PEI (commercially available from BDH as PolyminP) precipitates ~90% of the macromolecular DNA and RNA, i.e., no DNA band is visible on an ethidium bromide stained agarose gel after treatment with PEI. PEI is added slowly with stirring to 0.3% from a 10% stock solution. The PEI treated supernatant is centrifuged at 10,000 RPM (17,000×g) for 20 minutes in a JA-14 rotor. The supernatant is decanted and retained. The volume (Fraction II) is approximately 1340 ml.

Fraction II is loaded onto a 2.6×13.3 cm (71 ml) phenyl sepharose CL-4B (Pharmacia-LKB) column following equilibration with 6 to 10 column volumes of TE containing 0.2M ammonium sulfate. Fraction II is then loaded at a linear flow rate of 10 cm/hr. The flow rate is 0.9 ml/min. The column is washed with 3 column volumes of the equilibration buffer and then with 2 column volumes of TE to remove contaminating non-DNA polymerase proteins. The recombinant thermostable DNA polymerase is eluted with 4 column volumes of 2.5M urea in TE containing 20% ethylene glycol. The DNA polymerase containing fractions are identified by optical absorption ($A_{280}$), DNA polymerase activity assay and SDS-PAGE according to standard procedures. Peak fractions are pooled and filtered through a 0.2 micron sterile vacuum filtration apparatus. The volume (Fraction III) is approximately 195 ml. The resin is equilibrated and recycled according to the manufacturer's recommendations.

A 2.6×1.75 cm (93 ml) heparin sepharose Cl-6B column (Pharmacia-LKB) is equilibrated with 6–10 column volumes of 0.05M KCl, 50 mM Tris-HCl, pH 7.5, 0.1 mM EDTA and 0.2% Tween 20 , at 1 column volume/hour. Preferably, the buffer contains 1 mM DTT. The column is washed with 3 column volumes of the equilibration buffer. The desired thermostable DNA polymerase of the invention is eluted with a 10 column volume linear gradient of 50–750 mM KCl gradient in the same buffer. Fractions (one-tenth column volume) are collected in sterile tubes and the fractions containing the desired thermostable DNA polymerase are pooled (Fraction IV, volume 177 ml).

Fraction IV is concentrated to 10 ml on an Amicon YM30 membrane. For buffer exchange, diafiltration is done 5 times with 2.5× storage buffer (50 mM Tris-HCl, pH 7.5, 250 mM KCl, 0.25 mM EDTA 2.5 mM DTT and 0.5% Tween-20 ) by filling the concentrator to 20 ml and concentrating the volumes to 10 ml each time. The concentrator is emptied and rinsed with 10 ml 2.5× storage buffer which is combined with the concentrate to provide Fraction V.

Anion exchange chromatography is used to remove residual DNA. The procedure is conducted in a biological safety hood and sterile techniques are used. A Waters Sep-Pak plus QMA cartridge with a 0.2 micron sterile disposable syringe tip filter unit is equilibrated with 30 ml of 2.5× storage buffer using a syringe at a rate of about 5 drops per second. Using a disposable syringe, Fraction V is passed through the cartridge at about 1 drop/second and collected in a sterile tube. The cartridge is flushed with 5 ml of 2.5 ml storage buffer and pushed dry with air. The eluant is diluted 1.5 × with 80% glycerol and stored at −20° C. The resulting final Fraction VI pool contains active thermostable DNA polymerase with altered 5' to 3' exonuclease activity.

In addition to site-directed mutagenesis of a nucleotide sequence, deletion mutagenesis techniques may also be used to attenuate the 5' to 3' exonuclease activity of a thermostable DNA polymerase. One example of such a deletion mutation is the deletion of all amino terminal amino acids up to and including the glycine in the conserved A(V/T)YG (SEQ ID NO:15) domain of thermostable DNA polymerases.

A second deletion mutation affecting 5' to 3' exonuclease activity is a deletion up to Ala 77 in *Taq* DNA polymerase. This amino acid (Ala 77) has been identified as the amino terminal amino acid in an approximately 85.5 kDa proteolytic product of *Taq* DNA polymerase. This proteolytic product has been identified in several native *Taq* DNA polymerase preparations and the protein appears to be stable. Since such a deletion up to Ala 77 includes Gly 46, it will also affect the 5' to 3' exonuclease activity of *Taq* DNA polymerase.

However, a deletion mutant beginning with Ala 77 has the added advantage over a deletion mutant beginning with phenylalanine 47 in that the proteolytic evidence suggests that the peptide will remain stable. Furthermore, Ala 77 is found within the sequence HEAYG (SEQ ID NO:16) 4 amino acids prior to the sequence YKA in *Taq* DNA polymerase. A similar sequence motif HEAYE (SEQ ID NO:17) is found in *Tth* DNA polymerase, TZ05 DNA polymerase and Tsps17 DNA polymerase. The alanine is 4 amino acids prior to the conserved motif YKA. The amino acids in the other exemplary thermostable DNA polymerases which correspond to *Taq* Ala 77 are *Tth* Ala 78, TZ05 Ala 78, Tsps17 Ala 74, *Tma* Leu 72 and *Taf* Ile 73. A deletion up to the alanine or corresponding amino acid in the motif HEAY(G/E) (SEQ ID NO:16 or SEQ ID NO:17) in a Thermus species thermostable DNA polymerase containing this sequence will attenuate its 5' to 3' exonuclease activity. The 5' to 3' exonuclease motif YKA is also conserved in *Tma* DNA polymerase (amino acids 76–78) and *Taf* DNA polymerase (amino acids 77–79). In this thermostable polymerase family, the conserved motif (L/I)LET (SEQ ID NO:18) immediately proceeds the YKA motif. *Taf* DNA polymerase Ile 73 is 4 residues prior to this YKA motif while TMA DNA polymerase Leu 72 is 4 residues prior to the YKA motif. A deletion of the Leu or Ile in the motif (L/I)LETYKA (SEQ ID NO:19) in a thermostable DNA polymerase from the Thermotoga or Thermosipho genus will also attenuate 5' to 3' exonuclease activity.

Thus, a conserved amino acid sequence which defines the 5' to 3' exonuclease activity of DNA polymerases of the Thermus genus as well as those of Thermotoga and Thermosipho has been identified as (I/L/A)$X_3$YKA (SEQ ID NO:20), wherein $X_3$ is any sequence of three amino acids. Therefore, the 5' to 3' exonuclease activity of thermostable DNA polymerases may also be altered by mutating this conserved amino acid domain.

Those of skill in the art recognize that when such a deletion mutant is to be expressed in recombinant host cells, a methionine codon is usually placed at the 5' end of the coding sequence, so that the amino terminal sequence of the deletion mutant protein would be MET-ALA in the Thermus genus examples above.

The preferred techniques for performing deletion mutations involve utilization of known restriction sites on the nucleotide sequence of the thermostable DNA polymerase. Following identification of the particular amino acid or amino acids which are to be deleted, a restriction site is identified which when cleaved will cause the cleavage of the target DNA sequence at a position or slightly 3' distal to the position corresponding to the amino acid or domain to be deleted, but retains domains which code for other properties of the polymerase which are desired.

Alternatively, restriction sites on either side (5' or 3') of the sequence coding for the target amino acid or domain may be utilized to cleave the sequence. However, a ligation of the two desired portions of the sequence will then be necessary. This ligation may be performed using techniques which are standard in the art and exemplified in Example 9 of Ser. No. 523,394, filed May 15, 1990, which issued as U.S. Pat. No. 5,079,352, Example 7 of PCT Application No. 91/05753, filed Aug. 13, 1991 which published on Mar. 5, 1992, and Ser. No. 590,490, filed Sep. 28, 1990, all of which are incorporated herein by reference.

Another technique for achieving a deletion mutation of the thermostable DNA polymerase is by utilizing the PCR mutagenesis process. In this process, primers are prepared which incorporate a restriction site and optionally a methionine codon if such a codon is not already present. Thus, the product of the PCR with this primer may be digested with an appropriate restriction enzyme to remove the domain which codes for 5' to 3' exonuclease activity of the enzyme. Then, the two remaining sections of the product are ligated to form the coding sequence for a thermostable DNA polymerase lacking 5' to 3' exonuclease activity. Such coding sequences can be utilized in expression vectors in appropriate host cells to produce the desired thermostable DNA polymerase lacking 5' to 3' exonuclease activity.

In addition to the *Taq* DNA polymerase mutants with reduced 5' to 3' exonuclease activity, it has also been found that a truncated *Tma* DNA polymerase with reduced 5' to 3' exonuclease activity may be produced by recombinant techniques even when the complete coding sequence of the *Tma* DNA polymerase gene is present in an expression vector in *E. coli*. Such a truncated *Tma* DNA polymerase is formed by translation starting with the methionine codon at position 140. Furthermore, recombinant means may be used to produce a truncated polymerase corresponding to the protein produced by initiating translation at the methionine codon at position 284 of the *Tma* coding sequence.

The *Tma* DNA polymerase lacking amino acids 1 though 139 (about 86 kDa), and the *Tma* DNA polymerase lacking amino acids 1 through 283 (about 70 kDa) retain polymerase activity but have attenuated 5' to 3' exonuclease activity. An additional advantage of the 70 kDa *Tma* DNA polymerase is that it is significantly more thermostable than native *Tma* polymerase.

Thus, it has been found that the entire sequence of the intact *Tma* DNA polymerase enzyme is not required for activity. Portions of the *Tma* DNA polymerase coding sequence can be used in recombinant DNA techniques to produce a biologically active gene product with DNA polymerase activity.

Furthermore, the availability of DNA encoding the *Tma* DNA polymerase sequence provides the opportunity to modify the coding sequence so as to generate mutein (mutant protein) forms also having DNA polymerase activity but with attenuated 5' to 3' exonuclease activity. The amino(N)-terminal portion of the *Tma* DNA polymerase is not necessary for polymerase activity but rather encodes the 5' to 3' exonuclease activity of the protein.

Thus, using recombinant DNA methodology, one can delete approximately up to one-third of the N-terminal coding sequence of the *Tma* gene, clone, and express a gene product that is quite active in polymerase assays but, depending on the extent of the deletion, has no 5' to 3' exonuclease activity. Because certain N-terminal shortened forms of the polymerase are active, the gene constructs used for expression of these polymerases can include the corresponding shortened forms of the coding sequence.

In addition to the N-terminal deletions, individual amino acid residues in the peptide chain of *Tma* DNA polymerase or other thermostable DNA polymerases may be modified by oxidation, reduction, or other derivation, and the protein may be cleaved to obtain fragments that retain polymerase activity but have attenuated 5' to 3' exonuclease activity. Modifications to the primary structure of the *Tma* DNA polymerase coding sequence or the coding sequences of other thermostable DNA polymerases by deletion, addition, or alteration so as to change the amino acids incorporated into the thermostable DNA polymerase during translation of the mRNA produced from that coding sequence can be made without destroying the high temperature DNA polymerase activity of the protein.

Another technique for preparing thermostable DNA polymerases containing novel properties such as reduced or enhanced 5' to 3' exonuclease activity is a "domain shuffling" technique for the construction of "thermostable chimeric DNA polymerases". For example, substitution of the *Tma* DNA polymerase coding sequence comprising codons about 291 through about 484 for the *Taq* DNA polymerase I codons 289–422 would yield a novel thermostable DNA polymerase containing the 5' to 3' exonuclease domain of *Taq* DNA polymerase (1–289), the 3' to 5' exonuclease domain of *Tma* DNA polymerase (291–484), and the DNA polymerase domain of *Taq* DNA polymerase (423–832). Alternatively, the 5' to 3' exonuclease domain and the 3' to 5' exonuclease domains of *Tma* DNA polymerase (ca. codons 1–484) may be fused to the DNA polymerase (dNTP binding and primer/template binding domains) portions of *Taq* DNA polymerase (ca. codons 423–832).

As is apparent, the donors and recipients for the creation of "thermostable chimeric DNA polymerase" by "domain shuffling" need not be limited to *Taq* and *Tma* DNA polymerases. Other thermostable polymerases provide analogous domains as *Taq* and *Tma* DNA polymerases. Furthermore, the 5' to 3' exonuclease domain may derive from a thermostable DNA polymerase with altered 5' to 3' nuclease activity. For example, the 1 to 289 5' to 3' nuclease domain of *Taq* DNA polymerase may derive from a Gly (46) to Asp mutant form of the *Taq* polymerase gene. Similarly, the 5' to 3' nuclease and 3' to 5' nuclease domains of *Tma* DNA polymerase may encode a 5' to 3' exonuclease deficient domain, and be retrieved as a *Tma* Gly (37) to Asp amino acid 1 to 484 encoding DNA fragment or alternatively a truncated Met 140 to amino acid 484 encoding DNA fragment.

While any of a variety of means may be used to generate chimeric DNA polymerase coding sequences (possessing novel properties), a preferred method employs "overlap" PCR. In this method, the intended junction sequence is designed into the PCR primers (at their 5'-ends). Following the initial amplification of the individual domains, the various products are diluted (ca. 100 to 1000-fold) and combined, denatured, annealed, extended, and then the final forward and reverse primers are added for an otherwise standard PCR.

Those of skill in the art recognize that the above thermostable DNA polymerases with attenuated 5' to 3' exonuclease activity are most easily constructed by recombinant DNA techniques. When one desires to produce one of the mutant enzymes of the present invention, with attenuated 5' to 3' exonuclease activity or a derivative or homologue of those enzymes, the production of a recombinant form of the enzyme typically involves the construction of an expression vector, the transformation of a host cell with the vector, and culture of the transformed host cell under conditions such that expression will occur.

To construct the expression vector, a DNA is obtained that encodes the mature (used here to include all chimeras or muteins) enzyme or a fusion of the mutant polymerase to an additional sequence that does not destroy activity or to an additional sequence cleavable under controlled conditions (such as treatment with peptidase) to give an active protein. The coding sequence is then placed in operable linkage with suitable control sequences in an expression vector. The vector can be designed to replicate autonomously in the host cell or to integrate into the chromosomal DNA of the host cell. The vector is used to transform a suitable host, and the transformed host is cultured under conditions suitable for expression of the recombinant polymerase.

Each of the foregoing steps can be done in a variety of ways. For example, the desired coding sequence may be obtained from genomic fragments and used directly in appropriate hosts. The construction for expression vectors operable in a variety of hosts is made using appropriate replicons and control sequences, as set forth generally below. Construction of suitable vectors containing the desired coding and control sequences employs standard ligation and restriction techniques that are well understood in the art. Isolated plasmids, DNA sequences, or synthesized oligonucleotides are cleaved, modified, and religated in the form desired. Suitable restriction sites can, if not normally available, be added to the ends of the coding sequence so as to facilitate construction of an expression vector, as exemplified below.

Site-specific DNA cleavage is performed by treating with suitable restriction enzyme (or enzymes) under conditions that are generally understood in the art and specified by the manufacturers of commercially available restriction enzymes. See, e.g., New England Biolabs, Product Catalog. In general, about 1 μg of plasmid or other DNA is cleaved by one unit of enzyme in about 20 μl of buffer solution; in the examples below, an excess of restriction enzyme is generally used to ensure complete digestion of the DNA. Incubation times of about one to two hours at about 37° C. are typical, although variations can be tolerated. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., *Methods in Enzymology*, 1980, 65:499–560.

Restriction-cleaved fragments with single-strand "overhanging" termini can be made blunt-ended (double-strand ends) by treating with the large fragment of *E. coli* DNA polymerase I (Klenow) in the presence of the four deoxynucleoside triphosphates (dNTPs) using incubation times of about 15 to 25 minutes at 20° C. to 25° C. in 50 mM Tris-Cl pH 7.6, 50 mM NaCl, 10 mM $MgCl_2$, 10 mM DTT, and 5 to 10 μM dNTPs. The Klenow fragment fills in at 5' protruding ends, but chews back protruding 3' single strands, even though the four dNTPs are present. If desired, selective repair can be performed by supplying only one of the, or selected, dNTPs within the limitations dictated by the nature of the protruding ends. After treatment with Klenow, the mixture is extracted with phenol/chloroform and ethanol precipitated. Similar results can be achieved using S1 nuclease, because treatment under appropriate conditions with S1 nuclease results in hydrolysis of any single-stranded portion of a nucleic acid.

Synthetic oligonucleotides can be prepared using the triester method of Matteucci et al., 1981, *J. Am. Chem. Soc.* 103:3185–3191, or automated synthesis methods. Kinasing of single strands prior to annealing or for labeling is achieved using an excess, e.g., approximately 10 units, of polynucleotide kinase to 0.5 μM substrate in the presence of 50 mM Tris, pH 7.6, 10 mM $MgCl_2$, 5 mM dithiothreitol (DTT), and 1 to 2 μM ATP. If kinasing is for labeling of probe, the ATP will contain high specific activity $\gamma$-$^{32}P$.

Ligations are performed in 15–30 μl volumes under the following standard conditions and temperatures: 20 mM Tris-Cl, pH 7.5, 10 mM $MgCl_2$, 10 mM DTT, 33 μg/ml BSA, 10 mM-50 mM NaCl, and either 40 μM ATP and 0.01–0.02 (Weiss) units T4 DNA ligase at 0° C. (for ligation of fragments with complementary single-stranded ends) or 1 mM ATP and 0.3–0.6 units T4 DNA ligase at 14° C. (for "blunt end" ligation). Intermolecular ligations of fragments with complementary ends are usually performed at 33–100 μg/ml total DNA concentrations (5 to 100 nM total ends concentration). Intermolecular blunt end ligations (usually employing a 20 to 30 fold molar excess of linkers, optionally) are performed at 1 μM total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and published protocols usually accompany the commercially available BAP and CIAP enzymes. To recover the nucleic acid fragments, the preparation is extracted with phenol-chloroform and ethanol precipitated to remove the phosphatase and purify the DNA. Alternatively, religation of unwanted vector fragments can be prevented by restriction enzyme digestion before or after ligation, if appropriate restriction sites are available.

For portions of vectors or coding sequences that require sequence modifications, a variety of site-specific primer-directed mutagenesis methods are available. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence of a single-stranded vector, such as pBS13+, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic primer at a temperature that permits hybridization of an exact match to the modified sequence but prevents hybridization with the original strand. Transformants that contain DNA that hybridizes with the probe are then cultured and serve as a reservoir of the modified DNA.

In the constructions set forth below, correct ligations for plasmid construction are confirmed by first transforming *E. coli* strain DG101 or another suitable host with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, *Proc. Natl. Acad. Sci. USA* 62:1159, optionally following chloramphenicol amplification (Clewell, 1972, *J. Bacteriol.* 110:667). Another method for obtaining plasmid DNA is described as the "Base-Acid" extraction method at page 11 of the Bethesda Research Laboratories publication *Focus*, volume 5, number 2, and very pure plasmid DNA can be obtained by replacing steps 12 through 17 of the protocol with CsCl/ethidium bromide ultracentrifugation of the DNA. The isolated DNA is analyzed by restriction enzyme digestion and/or sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499.

The control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are therefore preferred for the expression of the thermostable DNA polymerases of the present invention.

The procaryote most frequently used to express recombinant proteins is *E. coli*. For cloning and sequencing, and for expression of constructions under control of most bacterial promoters, *E. coli* K12 strain MM294, obtained from the *E. coli* Genetic Stock Center under GCSC #6135, can be used as the host. For expression vectors with the $P_LN_{RBS}$ control sequence, *E. coli* K12 strain MC1000 lambda lysogen, $N_7N_{53}cI_{857}$ $SusP_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98, are employed. The DG98 strain was deposited with the ATCC (ATCC 39768) on Jul. 13, 1984.

However, microbial strains other than *E. coli* can also be used, such as bacilli, for example *Bacillus subtilis*, various species of Pseudomonas, and other bacterial strains, for recombinant expression of the thermostable DNA polymerases of the present invention. In such procaryotic systems, plasmid vectors that contain replication sites and control sequences derived from the host or a species compatible with the host are typically used.

For example, *E. coli* is typically transformed using derivatives of pBR322, described by Bolivar et al., 1977, Gene 2:95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β-lactamase (penicillinase) and lactose (lac) promoter systems (Chang et al., 1977, *Nature* 198:1056), the tryptophan (trp) promoter system (Goeddel et al., 1980, *Nuc. Acids Res.* 8:4057), and the lambda-derived $P_L$ promoter (Shimatake et al., 1981, *Nature* 292:128) and N-gene ribosome binding site ($N_{RBS}$). A portable control system cassette is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six bp 3' of the $N_{RBS}$ sequence. Also useful is the phosphatase A (phoA) system described by Chang et al. in European Patent Publication No. 196,864, published Oct. 8, 1986. However, any available promoter system compatible with procaryotes can be used to construct a modified thermostable DNA polymerase expression vector of the invention.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common (Broach, 1983, *Meth. Enz.* 101:307), other plasmid vectors suitable for yeast expression are known (see, for example, Stinchcomb et al., 1979, *Nature* 282:39; Tschempe et al., 1980, *Gene* 10:157; and Clarke et al., 1983, *Meth. Enz.* 101:300). Control sequences for yeast vectors include promoters for the synthesis of glycolytic enzymes (Hess et al., 1968, *J. Adv. Enzyme Reg.* 7:149; Holland et al., 1978, *Biotechnology* 17:4900; and Holland et al., 1981, *J. Biol. Chem.* 256:1385). Additional promoters known in the art include the promoter for 3-phosphoglycerate kinase (Hitzeman et al., 1980, *J. Biol. Chem.* 255:2073) and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication, and other control sequences is suitable for use in constructing yeast expression vectors for the thermostable DNA polymerases of the present invention.

The nucleotide sequences which code for the thermostable DNA polymerases of the present invention can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273:113), or other viral promoters such as those derived from polyoma, adenovirus 2, bovine papilloma virus (BPV), or avian sarcoma viruses, or immunoglobulin promoters and heat shock promoters. A system for expressing DNA in mammalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences (Depicker et al., 1982, *J. Mol. Appl. Gen.* 1:561) are available. Expression systems employing insect cells utilizing the control systems provided by baculovirus vectors have also been described (Miller et al., 1986, *Genetic Engineering* (Setlow et al., eds., Plenum Publishing) 8:277–297). Insect cell-based expression can be accomplished in *Spodoptera frugipeida*. These systems can also be used to produce recombinant thermostable polymerases of the present invention.

Depending on the host cell used, transformation is done using standard techniques appropriate to such cells. The calcium treatment employing calcium chloride, as described by Cohen, 1972, *Proc. Natl. Acad. Sci. USA* 69:2110 is used for procaryotes or other cells that contain substantial cell wall barriers. Infection with *Agrobacterium tumefaciens* (Shaw et al., 1983, *Gene* 23:315) is used for certain plant cells. For mammalian cells, the calcium phosphate precipitation method of Graham and van der Eb, 1978, *Virology* 52:546 is preferred. Transformations into yeast are carried out according to the method of Van Solingen et al., 1977, *J. Bact.* 130:946 and Hsiao et al., 1979, *Proc. Natl. Acad. Sci. USA* 76:3829.

Once the desired thermostable DNA polymerase with altered 5' to 3' exonuclease activity has been expressed in a recombinant host cell, purification of the protein may be desired. Although a variety of purification procedures can be used to purify the recombinant thermostable polymerases of the invention, fewer steps may be necessary to yield an enzyme preparation of equal purity. Because *E. coli* host proteins are heat-sensitive, the recombinant thermostable DNA polymerases of the invention can be substantially enriched by heat inactivating the crude lysate. This step is done in the presence of a sufficient amount of salt (typically 0.2–0.3M ammonium sulfate) to ensure dissociation of the thermostable DNA polymerase from the host DNA and to reduce ionic interactions of thermostable DNA polymerase with other cell lysate proteins.

In addition, the presence of 0.3M ammonium sulfate promotes hydrophobic interaction with a phenyl sepharose column. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, such as high ionic strength. A descending salt gradient may then be used to elute the sample.

According to the invention, an aqueous mixture (containing the recombinant thermostable DNA polymerase with altered 5' to 3' exonuclease activity) is loaded onto a column containing a relatively strong hydrophobic gel such as phenyl sepharose (manufactured by Pharmacia) or Phenyl TSK (manufactured by Toyo Soda). To promote hydrophobic interaction with a phenyl sepharose column, a solvent is used that contains, for example, greater than or equal to 0.3M ammonium sulfate, with 0.3M being preferred, or greater than or equal to 0.5M NaCl. The column and the sample are adjusted to 0.3M ammonium sulfate in 50 mM Tris (pH 7.5) and 1.0 mM EDTA ("TE") buffer that also contains 0.5 mM DTT, and the sample is applied to the column. The column is washed with the 0.3M ammonium sulfate buffer. The enzyme may then be eluted with solvents that attenuate hydrophobic interactions, such as decreasing salt gradients, ethylene or propylene glycol, or urea.

For long-term stability, the thermostable DNA polymerase enzymes of the present invention can be stored in a buffer that contains one or more non-ionic polymeric detergents. Such detergents are generally those that have a molecular weight in the range of approximately 100 to 250,000 daltons, preferably about 4,000 to 200,000 daltons, and stabilize the enzyme at a pH of from about 3.5 to about 9.5, preferably from about 4 to 8.5. Examples of such detergents include those specified on pages 295–298 of McCutcheon's *Emulsifiers & Detergents*, North American edition (1983), published by the McCutcheon Division of MC Publishing Co., 175 Rock Road, Glen Rock, N.J. (USA) and copending Ser. No. 387,003, filed Jul. 28, 1989, now abandoned in favor of continuation application U.S. Ser. No. 07/873,897, filed Apr. 24, 1992, each of which is incorporated herein by reference.

Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, a polyoxyethylated (20) sorbitan monolaurate from ICI Americas Inc., Wilmington, DE, and Iconol NP-40, an ethoxylated alkyl phenol (nonyl) from BASF Wyandotte Corp., Parsippany, N.J.

The thermostable enzymes of this invention may be used for any purpose in which such enzyme activity is necessary or desired.

DNA sequencing by the Sanger dideoxynucleotide method (Sanger et al., 1977, *Proc. Natl. Acad. Sci. USA* 74:5463–5467) has undergone significant refinement in recent years, including the development of novel vectors (Yanisch-Perron et al., 1985, *Gene* 33:103–119), base analogs (Mills et al., 1979, *Proc. Natl. Acad. Sci. USA* 76:2232–2235, and Barr et al., 1986, *BioTechniques* 4:428–432), enzymes (Tabor et al., 1987, *Proc. Natl. Acad. Sci. USA* 84:4763–4771, and Innis, M. A. et al., 1988, *Proc. Natl. Acad. Sci. USA* 85:9436:9440), and instruments for partial automation of DNA sequence analysis (Smith et al., 1986, *Nature* 321:674–679; Prober et al., 1987, *Science* 238:336–341; and Ansorge et al., 1987, *Nuc. Acids Res.* 15:4593–4602). The basic dideoxy sequencing procedure involves (i) annealing an oligonucleotide primer to a suitable single or denatured double stranded DNA template; (ii) extending the primer with DNA polymerase in four separate reactions, each containing one α-labeled dNTP or ddNTP (alternatively, a labeled primer can be used), a mixture of unlabeled dNTPs, and one chain-terminating dideoxynucleotide-5'-triphosphate (ddNTP); (iii) resolving the four sets of reaction products on a high-resolution polyacrylamide-urea gel; and (iv) producing an autoradiographic image of the gel that can be examined to infer the DNA sequence. Alternatively, fluorescently labeled primers or nucleotides can be used to identify the reaction products. Known dideoxy sequencing methods utilize a DNA polymerase such as the Klenow fragment of *E. coli* DNA polymerase I, reverse transcriptase, *Taq* DNA polymerase, or a modified T7 DNA polymerase.

The introduction of commercial kits has vastly simplified the art, making DNA sequencing a routine technique for any laboratory. However, there is still a need in the art for sequencing protocols that work well with nucleic acids that contain secondary structure such as palindromic hairpin loops and with G+C-rich DNA. Single stranded DNAs can form secondary structure, such as a hairpin loop, that can seriously interfere with a dideoxy sequencing protocol, both through improper termination in the extension reaction, or in the case of an enzyme with 5' to 3' exonuclease activity, cleavage of the template strand at the juncture of the hairpin. Since high temperature destabilizes secondary structure, the ability to conduct the extension reaction at a high temperature, i.e., 70°–75° C., with a thermostable DNA polymerase results in a significant improvement in the sequencing of DNA that contains such secondary structure. However, temperatures compatible with polymerase extension do not eliminate all secondary structure. A 5' to 3' exonuclease-deficient thermostable DNA polymerase would be a further improvement in the art, since the polymerase could synthesize through the hairpin in a strand displacement reaction, rather than cleaving the template, resulting in an improper termination, i.e., an extension run-off fragment.

As an alternative to basic dideoxy sequencing, cycle dideoxy sequencing is a linear, asymmetric amplification of target sequences in the presence of dideoxy chain terminators. A single cycle produces a family of extension products of all possible lengths. Following denaturation of the extension reaction product from the DNA template, multiple cycles of primer annealing and primer extension occur in the presence of dideoxy terminators. The process is distinct from PCR in that only one primer is used, the accumulation of the sequencing reaction products in each cycle is linear, and the amplification products are heterogeneous in length and do not serve as template for the next reaction. Cycle dideoxy sequencing is a technique providing advantages for laboratories using automated DNA sequencing instruments and for other high volume sequencing laboratories. It is possible to directly sequence genomic DNA, without cloning, due to the specificity of the technique and the increased amount of signal generated. Cycle sequencing protocols accommodate single and double stranded templates, including genomic, cloned, and PCR-amplified templates.

Thermostable DNA polymerases have several advantages in cycle sequencing: they tolerate the stringent annealing temperatures which are required for specific hybridization of primer to genomic targets as well as tolerating the multiple cycles of high temperature denaturation which occur in each cycle. Performing the extension reaction at high temperatures, i.e., 70°–75° C., results in a significant improvement in sequencing results with DNA that contains secondary structure, due to the destabilization of secondary structure. However, such temperatures will not eliminate all secondary structure. A 5' to 3' exonuclease-deficient thermostable DNA polymerase would be a further improvement in the art, since the polymerase could synthesize through the hairpin in a strand displacement reaction, rather than cleaving the template and creating an improper termination. Additionally, like PCR, cycle sequencing suffers from the phenomenon of product strand renaturation. In the case of a thermostable DNA polymerase possessing 5' to 3' exonuclease activity, extension of a primer into a double stranded region created by product strand renaturation will result in cleavage of the renatured complementary product strand. The cleaved strand will be shorter and thus appear as an improper termination. In addition, the correct, previously synthesized termination signal will be attenuated. A thermostable DNA polymerase deficient in 5' to 3' exonuclease activity will improve the art, in that such extension product fragments will not be formed. A variation of cycle sequencing, involves the simultaneous generation of sequencing ladders for each strand of a double stranded template while sustaining some degree of amplification (Ruano and Kidd, *Proc. Natl. Acad. Sci. USA,* 1991 88:2815–2819). This method of coupled amplification and sequencing would benefit in a similar fashion as standard cycle sequencing from the use of a thermostable DNA polymerase deficient in 5' to 3' exonuclease activity.

In a particularly preferred embodiment, the enzymes in which the 5' to 3' exonuclease activity has been reduced or eliminated catalyze the nucleic acid amplification reaction known as PCR, and as stated above, with the resultant effect of producing a better yield of desired product than is achieved with the respective native enzymes which have greater amounts of the 5' to 3' exonuclease activity. Improved yields are the result of the inability to degrade previously synthesized product caused by 5' to 3' exonuclease activity. This process for amplifying nucleic acid sequences is disclosed and claimed in U.S. Pat. Nos. 4,683,202 and 4,865,188, each of which is incorporated herein by reference. The PCR nucleic acid amplification method involves amplifying at least one specific nucleic acid sequence contained in a nucleic acid or a mixture of nucleic acids and in the most common embodiment, produces double-stranded DNA. Aside from improved yields, thermostable DNA polymerases with attenuated 5' to 3' exonuclease activity exhibit an improved ability to generate longer PCR products, an improved ability to produce products from G+C-rich templates and an improved ability to generate PCR products and DNA sequencing ladders from templates with a high degree of secondary structure.

For ease of discussion, the protocol set forth below assumes that the specific sequence to be amplified is contained in a double-stranded nucleic acid. However, the process is equally useful in amplifying single-stranded nucleic acid, such as mRNA, although in the preferred embodiment the ultimate product is still double-stranded DNA. In the amplification of a single-stranded nucleic acid, the first step involves the synthesis of a complementary strand (one of the two amplification primers can be used for this purpose), and the succeeding steps proceed as in the double-stranded amplification process described below.

This amplification process comprises the steps of:

(a) contacting each nucleic acid strand with four different nucleoside triphosphates and two oligonucleotide primers for each specific sequence being amplified, wherein each primer is selected to be substantially complementary to the different strands of the specific sequence, such that the extension product synthesized from one primer, when separated from its complement, can serve as a template for synthesis of the extension product of the other primer, said contacting being at a temperature that allows hybridization of each primer to a complementary nucleic acid strand;

(b) contacting each nucleic acid strand, at the same time as or after step (a), with a thermostable DNA polymerase of the present invention that enables combination of the nucleoside triphosphates to form primer extension products complementary to each strand of the specific nucleic acid sequence;

(c) maintaining the mixture from step (b) at an effective temperature for an effective time to promote the activity of the enzyme and to synthesize, for each different sequence being amplified, an extension product of each primer that is complementary to each nucleic acid strand template, but not so high as to separate each extension product from the complementary strand template;

(d) heating the mixture from step (c) for an effective time and at an effective temperature to separate the primer extension products from the templates on which they were synthesized to produce single-stranded molecules but not so high as to denature irreversibly the enzyme;

(e) cooling the mixture from step (d) for an effective time and to an effective temperature to promote hybridization of a primer to each of the single-stranded molecules produced in step (d); and (f) maintaining the mixture from step (e) at an effective temperature for an effective time to promote the activity of the enzyme and to synthesize, for each different sequence being amplified, an extension product of each primer that is complementary to each nucleic acid template produced in step (d) but not so high as to separate each extension product from the complementary strand template. The effective times and temperatures in steps (e) and (f) may coincide, so that steps (e) and (f) can be carried out simultaneously. Steps (d)–(f) are repeated until the desired level of amplification is obtained.

The amplification method is useful not only for producing large amounts of a specific nucleic acid sequence of known sequence but also for producing nucleic acid sequences that are known to exist but are not completely specified. One need know only a sufficient number of bases at both ends of the sequence in sufficient detail so that two oligonucleotide primers can be prepared that will hybridize to different strands of the desired sequence at relative positions along the sequence such that an extension product synthesized from one primer, when separated from the template (complement), can serve as a template for extension of the other primer into a nucleic acid sequence of defined length. The greater the knowledge about the bases at both ends of the sequence, the greater can be the specificity of the primers for the target nucleic acid sequence and the efficiency of the process and specificity of the reaction.

In any case, an initial copy of the sequence to be amplified must be available, although the sequence need not be pure or a discrete molecule. In general, the amplification process involves a chain reaction for producing, in exponential quantities relative to the number of reaction steps involved, at least one specific nucleic acid sequence given that (a) the ends of the required sequence are known in sufficient detail that oligonucleotides can be synthesized that will hybridize to them and (b) that a small amount of the sequence is available to initiate the chain reaction. The product of the chain reaction will be a discrete nucleic acid duplex with termini corresponding to the 5' ends of the specific primers employed.

Any nucleic acid sequence, in purified or nonpurified form, can be utilized as the starting nucleic acid(s), provided it contains or is suspected to contain the specific nucleic acid sequence one desires to amplify. The nucleic acid to be amplified can be obtained from any source, for example, from plasmids such as pBR322, from cloned DNA or RNA, or from natural DNA or RNA from any source, including bacteria, yeast, viruses, organelles, and higher organisms such as plants and animals. DNA or RNA may be extracted from blood, tissue material such as chorionic villi, or amniotic cells by a variety of techniques. See, e.g., Maniatis et al., 1982, *Molecular Cloning: A Laboratory Manual* (Cold Spring Harbor Laboratory, Cold Spring Harbor, N.Y.) pp. 280–281. Thus, the process may employ, for example, DNA or RNA, including messenger RNA, which DNA or RNA may be single-stranded or double-stranded. In addition, a DNA-RNA hybrid that contains one strand of each may be utilized. A mixture of any of these nucleic acids can also be employed as can nucleic acids produced from a previous amplification reaction (using the same or different primers). The specific nucleic acid sequence to be amplified can be only a fraction of a large molecule or can be present initially as a discrete molecule, so that the specific sequence constitutes the entire nucleic acid.

The sequence to be amplified need not be present initially in a pure form; the sequence can be a minor fraction of a complex mixture, such as a portion of the β-globin gene contained in whole human DNA (as exemplified in Saiki et al., 1985, *Science* 230:1530–1534) or a portion of a nucleic acid sequence due to a particular microorganism, which organism might constitute only a very minor fraction of a particular biological sample. The cells can be directly used in the amplification process after suspension in hypotonic buffer and heat treatment at about 90° C.-100° C. until cell lysis and dispersion of intracellular components occur (generally 1 to 15 minutes). After the heating step, the amplification reagents may be added directly to the lysed cells. The starting nucleic acid sequence can contain more than one desired specific nucleic acid sequence. The amplification process is useful not only for producing large amounts of one specific nucleic acid sequence but also for amplifying simultaneously more than one different specific nucleic acid sequence located on the same or different nucleic acid molecules.

Primers play a key role in the PCR process. The word "primer" as used in describing the amplification process can refer to more than one primer, particularly in the case where there is some ambiguity in the information regarding the terminal sequence(s) of the fragment to be amplified or where one employs the degenerate primer process described in PCT Application No. 91/05753, filed Aug. 13, 1991, which published on Mar. 5, 1992. For instance, in the case where a nucleic acid sequence is inferred from protein sequence information, a collection of primers containing sequences representing all possible codon variations based on degeneracy of the genetic code can be used for each strand. One primer from this collection will be sufficiently homologous with a portion of the desired sequence to be amplified so as to be useful for amplification.

In addition, more than one specific nucleic acid sequence can be amplified from the first nucleic acid or mixture of nucleic acids, so long as the appropriate number of different oligonucleotide primers are utilized. For example, if two different specific nucleic acid sequences are to be produced, four primers are utilized. Two of the primers are specific for one of the specific nucleic acid sequences, and the other two primers are specific for the second specific nucleic acid sequence. In this manner, each of the two different specific sequences can be produced exponentially by the present process.

A sequence within a given sequence can be amplified after a given number of amplification cycles to obtain greater specificity in the reaction by adding, after at least one cycle of amplification, a set of primers that are complementary to internal sequences (i.e., sequences that are not on the ends) of the sequence to be amplified. Such primers can be added at any stage and will provide a shorter amplified fragment. Alternatively, a longer fragment can be prepared by using primers with non-complementary ends but having some overlap with the primers previously utilized in the amplification.

Primers also play a key role when the amplification process is used for in vitro mutagenesis. The product of an amplification reaction where the primers employed are not exactly complementary to the original template will contain the sequence of the primer rather than the template, so introducing an in vitro mutation. In further cycles, this mutation will be amplified with an undiminished efficiency because no further mispaired priming is required. The process of making an altered DNA sequence as described above could be repeated on the altered DNA using different primers to induce further sequence changes. In this way, a series of mutated sequences can gradually be produced wherein each new addition to the series differs from the last in a minor way, but from the original DNA source sequence in an increasingly major way.

Because the primer can contain as part of its sequence a non-complementary sequence, provided that a sufficient amount of the primer contains a sequence that is complementary to the strand to be amplified, many other advantages can be realized. For example, a nucleotide sequence that is not complementary to the template sequence (such as, e.g., a promoter, linker, coding sequence, etc.) may be attached at the 5' end of one or both of the primers and so appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

Oligonucleotide primers can be prepared using any suitable method, such as, for example, the phosphotriester and phosphodiester methods described above, or automated embodiments thereof. In one such automated embodiment, diethylphosphoramidites are used as starting materials and can be synthesized as described by Beaucage et al., 1981, *Tetrahedron Letters* 22:1859–1862. One method for synthesizing oligonucleotides on a modified solid support is described in U.S. Pat. No. 4,458,066. One can also use a primer that has been isolated from a biological source (such as a restriction endonuclease digest).

No matter what primers are used, however, the reaction mixture must contain a template for PCR to occur, because the specific nucleic acid sequence is produced by using a nucleic acid containing that sequence as a template. The first step involves contacting each nucleic acid strand with four different nucleoside triphosphates and two oligonucleotide primers for each specific nucleic acid sequence being amplified or detected. If the nucleic acids to be amplified or detected are DNA, then the nucleoside triphosphates are usually dATP, dCTP, dGTP, and dTTP, although various nucleotide derivatives can also be used in the process. For example, when using PCR for the detection of a known sequence in a sample of unknown sequences, dTTP is often replaced by dUTP in order to reduce contamination between samples as taught in PCT Application No. 91/05210 filed Jul. 23, 1991, which published on Feb. 6, 1992, incorporated herein by reference.

The concentration of nucleoside triphosphates can vary widely. Typically, the concentration is 50 to 200 μM in each dNTP in the buffer for amplification, and $MgCl_2$ is present in the buffer in an amount of 1 to 3 mM to activate the polymerase and increase the specificity of the reaction. However, dNTP concentrations of 1 to 20 μM may be preferred for some applications, such as DNA sequencing or generating radiolabeled probes at high specific activity.

The nucleic acid strands of the target nucleic acid serve as templates for the synthesis of additional nucleic acid strands, which are extension products of the primers. This synthesis can be performed using any suitable method, but generally occurs in a buffered aqueous solution, preferably at a pH of 7 to 9, most preferably about 8. To facilitate synthesis, a molar excess of the two oligonucleotide primers is added to the buffer containing the template strands. As a practical matter, the amount of primer added will generally be in molar excess over the amount of complementary strand (template) when the sequence to be amplified is contained in a mixture of complicated long-chain nucleic acid strands. A large molar excess is preferred to improve the efficiency of the process. Accordingly, primer:template ratios of at least 1000:1 or higher are generally employed for cloned DNA templates, and primer: template ratios of about $10^8$:1 or higher are generally employed for amplification from complex genomic samples.

The mixture of template, primers, and nucleoside triphosphates is then treated according to whether the nucleic acids being amplified or detected are double- or single-stranded. If the nucleic acids are single-stranded, then no denaturation step need be employed prior to the first extension cycle, and the reaction mixture is held at a temperature that promotes hybridization of the primer to its complementary target (template) sequence. Such temperature is generally from about 35° C. to 65° C. or more, preferably about 37° C. to 60° C. for an effective time, generally from a few seconds to five minutes, preferably from 30 seconds to one minute. A hybridization temperature of 35° C. to 70° C. may be used for 5' to 3' exonuclease mutant thermostable DNA polymerases. Primers that are 15 nucleotides or longer in length are used to increase the specificity of primer hybridization. Shorter primers require lower hybridization temperatures.

The complement to the original single-stranded nucleic acids can be synthesized by adding the thermostable DNA polymerase of the present invention in the presence of the appropriate buffer, dNTPs, and one or more oligonucleotide primers. If an appropriate single primer is added, the primer extension product will be complementary to the single-stranded nucleic acid and will be hybridized with the nucleic acid strand in a duplex of strands of equal or unequal length (depending on where the primer hybridizes to the template), which may then be separated into single strands as described above to produce two single, separated, complementary strands. A second primer would then be added so that subsequent cycles of primer extension would occur using both the original single-stranded nucleic acid and the extension product of the first primer as templates. Alternatively, two or more appropriate primers (one of which will prime synthesis using the extension product of the other primer as a template) can be added to the single-stranded nucleic acid and the reaction carried out.

If the nucleic acid contains two strands, as in the case of amplification of a double-stranded target or second-cycle amplification of a single-stranded target, the strands of nucleic acid must be separated before the primers are hybridized. This strand separation can be accomplished by any suitable denaturing method, including physical, chemical or enzymatic means. One preferred physical method of separating the strands of the nucleic acid involves heating the nucleic acid until complete (>99%) denaturation occurs. Typical heat denaturation involves temperatures ranging from about 80° C. to 105° C. for times generally ranging from about a few seconds to minutes, depending on the composition and size of the nucleic acid. Preferably, the effective denaturing temperature is 90° C.-100° C. for a few seconds to 1 minute. Strand separation may also be induced by an enzyme from the class of enzymes known as helicases or the enzyme RecA, which has helicase activity and in the presence of ATP is known to denature DNA. The reaction conditions suitable for separating the strands of nucleic acids with helicases are described by Kuhn Hoffmann-Berling, 1978, *CSH-Quantitative Biology* 43:63, and techniques for using RecA are reviewed in Radding, 1982, *Ann. Rev. Genetics* 16:405–437. The denaturation produces two separated complementary strands of equal or unequal length.

If the double-stranded nucleic acid is denatured by heat, the reaction mixture is allowed to cool to a temperature that promotes hybridization of each primer to the complementary target (template) sequence. This temperature is usually from about 35° C. to 65° C. or more, depending on reagents, preferably 37° C. to 60° C. The hybridization temperature is maintained for an effective time, generally a few seconds to minutes, and preferably 10 seconds to 1 minute. In practical terms, the temperature is simply lowered from about 95° C. to as low as 37° C., and hybridization occurs at a temperature within this range.

Whether the nucleic acid is single- or double-stranded, the thermostable DNA polymerase of the present invention can be added prior to or during the denaturation step or when the temperature is being reduced to or is in the range for promoting hybridization. Although the thermostability of the polymerases of the invention allows one to add such polymerases to the reaction mixture at any time, one can substantially inhibit non-specific amplification by adding the polymerase to the reaction mixture at a point in time when the mixture will not be cooled below the stringent hybridization temperature. After hybridization, the reaction mixture is then heated to or maintained at a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer that is complementary to each nucleic acid template, but must not be so high as to denature each extension product from its complementary template (i.e., the temperature is generally less than about 80° C. to 90° C.).

Depending on the nucleic acid(s) employed, the typical temperature effective for this synthesis reaction generally ranges from about 40° C. to 80° C., preferably 50° C. to 75° C. The temperature more preferably ranges from about 65° C. to 75° C. for the thermostable DNA polymerases of the present invention. The period of time required for this synthesis may range from about 10 seconds to several minutes or more, depending mainly on the temperature, the length of the nucleic acid, the enzyme, and the complexity of the nucleic acid mixture. The extension time is usually about 30 seconds to a few minutes. If the nucleic acid is longer, a longer time period is generally required for complementary strand synthesis.

The newly synthesized strand and the complement nucleic acid strand form a double-stranded molecule that is used in the succeeding steps of the amplification process. In the next step, the strands of the double-stranded molecule are separated by heat denaturation at a temperature and for a time effective to denature the molecule, but not at a temperature and for a period so long that the thermostable enzyme is completely and irreversibly denatured or inactivated. After this denaturation of template, the temperature is decreased to a level that promotes hybridization of the primer to the complementary single-stranded molecule (template) produced from the previous step, as described above.

After this hybridization step, or concurrently with the hybridization step, the temperature is adjusted to a temperature that is effective to promote the activity of the thermostable enzyme to enable synthesis of a primer extension product using as a template both the newly synthesized and the original strands. The temperature again must not be so high as to separate (denature) the extension product from its template, as described above. Hybridization may occur during this step, so that the previous step of cooling after denaturation is not required. In such a case, using simultaneous steps, the preferred temperature range is 50° C. to 70° C.

The heating and cooling steps involved in one cycle of strand separation, hybridization, and extension product synthesis can be repeated as many times as needed to produce the desired quantity of the specific nucleic acid sequence. The only limitation is the amount of the primers, thermostable enzyme, and nucleoside triphosphates present. Usually, from 15 to 30 cycles are completed. For diagnostic detection of amplified DNA, the number of cycles will depend on the nature of the sample, the initial target concentration in the sample and the sensitivity of the detection process used after amplification. For a given sensitivity of detection, fewer cycles will be required if the sample being amplified is pure and the initial target concentration is high. If the sample is a complex mixture of nucleic acids and the initial target concentration is low, more cycles will be required to amplify the signal sufficiently for detection. For general amplification and detection, the process is repeated about 15 times. When amplification is used to generate sequences to be detected with labeled sequence-specific probes and when human genomic DNA is the target of amplification, the process is repeated 15 to 30 times to amplify the sequence sufficiently so that a clearly detectable signal is produced, i.e., so that background noise does not interfere with detection.

No additional nucleotides, primers, or thermostable enzyme need be added after the initial addition, provided that no key reagent has been exhausted and that the enzyme has not become denatured or irreversibly inactivated, in which case additional polymerase or other reagent would have to be added for the reaction to continue. After the appropriate number of cycles has been completed to produce the desired amount of the specific nucleic acid sequence, the reaction can be halted in the usual manner, e.g., by inactivating the enzyme by adding EDTA, phenol, SDS, or $CHCl_3$ or by separating the components of the reaction.

The amplification process can be conducted continuously. In one embodiment of an automated process, the reaction mixture can be temperature cycled such that the temperature is programmed to be controlled at a certain level for a certain time. One such instrument for this purpose is the automated machine for handling the amplification reaction developed and marketed by Perkin-Elmer Cetus Instruments. Detailed instructions for carrying out PCR with the instrument are available upon purchase of the instrument.

The thermostable DNA polymerases of the present invention with altered 5' to 3' exonuclease activity are very useful in the diverse processes in which amplification of a nucleic acid sequence by PCR is useful. The amplification method may be utilized to clone a particular nucleic acid sequence for insertion into a suitable expression vector, as described in U.S. Pat. No. 4,800,159. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers. Other processes suitable for the thermostable DNA polymerases of the present invention include those described in U.S. Pat. Nos. 4,683,195 and 4,683,202 and European Patent Publication Nos. 229,701; 237,362; and 258,017; these patents and publications are incorporated herein by reference. In addition, the present enzyme is useful in asymmetric PCR (see Gyllensten and Erlich, 1988, *Proc. Natl. Acad. Sci. USA* 85:7652–7656, incorporated herein by; inverse PCR (Ochman et al., 1988, *Genetics* 120:621, incorporated herein by reference); and for DNA sequencing (see Innis et al., 1988, *Proc. Natl. Acad. Sci. USA* 85:9436–9440, and McConlogue et al., 1988, *Nuc. Acids Res.* 16(20):9869), random amplification of cDNA ends (RACE), random priming PCR which is used to amplify a series of DNA fragments, and PCR processes with single sided specificity such as anchor PCR and ligation-mediated anchor PCR as described by Loh, E. in *METHODS: A Companion to Methods in Enzymology* (1991) 2: pp. 11–19.

An additional process in which a 5' to 3' exonuclease deficient thermostable DNA polymerase would be useful is a process referred to as polymerase ligase chain reaction (PLCR). As its name suggests, this process combines features of PCR with features of ligase chain reaction (LCR).

PLCR was developed in part as a technique to increase the specificity of allele-specific PCR in which the low concentrations of dNTPs utilized (~1 μM) limited the extent of amplification. In PLCR, DNA is denatured and four complementary, but not adjacent, oligonucleotide primers are added with dNTPs, a thermostable DNA polymerase and a thermostable ligase.

The primers anneal to target DNA in a non-adjacent fashion and the thermostable DNA polymerase causes the addition of appropriate dNTPs to the 3' end of the downstream primer to fill the gap between the non-adjacent primers and thus render the primers adjacent. The thermostable ligase will then ligate the two adjacent oligonucleotide primers.

However, the presence of 5' to 3' exonuclease activity in the thermostable DNA polymerase significantly decreases the probability of closing the gap between the two primers because such activity causes the excision of nucleotides or small oligonucleotides from the 5' end of the downstream primer thus preventing ligation of the primers. Therefore, a thermostable DNA polymerase with attenuated or eliminated 5' to 3' exonuclease activity would be particularly useful in PLCR.

Briefly, the thermostable DNA polymerases of the present invention which have been mutated to have reduced, attenuated or eliminated 5' to 3' exonuclease activity are useful for the same procedures and techniques as their respective non-mutated polymerases except for procedures and techniques which require 5' to 3' exonuclease activity such as the homogeneous assay technique discussed below. Moreover, the mutated DNA polymerases of the present invention will oftentimes result in more efficient performance of the procedures and techniques due to the reduction or elimination of the inherent 5' to 3' exonuclease activity.

Specific thermostable DNA polymerases with attenuated 5' to 3' exonuclease activity include the following mutated forms of *Taq*, *Tma*, *Tsps*17, TZ05, *Tth* and *Taf* DNA polymerases. In the table below, and throughout the specification, deletion mutations are inclusive of the numbered nucleotides or amino acids which define the deletion.

| DNA Polymerase | Mutation | Mutant Designation |
|---|---|---|
| Taq | G(137) to A in nucleotide SED ID NO: 1 | pRDA3-2 |
| | Gly (46) to Asp in amino acid SEQ ID NO: 2 | ASP46 Taq |
| | Deletion of nucleotides 4–228 of nucleotide SEQ ID NO: 1 | pTAQd2-76 |
| | Deletion of amino acids 2–76 of amino acid SEQ ID NO: 2 | MET—ALA 77 Taq |
| | Delection of nucleotides 4–138 of nucleotide SEQ ID NO: 1 | pTAQd2-46 |
| | Deletion of amino acids 2–46 of amino acid SEQ ID NO: 2 | MET—PHE 47 Taq |
| | Deletion of nucleotides 4–462 of nucleotide SEQ ID NO: 1 | pTAQd2-155 |
| | Deletion of amino acids 2–154 of amino acid SEQ ID NO: 2 | MET—VAL 155 Taq |
| | Deletion of nucleotides 4–606 of nucleotide; SEQ ID NO: 1 | pTAQd2-202 |
| | Deletion of amino acids 2–202 of amino acid SEQ ID NO: 2 | MET—THR 203 Taq |
| | Deletion of nucleotides 4–867 of nucleotide SEQ ID NO: 1 | pLSG8 |
| | Deletion of amino acids 2–289 of amino acid SEQ ID NO: 2 | MET—SER 290 Taq (Stoffel fragment) |
| Tma | G(110) to A in nucleotide SEQ ID NO: 3 | |
| | Gly (37) to Asp in amino acid SEQ ID NO: 4 | ASP37 Tma |
| | Deletion of nucleotides 4–131 of nucleotide SEQ ID NO: 3 | pTMAd2-37 |
| | Deletion of amino acids 2–37 of amino acid SEQ ID NO: 4 | MET—VAL 38 Tma |
| | Deletion of nucleotides 4–60 of nucleotide SEQ ID NO: 3 | pTMAd2-20 |
| | Deletion of amino acids 2–20 of amino acid SEQ ID NO: 4 | MET—ASP 21 Tma |
| | Deletion of nucleotides 4–219 of nucleotide SEQ ID NO: 3 | pTMAd2-73 |
| | Deletion of amino acids 2–73 amino acid SEQ ID NO: 4 | MET—GLU 74 Tma |
| | Deletion of nucleotides 1–417 of nucleotide SEQ ID NO: 3 | pTMA16 |
| | Deletion of amino acids 1–139 of amino acid SEQ ID NO: 4 | MET 140 Tma |
| | Deletion of nucleotides 1–849 of nucleotide SEQ ID NO: 3 | pTMA15 |
| | Deletion of amino acids 1–283 of amino acid SEQ ID NO: 4 | MET 284 Tma |
| Tsps17 | G(128) to A in nucleotide SEQ ID NO: 5 | |
| | Gly (43) to Asp in amino acid SEQ ID NO: 6 | ASP43 Tsps17 |
| | Deletion of nucleotides 4–129 of nucleotide SEQ ID NO: 5 | pSPSd2-43 |
| | Deletion of amino acids 2–43 of amino acid SEQ ID NO: 6 | MET—PHE 44 Tsps17 |
| | Deletion of nucleotides 4–219 of nucleotide SEQ ID NO: 5 | pSPSd2-73 |
| | Deletion of amino acids 2–73 of amino acid SEQ ID NO: 6 | MET—ALA 74 Tsps17 |
| | Deletion of nucleotides 4–453 of nucleotide SEQ ID NO: 5 | pSPSd2-151 |
| | Deletion of amino acids 2–151 of amino acid SEQ ID NO: 6 | MET—LEU 152 Tsps17 |
| | Deletion of nucleotides 4–597 of nucleotide SEQ ID NO: 5 | pSPSd2-199 |
| | Deletion of amino acids 2–199 of amino acid SEQ ID NO: 6 | MET—THR 200 Tsps17 |
| | Deletion of nucleotides 4–861 of nucleotide SEQ ID NO: 5 | pSPSA288 |
| | Deletion of amino acids 2–287 of amino acid SEQ ID NO: 6 | MET—ALA 288 Tsps 17 |

-continued

| DNA Polymerase | Mutation | Mutant Designation |
|---|---|---|
| TZ05 | G(137) to A in nucleotide SEQ ID NO: 7 | |
| | Gly (46) to Asp in amino acid SEQ ID NO: 8 | ASP46 TZ05 |
| | Deletion of nucleotides 4–138 of nucleotide SEQ ID NO: 7 | pZ05d2-46 |
| | Deletion of amino acids 2–46 of amino acid SEQ ID NO: 8 | MET—PHE 47 TZ05 |
| | Deletion of nucleotides 4–231 of nucleotide SEQ ID NO: 7 | pZ05d2-77 |
| | Deletion of amino acids 2–77 of amino acid SEQ ID NO: 8 | MET—ALA 78 TZ05 |
| | Deletion of nucleotides 4–475 of nucleotide SEQ ID NO: 7 | pZ05d2-155 |
| | Deletion of amino acids 2–155 of amino acid SEQ ID NO: 8 | MET—VAL 156 TZ05 |
| | Deletion of nucleotides 4–609 of nucleotide SEQ ID NO: 7 | pZ05d2-203 |
| | Deletion of amino acids 2–203 of amino acid SEQ ID NO: 8 | MET—THR 204 TZ05 |
| | Deletion of nucleotides 4–873 of nucleotide SEQ ID NO: 7 | pZ05A292 |
| | Deletion of amino acids 2–291 of amino acid SEQ ID NO: 8 | MET—ALA 292 TZ05 |
| Tth | G(137) to A in nucleotide SEQ ID NO: 9 | |
| | Gly (46) to Asp in amino acid SEQ ID NO: 10 | ASP46 Tth |
| | Deletion of nucleotides 4–138 of nucleotide SEQ ID NO: 9 | pTTHd2-46 |
| | Deletion of amino acids 2–46 of amino acid SEQ ID NO: 10 | MET—PHE 47 Tth |
| | Deletion of nucleotides 4–231 of nucleotide SEQ ID NO: 9 | pTTHd2-77 |
| | Deletion of amino acids 2–77 of amino acid SEQ ID NO: 10 | MET—ALA 78 Tth |
| | Deletion of nucleotides 4–465 of nucleotide SEQ ID NO: 9 | pTTHd2-155 |
| | Deletion of amino acids 2–155 of amino acid SEQ ID NO: 10 | MET—VAL 156 Tth |
| | Deletion of nucleotides 4–609 of nucleotide SEQ ID NO: 9 | pTTHd2-203 |
| | Deletion of amino acids 2–203 of amino acid SEQ ID NO: 10 | MET—THR 204 Tth |
| | Deletion of nucleotides 4–873 of nucleotide SEQ ID NO: 9 | pTTHA292 |
| | Deletion of amino acids 2–291 of amino acid SEQ ID NO: 10 | MET—ALA 292 Tth |
| Taf | G(110) to A and A(111) to T in nucleotide SEQ ID NO: 11 | |
| | Gly (37) to Asp in amino acid SEQ ID NO: 12 | ASP37 Taf |
| | Deletion of nucleotides 4–111 of nucleotide SEQ ID NO: 11 | pTAFd2-37 |
| | Deletion of amino acids 2–37 of amino acid SEQ ID NO: 12 | MET—LEU 38 Taf |
| | Deletion of nucleotides 4–279 of nucleotide SEQ ID NO: 11 | pTAF09 |
| | Deletion of amino acids 2–93 amino acid SEQ ID NO: 12 | MET—TYR 94 Taf |
| | Deletion of nucleotides 4–417 of nucleotide SEQ ID NO: 11 | pTAF11 |
| | Deletion of amino acids 2–139 of amino acid SEQ ID NO: 12 | MET—GLU 140 Taf |
| | Deletion of nucleotides 4–609 of nucleotide SEQ ID NO: 11 | pTAFd2-203 |
| | Deletion of amino acids 2–203 of amino acid SEQ ID NO: 12 | MET—THR 204 Taf |
| | Deletion of nucleotides 4–852 of nucleotide SEQ ID NO: 11 | pTAFI285 |
| | Deletion of amino acids 2–284 of amino acid SEQ ID NO: 12 | MET—ILE 285 Taf |

Thermostable DNA Polymerases With Enhanced 5' to 3' Exonuclease Activity

Another aspect of the present invention involves the generation of thermostable DNA polymerases which exhibit enhanced or increased 5' to 3' exonuclease activity over that of their respective native polymerases. The thermostable DNA polymerases of the present invention which have increased or enhanced 5' to 3' exonuclease activity are particularly useful in the homogeneous assay system described in PCT application No. 91/05571 filed Aug. 6, 1991, which published on Feb. 10, 1992, which is incorporated herein by reference. Briefly, this system is a process for the detection of a target nucleic acid sequence in a sample comprising:

(a) contacting a sample comprising single-stranded nucleic acids with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3' end of the -first oligonucleotide is adjacent to the 5' end of the labeled oligonucleotide;

(b) maintaining the mixture of step (a) with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments; and (c) detecting and/or measuring the release of labeled fragments.

This homogeneous assay system is one which generates signal while the target sequence is amplified, thus, minimizing the post-amplification handling of the amplified product which is common to other assay systems. Furthermore, a particularly preferred use of the thermostable DNA polymerases with increased 5' to 3' exonuclease activity is in a homogeneous assay system which utilizes PCR technology. This particular assay system involves:

(a) providing to a PCR assay containing said sample, at least one labeled oligonucleotide containing a sequence complementary to a region of the target nucleic acid, wherein said labeled oligonucleotide anneals within the target nucleic acid sequence bounded by the oligonucleotide primers of step (b);

(b) providing a set of oligonucleotide primers, wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand; and wherein each oligonucleotide primer is selected to anneal to its complementary template upstream of any labeled oligonucleotide annealed to the same nucleic acid strand;

(c) amplifying the target nucleic acid sequence employing a nucleic acid polymerase having 5' to 3' nuclease activity as a template-dependent polymerizing agent under conditions which are permissive for PCR cycling steps of (i) annealing of primers and labeled oligonucleotide to a template nucleic acid sequence contained within the target region, and (ii) extending the primer, wherein said nucleic acid polymerase synthesizes a primer extension product while the 5' to 3' nuclease activity of the nucleic acid polymerase simultaneously releases labeled fragments from the annealed duplexes comprising labeled oligonucleotide and its complementary template nucleic acid sequences, thereby creating detectable labeled fragments; and (d) detecting and/or measuring the release of labeled fragments to determine the presence or absence of target sequence in the sample.

The increased 5' to 3' exonuclease activity of the thermostable DNA polymerases of the present invention when used in the homogeneous assay systems causes the cleavage of mononucleotides or small oligonucleotides from an oligonucleotide annealed to its larger, complementary polynucleotide. In order for cleavage to occur efficiently, an upstream oligonucleotide must also be annealed to the same larger polynucleotide.

The 3' end of this upstream oligonucleotide provides the initial binding site for the nucleic acid polymerase. As soon as the bound polymerase encounters the 5' end of the downstream oligonucleotide, the polymerase can cleave mononucleotides or small oligonucleotides therefrom.

The two oligonucleotides can be designed such that they anneal in close proximity on the complementary target nucleic acid such that binding of the nucleic acid polymerase to the 3' end of the upstream oligonucleotide automatically puts it in contact with the 5' end of the downstream oligonucleotide. This process, because polymerization is not required to bring the nucleic acid polymerase into position to accomplish the cleavage, is called "polymerization-independent cleavage".

Alternatively, if the two oligonucleotides anneal to more distantly spaced regions of the template nucleic acid target, polymerization must occur before the nucleic acid polymerase encounters the 5' end of the downstream oligonucleotide. As the polymerization continues, the polymerase progressively cleaves mononucleotides or small oligonucleotides from the 5' end of the downstream oligonucleotide. This cleaving continues until the remainder of the downstream oligonucleotide has been destabilized to the extent that it dissociates from the template molecule. This process is called "polymerization-dependent cleavage".

The attachment of label to the downstream oligonucleotide permits the detection of the cleaved mononucleotides and small oligonucleotides. Subsequently, any of several strategies may be employed to distinguish the uncleaved labelled oligonucleotide from the cleaved fragments thereof. In this manner, nucleic acid samples which contain sequences complementary to the upstream and downstream oligonucleotides can be identified. Stated differently, a labelled oligonucleotide is added concomittantly with the primer at the start of PCR, and the signal generated from hydrolysis of the labelled nucleotide(s) of the probe provides a means for detection of the target sequence during its amplification.

In the homogeneous assay system process, a sample is provided which is suspected of containing the particular oligonucleotide sequence of interest, the "target nucleic acid". The target nucleic acid contained in the sample may be first reverse transcribed into cDNA, if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid may exist in a single-stranded form in the sample, such as, for example, single-stranded RNA or DNA viruses.

The denatured nucleic acid strands are then incubated with preselected oligonucleotide primers and labeled oligonucleotide (also referred to herein as "probe") under hybridization conditions, conditions which enable the binding of the primers and probes to the single nucleic acid strands. As known in the art, the primers are selected so that their relative positions along a duplex sequence are such that an extension product synthesized from one primer, when the extension product is separated from its template (complement), serves as a template for the extension of the other primer to yield a replicate chain of defined length.

Because the complementary strands are longer than either the probe or primer, the strands have more points of contact and thus a greater chance of finding each other over any given period of time. A high molar excess of probe, plus the primer, helps tip the balance toward primer and probe annealing rather than template reannealing.

The primer must be sufficiently long to prime the synthesis of extension products in the presence of the agent for polymerization. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the oligonucleotide primer typically contains about 15–30 nucleotides, although a primer may contain more or fewer nucleotides. The primers must be sufficiently complementary to anneal to their respective strands selectively and form stable duplexes.

The primers used herein are selected to be "substantially" complementary to the different strands of each specific sequence to be amplified. The primers need not reflect the exact sequence of the template, but must be sufficiently complementary to hybridize selectively to their respective strands. Non-complementary bases or longer sequences can be interspersed into the primer or located at the ends of the primer, provided the primer retains sufficient complementarity with a template strand to form a stable duplex therewith. The non-complementary nucleotide sequences of the primers may include restriction enzyme sites.

In the practice of the homogeneous assay system, the labeled oligonucleotide probe must be first annealed to a complementary nucleic acid before the nucleic acid polymerase encounters this duplex region, thereby permitting the 5' to 3' exonuclease activity to cleave and release labeled oligonucleotide fragments.

To enhance the likelihood that the labeled oligonucleotide will have annealed to a complementary nucleic acid before primer extension polymerization reaches this duplex region, or before the polymerase attaches to the upstream oligonucleotide in the polymerization-independent process, a variety of techniques may be employed. For the polymerization-dependent process, one can position the probe so that the 5'-end of the probe is relatively far from the 3'-end of the primer, thereby giving the probe more time to anneal before primer extension blocks the probe binding site. Short primer molecules generally require lower temperatures to form sufficiently stable hybrid complexes with the target nucleic acid. Therefore, the labeled oligonucleotide can be designed to be longer than the primer so that the labeled oligonucleotide anneals preferentially to the target at higher temperatures relative to primer annealing.

One can also use primers and labeled oligonucleotides having differential thermal stability. For example, the nucleotide composition of the labeled oligonucleotide can be chosen to have greater G/C content and, consequently, greater thermal stability than the primer. In similar fashion, one can incorporate modified nucleotides into the probe, which modified nucleotides contain base analogs that form more stable base pairs than the bases that are typically present in naturally occurring nucleic acids.

Modifications of the probe that may facilitate probe binding prior to primer binding to maximize the efficiency of the present assay include the incorporation of positively charged or neutral phosphodiester linkages in the probe to decrease the repulsion of the polyanionic backbones of the probe and target (see Letsinger et al., 1988, *J. Amer. Chem. Soc.* 110:4470); the incorporation of alkylated or halogenated bases, such as 5-bromouridine, in the probe to increase base stacking; the incorporation of ribonucleotides into the probe to force the probe:target duplex into an "A" structure, which has increased base stacking; and the substitution of 2,6-diaminopurine (amino adenosine) for some or all of the adenosines in the probe. In preparing such modified probes of the invention, one should recognize that the rate limiting step of duplex formation is "nucleation", the formation of a single base pair, and therefore, altering the biophysical characteristic of a portion of the probe, for instance, only the 3' or 5' terminal portion, can suffice to achieve the desired result. In addition, because the 3' terminal portion of the probe (the 3' terminal 8 to 12 nucleotides) dissociates following exonuclease degradation of the 5' terminus by the polymerase, modifications of the 3' terminus can be made without concern about interference with polymerase/nuclease activity.

The thermocycling parameters can also be varied to take advantage of the differential thermal stability of the labeled oligonucleotide and primer. For example, following the denaturation step in thermocycling, an intermediate temperature may be introduced which is permissible for labeled oligonucleotide binding but not primer binding, and then the temperature is further reduced to permit primer annealing and extension. One should note, however, that probe cleavage need only occur in later cycles of the PCR process for suitable results. Thus, one could set up the reaction mixture so that even though primers initially bind preferentially to probes, primer concentration is reduced through primer extension so that, in later cycles, probes bind preferentially to primers.

To favor binding of the labeled oligonucleotide before the primer, a high molar excess of labeled oligonucleotide to primer concentration can also be used. In this embodiment, labeled oligonucleotide concentrations are typically in the range of about 2 to 20 times higher than the respective primer concentration, which is generally $0.5–5\times10^{-7}$M. Those of skill recognize that oligonucleotide concentration, length, and base composition are each important factors that affect the $T_m$ of any particular oligonucleotide in a reaction mixture. Each of these factors can be manipulated to create a thermodynamic bias to favor probe annealing over primer annealing.

Of course, the homogeneous assay system can be applied to systems that do not involve amplification. In fact, the present invention does not even require that polymerization occur. One advantage of the polymerization-independent process lies in the elimination of the need for amplification of the target sequence. In the absence of primer extension, the target nucleic acid is substantially single-stranded. Provided the primer and labeled oligonucleotide are adjacently bound to the target nucleic acid, sequential rounds of oligonucleotide annealing and cleavage of labeled fragments can occur. Thus, a sufficient amount of labeled fragments can be generated, making detection possible in the absence of polymerization. As would be appreciated by those skilled in the art, the signal generated during PCR amplification could be augmented by this polymerization-independent activity.

In addition to the homogeneous assay systems described above, the thermostable DNA polymerases of the present invention with enhanced 5' to 3' exonuclease activity are also useful in other amplification systems, such as the transcription amplification system, in which one of the PCR primers encodes a promoter that is used to make RNA copies of the target sequence. In similar fashion, the present invention can be used in a self-sustained sequence replication (3SR) system, in which a variety of enzymes are used to make RNA transcripts that are then used to make DNA copies, all at a single temperature. By incorporating a polymerase with 5' to 3' exonuclease activity into a ligase chain reaction (LCR) system, together with appropriate oligonucleotides, one can also employ the present invention to detect LCR products.

Also, just as 5' to 3' exonuclease deficient thermostable DNA polymerases are useful in PLCR, other thermostable DNA polymerases which have 5' to 3' exonuclease activity are also useful in PLCR under different circumstances. Such is the case when the 5' tail of the downstream primer in PLCR is non-complementary to the target DNA. Such non-complementarity causes a forked structure where the 5' end of the upstream primer would normally anneal to the target DNA.

Thermostable ligases cannot act on such forked structures. However, the presence of 5' to 3' exonuclease activity in the thermostable DNA polymerase will cause the excision of the forked 5' tail of the upstream primer, thus permitting the ligase to act.

The same processes and techniques which are described above as effective for preparing thermostable DNA polymerases with attenuated 5' to 3' exonuclease activity are also effective for preparing the thermostable DNA polymerases with enhanced 5' to 3' exonuclease activity. As described above, these processes include such techniques as site-directed mutagenesis, deletion mutagenesis and "domain shuffling".

Of particular usefulness in preparing the thermostable DNA polymerases with enhanced 5' to 3' exonuclease activity is the "domain shuffling" technique described above. To briefly summarize, this technique involves the cleavage of a specific domain of a polymerase which is recognized as coding for a very active 5' to 3' exonuclease activity of that polymerase, and then transferring that domain into the appropriate area of a second thermostable DNA polymerase gene which encodes a lower level or no 5' to 20 3' exonuclease activity. The desired domain may replace a domain which encodes an undesired property of the second thermostable DNA polymerase or be added to the nucleotide sequence of the second thermostable DNA polymerase.

A particular "domain shuffling" example is set forth above in which the *Tma* DNA polymerase coding sequence comprising codons about 291 through 484 is substituted for the *Taq* DNA polymerase I codons 289 through 422. This substitution yields a novel thermostable DNA polymerase containing the 5' to 3' exonuclease domain of *Taq* DNA polymerase (codons 1–289), the 3' to 5' exonuclease domain of *Tma* DNA polymerase (codons 291–484) and the DNA polymerase domain of *Taq* DNA polymerase (codons 423–832). However, those skilled in the art will recognize that other substitutions can be made in order to construct a thermostable DNA polymerase with certain desired characteristics such as enhanced 5' to 3' exonuclease activity.

The following examples are offered by way of illustration only and are by no means intended to limit he scope of the claimed invention. In these examples, all percentages are by weight if for solids and by volume if for liquids, unless otherwise noted, and all temperatures are given in degrees Celsius.

EXAMPLE 1

Preparation of a 5' to 3' Exonuclease Mutant of *Taq* DNA Polymerase by Random Mutagenesis PCR of the Known 5' to 3' Exonuclease Domain Preparation of Insert Plasmid pLSG12 was used as a template for PCR. This plasmid is a HindIII minus version of pLSG5 in which the *Taq* polymerase gene nucleotides 616–621 of SEQ ID NO:1 were changed from AAGCTT to AAGCTG. This change eliminated the HindIII recognition sequence within the *Taq* polymerase gene without altering encoded protein sequence.

Using oligonucleotides MK61 (AGGACTACAACTGCCACACACC) (SEQ ID NO:21) and RA01 (CGAGGCGCGCCAGCCCCAGGAGATCTACCAGCTCCTTG) (SEQ ID NO:22) as primers and pLSG12 as the template, PCR was conducted to amplify a 384 bp fragment containing the ATG start of the *Taq* polymerase gene, as well as an additional 331 bp of coding sequence downstream of the ATG start codon.

A 100 μl PCR was conducted for 25 cycles utilizing the following amounts of the following agents and reactants:

50 pmol of primer MK61 (SEQ ID NO:21);

50 pmol of primer RA01 (SEQ ID NO:22);

50 μM of each dNTP;

10 mM Tris-HCl, pH 8.3;

50 mM KCl;

1.5 mM $MgCl_2$;

75.6 pg pLSG12;

2.5 units Ampli*Taq* DNA polymerase.

The PCR reaction mixture described was placed in a Perkin-Elmer Cetus Thermocycler and run through the following profile. The reaction mixture was first ramped up to 98° C. over 1 minute and 45 seconds, and held at 98° C. for 25 seconds. The reaction mixture was then ramped down to 55° C. over 45 seconds and held at that temperature for 20 seconds. Finally, the mixture was ramped up to 72° C. over 45 seconds, and held at 72° C. for 30 seconds. A final 5 minute extension occurred at 72° C.

The PCR product was then extracted with chloroform and precipitated with isopropanol using techniques which are well known in the art.

A 300 ng sample of the PCR product was digested with 20 U of HindIII (in 30 μl reaction) for 2 hours at 37° C. Then, an additional digestion was made with 8 U of BssHII for 2 hours at 50° C. This series of digestions yielded a 330 bp fragment for cloning.

A vector was prepared by digesting 5.3 pg of pLSG12 with 20 U HindIII (in 40 μl ) for 2 hours at 37° C. This digestion was followed by addition of 12 U of BssHII and incubation for 2 hours at 50° C.

The vector was dephosphorylated by treatment with CIAP (calf intestinal alkaline phosphatase), specifically 0.04 U CIAP for 30 minutes at 30° C. Then, 4 μl of 500 mM EGTA was added to the vector preparation to stop the reaction, and the phosphatase was inactivated by incubation at 65° C. for 45 minutes.

225 ng of the phosphatased vector described above was ligated at a 1:1 molar ratio with 10 ng of the PCR-derived insert.

Then, DG116 cells were transformed with one fifth of the ligation mixture, and ampicillin-resistant transformants were selected at 30° C.

Appropriate colonies were grown overnight at 30° C to $OD_{600}$ 0.7. Cells containing the $P_L$ vectors were induced at 37° C. in a shaking water bath for 4, 9, or 20 hours, and the preparations were sonicated and heat treated at 75° C. in the presence of 0.2M ammonium sulfate. Finally, the extracts were assayed for polymerase activity and 5' to 3' exonuclease activity.

The 5' to 3' exonuclease activity was quantified utilizing the 5' to 3' exonuclease assay described above. Specifically, the synthetic 3' phosphorylated oligonucleotide probe (phosphorylated to preclude polymerase extension) BW33 (GATCGCTGCGCGTAACCACCACACCCGCCGCGCp) (SEQ ID NO:13) (100 pmol) was $^{32}$P-labeled at the 5' end with gamma-[$^{32}$P] ATP (3000 Ci/mmol) and T4 polynucleotide kinase. The reaction mixture was extracted with phenol:chloroform:isoamyl alcohol, followed by ethanol precipitation. The $^{32}$P-labeled oligonucleotide probe was redissolved in 100 μl of TE buffer, and unincorporated ATP was removed by gel filtration chromatography on a Sephadex G-50 spin column. Five pmol of $^{32}$P-labeled BW33 probe, was annealed to 5 pmol of single-strand M13mp10w DNA, in the presence of 5 pmol of the synthetic oligonucleotide primer BW37 (GCGCTAGGGCGCTGGCAAGTGTAGCGGTCA) (SEQ ID NO:14) in a 100 μl reaction containing 10 mM Tris-HCl (pH 8.3), 50 mM KCl, and 3 mM $MgCl_2$. The annealing mixture was heated to 95° C. for 5 minutes, cooled to 70° C. over 10 minutes, incubated at 70° C. for an additional 10 minutes, and then cooled to 25° C. over a minute period in a Perkin-Elmer Cetus DNA thermal cycler. Exonuclease reactions containing 10 μl of the annealing mixture were pre-incubated at 70° C. for 1 minute. The thermostable DNA polymerase preparations of the invention (approximately 0.3 U of enzyme activity) were added in a 2.5 μl volume to the pre-incubation reaction, and the reaction mixture was incubated at 70° C. Aliquots (5 μl) were removed after 1 minute and 5 minutes, and stopped by the addition of 1 μl of 60 mM EDTA. The reaction products were analyzed by homochromatography and exonuclease activity was quantified following autoradiography. Chromatography was carried out in a homochromatography mix containing 2% partially hydrolyzed yeast RNA in 7M urea on Polygram CEL 300 DEAE cellulose thin layer chromatography plates. The presence of 5' to 3' exonuclease activity resulted in the generation of small $^{32}$P-labeled oligomers, which migrated up the TLC plate, and were easily differentiated on the autoradiogram from undegraded probe, which remained at the origin.

The clone 3-2 had an expected level of polymerase activity but barely detectable 5' to 3' exonuclease activity. This represented a greater than 1000-fold reduction in 5' to 3' exonuclease activity from that present in native *Taq* DNA polymerase.

This clone was then sequenced and it was found that G (137) was mutated to an A in the DNA sequence. This mutation results in a Gly (46) to Asp mutation in the amino acid sequence of the *Taq* DNA polymerase, thus yielding a thermostable DNA polymerase of the present invention with significantly attenuated 5' to 3' exonuclease activity.

The recovered protein was purified according to the *Taq* DNA polymerase protocol which is taught in Ser. No. 523,394 filed May 15, 1990, which issued as U.S. Pat. No. 5,079,352, incorporated herein by reference.

EXAMPLE 2

Construction of Met 289 (Δ289) 544 Amino Acid Form of *Taq* Polymerase

As indicated in Example 9 of U.S. Ser. No. 523,394, filed May 15, 1990, during a purification of native *Taq* polymerase an altered form of *Taq* polymerase was obtained that catalyzed the template dependent incorporation of dNTP at 70° C. This altered form of *Taq* polymerase was immunologically related to the approximate 90 kDa form of purified native *Taq* polymerase but was of lower molecular weight. Based on mobility, relative to BSA and ovalbumin following SDS-PAGE electrophoresis, the apparent molecular weight of this form is approximately 61 kDa. This altered form of the enzyme is not present in carefully prepared crude extracts of *Thermus aguaticus* cells as determined by SDS-PAGE Western blot analysis or in situ DNA polymerase activity determination (Spanos, A., and Hubscher, U. (1983) *Meth. Enz.* 91:263–277) following SDS-PAGE gel electrophoresis. This form appears to be a proteolytic artifact that may arise during sample handling. This lower molecular weight form was purified to homogeneity and subjected to N-terminal sequence determination on an ABI automated gas phase sequencer. Comparison of the obtained N-terminal sequence with the predicted amino acid sequence of the *Taq* polymerase gene (SEQ ID NO:1) indicates this shorter form arose as a result of proteolytic cleavage between Glu(289) and Ser(290).

To obtain a further truncated form of a *Taq* polymerase gene that would direct the synthesis of a 544 amino acid primary translation product plasmids pFC54.t, pSYC1578 and the complementary synthetic oligonucleotides DG29 (5'-AGCTTATGTCTCCAAAAGCT) (SEQ ID NO:23) and DG30 (5'-AGCTTTTGGAGACATA) (SEQ ID NO:24) were used. Plasmid pFC54.t was digested to completion with HindIII and BamHI. Plasmid pSYC1578 was digested with BstXI (at nucleotides 872 to 883 of SEQ ID NO:1) and treated with *E. coli* DNA polymerase I Klenow fragment in the presence of all 4 dNTPs to remove the 4 nucleotide 3' cohesive end and generate a CTG-terminated duplex blunt end encoding Leu294 in the *Taq* polymerase sequence (see *Taq* polymerase SEQ ID NO:1 nucleotides 880–882). The DNA sample was digested to completion with BglII and the approximate 1.6 kb BstXI (repaired)/BglII *Taq* DNA fragment was purified by agarose gel electrophoresis and electroelution. The pFC54.t plasmid digest (0.1 pmole) was ligated with the *Taq* polymerase gene fragment (0.3 pmole) and annealed nonphosphorylated DG29/DG30 duplex adaptor (0.5 pmole) under sticky ligase conditions at 30 μg/ml, 15° C. overnight. The DNA was diluted to approximately 10 microgram per ml and ligation continued under blunt end conditions. The ligated DNA sample was digested with XbaI to linearize (inactivate) any IL-2 mutein-encoding ligation products. 80 nanograms of the ligated and digested DNA was used to transform *E. coli* K12 strain DG116 to ampicillin resistance. Amp$^R$ candidates were screened for the presence of an approximate 7.17 kb plasmid which yielded the expected digestion products with EcoRI (4,781 bp+2,386 bp), PstI (4,138 bp+3,029 bp), ApaI (7,167 bp) and HindIII/PstI (3,400 bp+3,029 bp+738 bp). *E. coli* colonies harboring candidate plasmids were screened by single colony immunoblot for the temperature-inducible synthesis of an approximate 61 kDa *Taq* polymerase related polypeptide. In addition, candidate plasmids were subjected to DNA sequence determination at the 5' $\lambda P_L$ promoter:*Taq* DNA junction and the 3' *Taq* DNA:BT cry PRE junction. One of the plasmids encoding the intended DNA sequence and directing the synthesis of a temperature-inducible 61 kDa *Taq* polymerase related polypeptide was designated pLSG68.

Expression of 61 kDa *Taq* Pol. Cultures containing pLSG8 were grown as taught in Ser. No. 523,364 and described in Example 3 below. The 61 kDa *Taq* Pol appears not to be degraded upon heat-induction at 41° C. After 21 hours at 41° C., a heat-treated crude extract from a culture harboring pLSG8 had 12,310 units of heat-stable DNA polymerase activity per mg crude extract protein, a 24-fold increase over an uninduced culture. A heat-treated extract from a 21 hour 37° C.-induced pLSG8 culture had 9,503 units of activity per mg crude extract protein. A nine-fold increase in accumulated levels of *Taq* Pol was observed between a 5 hour and 21 hour induction at 37° C. and a nearly four-fold increase between a 5 hour and 21 hour induction at 41° C. The same total protein and heat-treated extracts were analyzed by SDS-PAGE. 20 μg crude extract protein or heat-treated crude extract from 20 μg crude extract protein were applied to each lane of the gel. The major bands readily apparent in both the 37° C. and 41° C., 21 hour-induced total protein lanes are equally intense as their heat-treated counterparts. Heat-treated crude extracts from 20 pg of total protein from 37° C. and 41° C., 21 hour samples contain 186 units and 243 units of thermostable DNA polymerase activity, respectively. To determine the usefulness of 61 kDa *Taq* DNA polymerase in PCR, PCR assays were performed using heat-treated crude extracts from induced cultures of pLSG8. Heat-treated crude extract from induced cultures of pLSG5 were used as the source of full-length *Taq* Pol in PCR. PCR product was observed in reactions utilizing 4 units and 2 units of truncated enzyme. There was more product in those PCRs than in any of the full-length enzyme reactions. In addition, no non-specific higher molecular weight products were visible.

Purification of 61 kDa *Taq* Pol. Purification of 61 kDa *Taq* Pol from induced pLSG8/DG116 cells proceeded as the purification of full-length *Taq* Pol as in Example 12 of U.S. Ser. No. 523,394, filed May 15, 1990 which issued as U.S. Pat. No. 5,079,352, with some modifications.

Induced pLSG8/DG116 cells (15.6 g) were homogenized and lysed as described in U.S. Ser. No. 523,394, filed May 15, 1990 and in Example 3 below. Fraction I contained 1.87 g protein and $1.047\times10^6$ units of activity. Fraction II, obtained as a 0.2M ammonium sulfate supernatant contained 1.84 g protein and $1.28\times10^6$ units of activity in 74 ml.

Following heat treatment, Polymin P (pH 7.5) was added slowly to 0.7%. Following centrifugation, the supernatant, Fraction III contained 155 mg protein and $1.48\times10^6$ units of activity.

Fraction III was loaded onto a 1.15×3.1 cm (3.2 ml) phenyl sepharose column at 10 ml/cm$^2$/hour. All of the applied activity was retained on the column. The column was washed with 15 ml of the equilibration buffer and then 5 ml (1.5 column volumes) of 0.1M KCl in TE. The polymerase activity was eluted with 2M urea in TE containing 20% ethylene glycol. Fractions (0.5 ml each) with polymerase activity were pooled (8.5 ml) and dialyzed into heparin sepharose buffer containing 0.1M KCl. The dialyzed material, Fraction IV (12.5 ml), contained 5.63 mg of protein and $1.29\times10^6$ units of activity.

Fraction IV was loaded onto a 1.0 ml bed volume heparin sepharose column equilibrated as above. The column was washed with 6 ml of the same buffer ($A_{280}$ to baseline) and eluted with a 15 ml linear 0.1–0.5M KCl gradient in the same buffer. Fractions (0.15 ml) eluting between 0.16 and 0.27M KCl were analyzed by SDS-PAGE. A minor (<1%) contaminating approximately 47 kDa protein copurified with 61 kDa *Taq* Pol I. Fractions eluting between 0.165 and 0.255M KCl were pooled (2.5 ml) and diafiltered on a Centricon 30 membrane into 2.5× storage buffer. Fraction V contained 2.8 mg of protein and $1.033\times10^6$ units of 61 kDa *Taq* Pol.

PCR Using Purified 61 kDa *Taq* Pol. PCR reactions (50 µl) containing 0.5 ng lambda DNA, 10 pmol each of two lambda-specific primers, 200 µM each dNTPs, 10 mM Tris-Cl, pH 8.3, 3 mM $MgCl_2$, 10 mM KCl and 3.5 units of 61 kDa *Taq* Pol were performed. As a comparison, PCR reactions were performed with 1.25 units of full-length *Taq* Pol, as above, with the substitution of 2 mM $MgCl_2$ and 50 mM KCl. Thermocycling conditions were 1 minute at 95° C. and 1 minute at 60° C. for 23 cycles, with a final 5 minute extension at 75° C. The amount of DNA per reaction was quantitated by the Hoechst fluorescent dye assay. 1.11 µg of product was obtained with 61 kDa *Taq* Pol ($2.2\times10^5$-fold amplification), as compared with 0.70 µg of DNA with full-length *Taq* Pol ($1.4\times10^5$-fold amplification).

Thermostability of 61 kDa *Taq* Pol. Steady state thermal inactivation of recombinant 94 kDa *Taq* Pol and 61 kDa *Taq* Pol was performed at 97.5° C. under buffer conditions mimicking PCR. 94 kDa *Taq* Pol has an apparent half-life of approximately 9 minute at 97.5° C., whereas the half-life of 61 kDa *Taq* Pol was approximately 21 minutes. The thermal inactivation of 61 kDa *Taq* Pol was unaffected by KCl concentration over a range from 0 to 50 mM.

Yet another truncated *Taq* polymerase gene contained within the ~2.68 kb HindIII-Asp718 fragment of plasmid pFC85 can be expressed using, for example, plasmid $P_LN_{RBS}$ATG, by operably linking the amino-terminal HindIII restriction site encoding the *Taq* pol gene to an ATG initiation codon. The product of this fusion upon expression will yield an ~70,000–72,000 dalton truncated polymerase.

This specific construction can be made by digesting plasmid pFC85 with HindIII and treating with Klenow fragment in the presence of DATP and dGTP. The resulting fragment is treated further with S1 nuclease to remove any single-stranded extensions and the resulting DNA digested with AsP718 and treated with Klenow fragment in the presence of all four dNTPs. The recovered fragment can be ligated using T4 DNA ligase to dephosphorylated plasmid $P_LN_{RBS}$ATG, which had been digested with SacI and treated with Klenow fragment in the presence of dGTP to construct an ATG blunt end. This ligation mixture can then be used to transform *E. coli* DG116 and the transformants screened for production of *Taq* polymerase. Expression can be confirmed by Western immunoblot analysis and activity analysis.

EXAMPLE 3

Construction, Expression and Purification of a Truncated 5' to 3' Exonuclease Deficient *Tma* Polymerase (MET284)

To express a 5' to 3' exonuclease deficient *Tma* DNA polymerase lacking amino acids 1–283 of native *Tma* DNA polymerase the following steps were performed.

Plasmid pTma12-1 was digested with BspHI (nucleotide position 848) and HindIII (nucleotide position 2629). A 1781 base pair fragment was isolated by agarose gel purification. To separate the agarose from the DNA, a gel slice containing the desired fragment was frozen at −20° C. in a Costar spinex filter unit. After thawing at room temperature, the unit was spun in a microfuge. The filtrate containing the DNA was concentrated in a Speed Vac concentrator, and the DNA was precipitated with ethanol.

The isolated fragment was cloned into plasmid pTma12-1 digested with NcoI and HindIII. Because NcoI digestion leaves the same cohesive end sequence as digestion with BspHI, the 1781 base pair fragment has the same cohesive ends as the full length fragment excised from plasmid pTma12-1 by digestion with NcoI and HindIII. The ligation of the isolated fragment with the digested plasmid results in a fragment switch and was used to create a plasmid designated pTma14.

Plasmid pTma15 was similarly constructed by cloning the same isolated fragment into pTma13. As with pTma14, pTma15 drives expression of a polymerase that lacks amino acids 1 through 283 of native *Tma* DNA polymerase; translation initiates at the methionine codon at position 284 of the native coding sequence.

Both the pTma14 and pTma15 expression plasmids expressed at a high level a biologically active thermostable DNA polymerase devoid of 5' to 3' exonuclease activity of molecular weight of about 70 kDa; plasmid pTma15 expressed polymerase at a higher level than did pTma14. Based on similarities with *E. coli* Pol Klenow fragment, such as conservation of amino acid sequence motifs in all three domains that are critical for 3' to 5' exonuclease activity, distance from the amino terminus to the first domain critical for exonuclease activity, and length of the expressed protein, the shortened form (MET284) of *Tma* DNA polymerase exhibits 3' to 5' exonuclease or proof-reading activity but lacks 5' to 3' exonuclease activity. Initial SDS activity gel assays and solution assays for 3' to 5' exonuclease activity suggest attenuation in the level of proof-reading activity of the polymerase expressed by *E. coli* host cells harboring plasmid pTma15.

MET284 *Tma* DNA polymerase was purified from *E. coli* strain DG116 containing plasmid pTma15. The seed flask for a 10 L fermentation contained tryptone (20 g/l), yeast extract (10 g/l), NaCl (10 g/l), glucose (10 g/l), ampicillin (50 mg/l), and thiamine (10 mg/l). The seed flask was innoculated with a colony from an agar plate (a frozen glycerol culture can be used). The seed flask was grown at 30° C. to between 0.5 to 2.0 O.D. ($A_{680}$). The volume of seed culture inoculated into the fermentor is calculated such that the bacterial concentration is 0.5 mg dry weight/liter. The 10 liter growth medium contained 25 mM $KH_2PO_4$, 10 mM $(NH_4)_2SO_4$, 4 mM sodium citrate, 0.4 mM $FeCl_3$, 0.04 mM $ZnCl_2$, 0.03 mM $CoCl_2$, 0.03 mM $CuCl_2$, and 0.03 mM $H_3BO_3$. The following sterile components were added: 4 mM $MgSO_4$, 20 g/l glucose, 20 mg/l thiamine, and 50 mg/l ampicillin. The pH was adjusted to 6.8 with NaOH and controlled during the fermentation by added $NH_4OH$. Glucose was continually added by coupling to $NH_4OH$ addition. Foaming was controlled by the addition of propylene glycol as necessary, as an antifoaming agent. Dissolved oxygen concentration was maintained at 40%.

The fermentor was inoculated as described above, and the culture was grown at 30° C. to a cell density of 0.5 to $1.0\times10^{10}$ cells/ml (optical density [$A_{680}$] of 15). The growth temperature was shifted to 38° C. to induce the synthesis of MET284 *Tma* DNA polymerase. The temperature shift increases the copy number of the pTma15 plasmid and simultaneously derepresses the lambda $P_L$ promoter controlling transcription of the modified *Tma* DNA polymerase gene through inactivation of the temperature-sensitive cI repressor encoded by the defective prophage lysogen in the host.

The cells were grown for 6 hours to an optical density of 37 ($A_{680}$) and harvested by centrifugation. The cell mass (ca. 95 g/l) was resuspended in an equivalent volume of buffer containing 50 mM Tris-Cl, pH 7.6, 20 mM EDTA and 20% (w/v) glycerol. The suspension was slowly dripped into liquid nitrogen to freeze the suspension as "beads" or small pellets. The frozen cells were stored at −70° C.

To 200 g of frozen beads (containing 100 g wet weight cell) were added 100 ml of 1× TE (50 mM Tris-Cl, pH 7.5, 10 mM EDTA) and DTT to 0.3 mM, PMSF to 2.4 mM, leupeptin to 1 μg/ml and TLCK (a protease inhibitor) to 0.2 mM. The sample was thawed on ice and uniformly resuspended in a blender at low speed. The cell suspension was lysed in an Aminco french pressure cell at 20,000 psi. To reduce viscosity, the lysed cell sample was sonicated 4 times for 3 min. each at 50% duty cycle and 70% output. The sonicate was adjusted to 550 ml with 1× TE containing 1 mM DTT, 2.4 mM PMSF, 1 μg/ml leupeptin and 0.2 mM TLCK (Fraction I). After addition of ammonium sulfate to 0.3M, the crude lysate was rapidly brought to 75° C. in a boiling water bath and transferred to a 75° C. water bath for 15 min. to denature and inactivate *E. coli* host proteins. The heat-treated sample was chilled rapidly to 0° C. and incubated on ice for 20 min. Precipitated proteins and cell membranes were removed by centrifugation at 20,000×G for 30 min. at 5° C. and the supernatant (Fraction II) saved.

The heat-treated supernatant (Fraction II) was treated with polyethyleneimine (PEI) to remove most of the DNA and RNA. Polymin P (34.96 ml of 10% [w/v], pH 7.5) was slowly added to 437 ml of Fraction II at 0° C. while stirring rapidly. After 30 min. at 0° C., the sample was centrifuged at 20,000 ×G for 30 min. The supernatant (Fraction III) was applied at 80 ml/hr to a 100 ml phenylsepharose column (3.2×12.5 cm) that had been equilibrated in 50 mM Tris-Cl, pH 7.5, 0.3M ammonium sulfate, 10 mM EDTA, and 1 mM DTT. The column was washed with about 200 ml of the same buffer ($A_{280}$ to baseline) and then with 150 ml of 50 mM Tris-Cl, pH 7.5, 100 mM KCl, 10 mM EDTA and 1 mM DTT. The MET284 *Tma* DNA polymerase was then eluted from the column with buffer containing 50 mM Tris-Cl, pH 7.5, 2M urea, 20% (w/v) ethylene glycol, 10 mM EDTA, and 1 mM DTT, and fractions containing DNA polymerase activity were pooled (Fraction IV).

Fraction IV is adjusted to a conductivity equivalent to 50 mM KCl in 50 mM Tris-Cl, pH 7.5, 1 mM EDTA, and 1 mM DTT. The sample was applied (at 9 ml/hr) to a 15 ml heparinsepharose column that had been equilibrated in the same buffer. The column was washed with the same buffer at ca. 14 ml/hr (3.5 column volumes) and eluted with a 150 ml 0.05 to 0.5M KCl gradient in the same buffer. The DNA polymerase activity eluted between 0.11–0.22M KCl. Fractions containing the pTma15 encoded modifed *Tma* DNA polymerase are pooled, concentrated, and diafiltered against 2.5× storage buffer (50 mM Tris-Cl, pH 8.0, 250 mM KCl, 0.25 mM EDTA, 2.5 mM DTT, and 0.5% Tween 20), subsequently mixed with 1.5 volumes of sterile 80% (w/v) glycerol, and stored at −20° C. Optionally, the heparin sepharose-eluted DNA polymerase or the phenyl sepharose-eluted DNA polymerase can be dialyzed or adjusted to a conductivity equivalent to 50 mM KCl in 50 mM Tris-Cl, pH 7.5, 1 mM DTT, 1 mM EDTA, and 0.2% Tween 20 and applied (1 mg protein/ml resin) to an affigel blue column that has been equilibrated in the same buffer. The column is washed with three to five column volumes of the same buffer and eluted with a 10 column volume KCl gradient (0.05 to 0.8M) in the same buffer. Fractions containing DNA polymerase activity (eluting between 0.25 and 0.4M KCl) are pooled, concentrated, diafiltered, and stored as above.

The relative thermoresistance of various DNA polymerases has been compared. At 97.5° C. the half-life of native *Tma* DNA polymerase is more than twice the half-life of either native or recombinant *Taq* (i.e., AmpliTaq ) DNA polymerase. Surprisingly, the half-life at 97.5° C. of MET284 *Tma* DNA polymerase is 2.5 to 3 times longer than the half-life of native *Tma* DNA polymerase.

PCR tubes containing 10 mM Tris-Cl, pH 8.3, and 1.5 mM $MgCl_2$ (for *Taq* or native *Tma* DNA polymerase) or 3 mM $MgCl_2$ (for MET284 *Tma* DNA polymerase), 50 mM KCl (for *Taq*, native *Tma* and MET284 *Tma* DNA polymerases) or no KCl (for MET284 *Tma* DNA polymerase), 0.5 μM each of primers PCR01 and PCR02, 1 ng of lambda template DNA, 200 μM of each dNTP except dCTP, and 4 units of each enzyme were incubated at 97.5° C. in a large water bath for times ranging from 0 to 60 min. Samples were withdrawn with time, stored at 0° C., and 5 μl assayed at 75° C. for 10 min. in a standard activity assay for residual activity.

*Taq* DNA polymerase had a half-life of about 10 min. at 97.5° C., while native *Tma* DNA polymerase had a half-life of about 21 to 22 min. at 97.5° C. Surprisingly, the MET284 form of *Tma* DNA polymerase had a significanlty longer half-life (50 to 55 min.) than either *Taq* or native *Tma* DNA polymerase. The improved thermoresistance of MET284 *Tma* DNA polymerase will find applications in PCR, particularly where G+C-rich targets are difficult to amplify because the strand-separation temperature required for complete denaturation of target and PCR product sequences leads to enzyme inactivation.

PCR tubes containing 50 μl of 10 mM Tris-Cl, pH 8.3, 3 mM $MgCl_2$, 200 μM of each dNTP, 0.5 ng bacteriophage lambda DNA, 0.5 μM of primer PCR01, 4 units of MET284 *Tma* DNA polymerase, and 0.5 μM of primer PCR02 or PL10 were cycled for 25 cycles using $T_{den}$ of 96° C. for 1 min. and $T_{anneal\text{-}extend}$ of 60° C. for 2 min. Lambda DNA template, deoxynucleotide stock solutions, and primers PCR01 and PCR02 were part of the PECI GeneAmp kit. Primer PL10 has the sequence: 5'-GGCGTACCTTTGTCTCACGGGCAAC-3' (SEQ ID NO:25) and is complementary to bacteriophage lambda nucleotides 8106–8130.

The primers PCR01 and PCR02 amplify a 500 bp product from lambda. The primer pair PCR01 and PL10 amplify a 1 kb product from lambda. After amplification with the respective primer sets, 5 µl aliquots were subjected to agarose gel electrophoresis and the specific intended product bands visualized with ethidium bromide staining. Abundant levels of product were generated with both primer sets, showing that MET284 *Tma* DNA polymerase successfully amplified the intended target sequence.

EXAMPLE 4

Expression of Truncated *Tma* DNA Polymerase

To express a 5' to 3' exonuclease deficient form of *Tma* DNA polymerase which initiates translation at MET, the coding region corresponding to amino acids 1 through 139 was deleted from the expression vector. The protocol for constructing such a deletion is similar to the constructions described in Examples 2 and 3: a shortened gene fragment is excised and then reinserted into a vector from which a full length fragment has been excised. However, the shortened fragment can be obtained as a PCR amplification product rather than purified from a restriction digest. This methodology allows a new upstream restriction site (or other sequences) to be incorporated where useful.

To delete the region up to the methionine codon at position 140, an SphI site was introduced into pTma12-1 and pTma13 using PCR. A forward primer corresponding to nucleotides 409–436 of *Tma* DNA polymerase SEQ ID NO:3 (FL63) was designed to introduce an SphI site just upstream of the methionine codon at position 140. The reverse primer corresponding to the complement of nucleotides 608–634 of *Tma* DNA polymerase SEQ ID NO:3 (FL69) was chosen to include an XbaI site at position 621. Plasmid pTma12-1 linearized with SmaI was used as the PCR template, yielding an approximate 225 bp PCR product.

Before digestion, the PCR product was treated with 50 µg/ml of Proteinase K in PCR reaction mix plus 0.5% SDS and 5 mM EDTA. After incubating for 30 minutes at 37° C., the Proteinase K was heat inactivated at 68° C. for 10 minutes. This procedure eliminated any *Taq* polymerase bound to the product that could inhibit subsequent restriction digests. The buffer was changed to a TE buffer, and the excess PCR primers were removed with a Centricon 100 microconcentrator.

The amplified fragment was digested with SphI, then treated with Klenow to create a blunt end at the SphI-cleaved end, and finally digested with XbaI. The resulting fragment was ligated with plasmid pTma13 (pTma12-1 would have been suitable) that had been digested with NcoI, repaired with Klenow, and then digested with XbaI. The ligation yielded an in-frame coding sequence with the region following the NcoI site (at the first methionine codon of the coding sequence) and the introduced SphI site (upstream of the methionine codon at position 140) deleted. The resulting expression vector was designated pTma16.

The primers used in this example are given below and in the Sequence Listing section.

| Primer | SEQ ID NO: | Sequence |
|---|---|---|
| FL63 | SEQ ID NO: 26 | 5'GATAAAGGCATGCTTCAGCTTGTGAACG |
| FL69 | SEQ ID NO: 27 | 5'TGTACTTCTCTAGAAGCTGAACAGCAG |

EXAMPLE 5

Elimination of Undesired RBS in MET140 Expression Vectors

Reduced expression of the MET140 form of *Tma* DNA polymerase can be achieved by eliminating the ribosome binding site (RBS) upstream of the methionine codon at position 140. The RBS was be eliminated via oligonucleotide site-directed mutagenesis without changing the amino acid sequence. Taking advantage of the redundancy of the genetic code, one can make changes in the third position of codons to alter the nucleic acid sequence, thereby eliminating the RBS, without changing the amino acid sequence of the encoded protein.

A mutagenic primer (FL64) containing the modified sequence was synthesized and phosphorylated. Single-stranded pTma09 (a full length clone having an NcoI site) was prepared by coinfecting with the helper phage R408, commercially available from Stratagene. A "gapped duplex" of single stranded pTma09 and the large fragment from the PvuII digestion of pBS13+ was created by mixing the two plasmids, heating to boiling for 2 minutes, and cooling to 65° C. for 5 minutes. The phosphorylated primer was then annealed with the "gapped duplex" by mixing, heating to 80° C. for 2 minutes, and then cooling slowly to room temperature. The remaining gaps were filled by extension with Klenow and the fragments ligated with T4 DNA ligase, both reactions taking place in 200 µM of each dNTP and 40 µM ATP in standard salts at 37° C. for 30 minutes.

The resulting circular fragment was transformed into DG101 host cells by plate transformations on nitrocellulose filters. Duplicate filters were made and the presence of the correct plasmid was detected by probing with a $^{32}$P-phosphorylated probe (FL65). The vector that resulted was designated pTma19.

The RBS minus portion from pTma19 was cloned into pTma12-1 via an NcoI/XbaI fragment switch. Plasmid pTma19 was digested with NcoI and XbaI, and the 620 bp fragment was purified by gel electrophoresis, as in Example 3, above. Plasmid pTma12-1 was digested with NcoI, XbaI, and XcmI. The XcmI cleavage inactivates the RBS+ fragment for the subsequent ligation step, which is done under conditions suitable for ligating "sticky" ends (dilute ligase and 40 µM ATP). Finally, the ligation product is transformed into DG116 host cells for expression and designated pTma19-RBS.

The oligonucleotide sequences used in this example are listed below and in the Sequence Listing section.

| Oligo | SEQ ID NO: | Sequence |
|---|---|---|
| FL64 | SEQ ID NO:28 | 5'CTGAAGCATGTCTTTGTCACCGGT-TACTATGAATAT |
| FL65 | SEQ ID NO:29 | 5'TAGTAACCGGTGACAAAG |

EXAMPLE 6

Expression of Truncated *Tma* DNA Polymerases MET-ASP21 and MET-GLU74

To effect translation initiation at the aspartic acid codon at position 21 of the *Tma* DNA polymerase gene coding sequence, a methionine codon is introduced before the codon, and the region from the initial NcoI site to this introduced methionine codon is deleted. Similar to Example 4, the deletion process involved PCR with the same downstream primer described above (FL69) and an upstream primer (FL66) designed to incorporate an NcoI site and a methionine codon to yield a 570 base pair product.

The amplified product was concentrated with a Centricon-100 microconcentrator to eliminate excess primers and buffer. The product was concentrated in a Speed Vac concentrator and then resuspended in the digestion mix. The amplified product was digested with NcoI and XbaI. Likewise, pTma12-1, pTma13, or pTma19-RBS was digested with the same two restriction enzymes, and the digested, amplified fragment is ligated with the digested expression vector. The resulting construct has a deletion from the NcoI site upstream of the start codon of the native *Tma* coding sequence to the new methionine codon introduced upstream of the aspartic acid codon at position 21 of the native *Tma* coding sequence.

Similarly, a deletion mutant was created such that translation initiation begins at Glu74, the glutamic acid codon at position 74 of the native *Tma* coding sequence. An upstream primer (FL67) is designed to introduce a methionine codon and an NcoI site before Glu74. The downstream primer and cloning protocol used are as described above for the MET-ASP21 construct.

The upstream primer sequences used in this example are listed below and in the Sequence Listing section.

| Oligo | SEQ ID NO: | Sequence |
|---|---|---|
| FL66 | SEQ ID NO:30 | 5'CTATGCCATGGATAGATCGCTT-TCTACTTCC |
| FL67 | SEQ ID NO:31 | 5'CAAGCCCATGGAAACTTACAAG-GCTCAAAGA |

EXAMPLE 7

Expression of Truncated *Taf* Polymerase

Mutein forms of the *Taf* polymerase lacking 5' to 3' exonuclease activity were constructed by introducing deletions in the 5' end of the *Taf* polymerase gene. Both 279 and 417 base pair deletions were created using the following protocol; an expression plasmid was digested with restriction enzymes to excise the desired fragment, the fragment ends were repaired with Klenow and all four dNTP/s, to produce blunt ends, and the products were ligated to produce a new circular plasmid with the desired deletion. To express a 93 kilodalton, 5' to 3' exonuclease-deficient form of *Taf* polymerase, a 279 bp deletion comprising amino acids 2–93 was generated. To express an 88 kilodalton, 5' to 3' exonuclease-deficient form of *Taf* polymerase, 417 bp deletion comprising amino acids 2–139 was generated.

To create a plasmid with codons 2–93 deleted, pTaf03 was digested with NcoI and NdeI and the ends were repaired by Klenow treatment. The digested and repaired plasmid was diluted to 5 µg/ml and ligated under blunt end conditions. The dilute plasmid concentration favors intramolecular ligations. The ligated plasmid was transformed into DG116. Mini-screen DNA preparations were subjected to restriction analysis and correct plasmids were confirmed by DNA sequence analysis. The resulting expression vector created by deleting a segment from pTaf03 was designated pTaf09. A similar vector created from pTaf05 was designated pTaf10.

Expression vectors also were created with codons 2–139 deleted. The same protocol was used with the exception that the initial restriction digestion was performed with NcoI and BglII. The expression vector created from pTaf03 was designated pTaf and the expression vector created from pTaf05 was designated pTaf12.

EXAMPLE 8

Derivation and Expression of 5' to 3' Exonuclease-Deficient, Thermostable DNA Polymerase of Thermus species, Z05 Comprising Amino Acids 292 Through 834

To obtain a DNA fragment encoding a 5' to 3' exonuclease-deficient thermostable DNA polymerase from Thermus species Z05, a portion of the DNA polymerase gene comprising amino acids 292 through 834 is selectively amplified in a PCR with forward primer TZA292 and reverse primer TZR01 as follows:

50 poles TZA292

50 poles TZR01

10 ng Thermus sp. Z05 genomic DNA 2.5 units AmpliTaq DNA polymerase

50 µM each dATP, dGTP, dCTP, dTTP in an 80 µl solution containing 10 mM Tris-HCl pH 8.3, 50 mM KCl and overlaid with 100 µl of mineral oil. The reaction was initiated by addition of 20 µl containing 7.5 mM $MgCl_2$ after the tubes had been placed in an 80° C preheated cycler.

The genomic DNA was digested to completion with restriction endonuclease Asp718, denatured at 98° C. for 5 minutes and cooled rapidly to 0° C. The sample was cycled in a Perkin-Elmer Cetus Thermal Cycler according to the following profile:

STEP CYCLE to 96° C. and hold for 20 seconds.

STEP CYCLE to 55° C. and hold for 30 seconds.

RAMP to 72° C. over 30 seconds and hold for 1 minute.

REPEAT profile for 3 cycles.

STEP CYCLE to 96° C. and hold for 20 seconds.

STEP CYCLE to 65° C. and hold for 2 minutes.

REPEAT profile for 25 cycles.

After last cycle HOLD for 5 minutes.

The intended 1.65 kb PCR product is purified by agarose gel electrophoresis, and recovered following phenol-chloroform extraction and ethanol precipitation. The purified product is digested with restriction endonucleases NdeI and BglII and ligated with NdeI/BamHI-digested and dephosphorylated plasmid vector pDG164 (at Example 6*b*, U.S. Ser. No. 455,967, filed Dec. 22, 1989, which was filed in the PCT as PCT/US90/07639 and published on Jul. 11, 1991, and which is incorporated herein by reference). Ampicillin-resistant transformants of *E. coli* strain DG116 are selected at 30° C. and screened for the desired recombinant plasmid. Plasmid pZ05A292 encodes a 544 amino acid, 5' to 3' exonuclease-deficient Thermus sp.

Z05 thermostable DNA polymerase analogous to the pLSG8 encoded protein of Example 2. The DNA polymerase activity is purified as in Example 2. The purified protein is deficient in 5' to 3' exonuclease activity, is more thermoresistant than the corresponding native enzyme and is particularly useful in PCR of G+C-rich templates.

| Primer | SEQ ID NO: | SEQUENCE |
|---|---|---|
| TZA292 | SEQ ID NO: 32 | GTCGGCATATGGCTCCTGCTCCTCTTGAGGA-GGCCCCCTGGCCCCCGCC |
| TZR01 | SEQ ID NO: 33 | GACGCAGATCTCAGCCCTTGGCGGAAAGCCA-GTCCTC |

| Primer | SEQ ID NO: | SEQUENCE |
|---|---|---|
| TSA288 | SEQ ID NO: 34 | GTCGGCATATGGCTCCTAAAGAAGCTGAGGA-GGCCCCCTGGCCCCCGCC |
| TSR01 | SEQ ID NO: 35 | GACGCAGATCTCAGGCCTTGGCGGAAAGCCA-GTCCTC |

EXAMPLE 9

Derivation and Expression of 5' to 3' Exonuclease-Deficient, Thermostable DNA Polymerase of Thermus species SPS17 Comprising Amino Acids 288 Through 830

To obtain a DNA fragment encoding 5' to 3' exonuclease-deficient thermostable DNA polymerase from Thermus species SPS17, a portion of the DNA polymerase gene comprising amino acids 288 through 830 is selectively amplified in a PCR with forward primer TSA288 and reverse primer TSR01 as follows:

50 pmoles TSA288

50 pmoles TSR01

10 ng Thermus sp. SPS17 genomic DNA 2.5 units AmpliTaq DNA polymerase

50 μM each DATP, dGTP, dCTP, dTTP in an 80 μl solution containing 10 mM Tris-HCl pH 8.3, 50 mM KCl and overlaid with 100 μl of mineral oil. The reaction was initiated by addition of 20 μl containing 7.5 mM $MgCl_2$ after the tubes had been placed in an 80° C. preheated cycler.

The genomic DNA was denatured at 98° C. for 5 minutes and cooled rapidly to 0C. The sample was cycled in a Perkin-Elmer Cetus Thermal Cycler according to the following profile:

STEP CYCLE to 96° C. and hold for 20 seconds.

STEP CYCLE to 55° C. and hold for 30 seconds.

RAMP to 72° C. over 30 seconds and hold for 1 minute.

REPEAT profile for 3 cycles.

STEP CYCLE to 96° C. and hold for 20 seconds.

STEP CYCLE to 65° C. and hold for 2 minutes.

REPEAT profile for 25 cycles.

After last cycle HOLD for 5 minutes.

The intended 1.65 kb PCR product is purified by agarose gel electrophoresis, and recovered following phenol-chloroform extraction and ethanol precipitation. The purified product is digested with restriction endonucleases NdeI and BglII and ligated with NdeI/BamHI-digested and dephosphorylated plasmid vector pDG164 (at Example 6*b*, U.S. Ser. No. 455,967, filed Dec. 12, 1989, which was filed in the PCT as PCT/US90/07639 and published on Jul. 11, 1991, and which is Ampicillin-resistant transformants of *E. coli* strain DG116 are selected at 30° C. and screened for the desired recombinant plasmid. Plasmid pSPSA288 encodes a 544 amino acid, 5' to 3' exonuclease-deficient Thermus sp. SPS17 thermostable DNA polymerase analogous to the pLSG8 encoded protein of Example 2. The DNA polymerase activity is purified as in Example 2. The purified protein is deficient in 5' to 3' exonuclease activity, is more thermoresistant than the corresponding native enzyme and is particularly useful in PCR of G+C-rich templates.

EXAMPLE 10

Derivation and Expression of 5' to 3' Exonuclease-Deficient, Thermostable DNA Polymerase of *Thermus Thermophilus* Comprising Amino Acids 292 Through 834

To obtain a DNA fragment encoding a 5' to 3' exonuclease-deficient thermostable DNA polymerase from *Thermus thermophilus*, a portion of the DNA polymerase gene comprising amino acids 292 through 834 is selectively amplified in a PCR with forward primer TZA292 and reverse primer DG122 as follows;

50 pmoles TZA292

50 pmoles DG122

1 ng EcoRI digested plasmid pLSG22

2.5 units AmpliTaq DNA polymerase

50 μM each dATP, dGTP, dCTP, dTTP in an 80 μl solution containing 10 mM Tris-HCl pH 8.3, 50 mM KCl and overlaid with 100 μl of mineral oil. The reaction was initiated by addition of 20 μl containing 7.5 mM $MgCl_2$ after the tubes had been placed in an 80° C. preheated cycler.

Plasmid pLSG22 (at Example 4a, U.S. Ser. No. 455,967, filed Dec. 22, 1989, which was filed in the PCT as PCT/US90/07639 and published on Jul. 11, 1991, and which is incorporated herein by reference) was digested to completion with restriction endonuclease EcoRI, denatured at 98° C. for 5 minutes and cooled rapidly to 0° C. The sample was cycled in a Perkin-Elmer Cetus Thermal Cycler according to the following profile:

STEP CYCLE to 96° C. and hold for 20 seconds.

STEP CYCLE to 55° C. and hold for 30 seconds.

RAMP to 72° C. over 30 seconds and hold for 1 minute.

REPEAT profile for 3 cycles.

STEP CYCLE to 96° C. and hold for 20 seconds.

STEP CYCLE to 65° C. and hold for 2 minutes.

REPEAT profile for 20 cycles.

After last cycle HOLD for 5 minutes.

The intended 1.66 kb PCR product is purified by agarose gel electrophoresis, and recovered following phenol-chloroform extraction and ethanol precipitation. The purified product is digested with restriction endonucleases NdeI and BglII and ligated with NdeI/BamHI-digested and dephosphorylated plasmid vector pDG164 (U.S. Ser. No. 455,967, filed Dec. 12 1989, Example 6B). Ampicillin-resistant transformants of *E. coli* strain DG116 are selected at 30° C. and screened for the desired recombinant plasmid. Plasmid pTTHA292 encodes a 544 amino acid, 5' to 3' exonuclease-deficient *Thermus thermophilus* thermostable DNA polymerase analogous to the pLSG8 encoded protein of Example 2. The DNA polymerase activity is purified as in Example 2. The purified protein is deficient in 5' to 3' exonuclease activity, is more thermoresistant than the corresponding native enzyme and is particularly useful in PCR of G+C-rich templates.

| Primer | SEQ ID NO: | SEQUENCE |
|---|---|---|
| TZA292 | SEQ ID NO:32 | GTCGGCATATGGCTCCTGCTCCTCTTGAGGA-GGCCCCCTGGCCCCCGCC |
| DG122 | SEQ ID NO:36 | CCTCTAAACGGCAGATCTGATATCAACCCTT-GGCGGAAAGC |

EXAMPLE 11

Derivation and Expression of 5' to 3' Exonuclease-Deficient, Thermostable DNA Polymerase of *Thermosipho africanus* Comprising Amino Acids 285 Through 892

To obtain a DNA fragment encoding a 5' to 3' exonuclease-deficient thermostable DNA polymerase from *Thermosipho africanus*, a portion of the DNA polymerase gene comprising amino acids 285 through 892 is selectively amplified in a PCR with forward primer TAFI285 and reverse primer TAFR01 as follows:

50 pmoles TAFI285

50 pmoles TAFR01

1 ng plasmid pBSM:TafRV3' DNA 2.5 units AmpliTaq DNA polymerase

50 μM each dATP, dGTP, dCTP, dTTP in an 80 μl solution containing 10 mM Tris-HCl pH 8.3, 50 mM KCl and overlaid with 100 μl of mineral oil. The reaction was initiated by addition of 20 μl containing 7.5 mM $MgCl_2$ after the tubes had been placed in an 80° C. preheated cycler.

Plasmid pBSM:TafRV'3 (obtained as described in PCT patent application Ser. No. PCT/US91/07076, which published on Apr. 16, 1992, at, EX 4, page 53, incorporated herein by reference) was digested with EcoRI to completion and the DNA was denatured at 98° C. for 5 minutes and cooled rapidly to 0° C. The sample was cycled in a Perkin-Elmer Cetus Thermal Cycler according to the following profile:

STEP CYCLE to 95° C. and hold for 30 seconds.

STEP CYCLE to 55° C. and hold for 30 seconds.

RAMP to 72° C. over 30 seconds and hold for 1 minute.

REPEAT profile for 3 cycles.

STEP CYCLE to 95° C. and hold for 30 minutes.

STEP CYCLE to 65° C. and hold for 2 minutes.

REPEAT profile for 20 cycles.

After last cycle HOLD for 5 minutes.

The intended 1.86 kb PCR product is purified by agarose gel electrophoresis, and recovered following phenol-chloroform extraction and ethanol precipitation.

The purified product is digested with restriction endonucleases NdeI and BamHI and ligated with NdeI/BamHI-digested and dephosphorylated plasmid vector pDG164 (Example 6b, U.S. Ser. No. 455,967, filed Dec. 22, 1989, which was filed in the PCT as PCT/US90/07639 and published on Jul. 11, 1991. Ampicillin- resistant transformants of *E. coli* strain DG116 are selected at 30° C. and screened for the desired recombinant plasmid. Plasmid pTAFI285 encodes a 609 amino acid, 5' to 3' exonuclease-deficient *Thermosipho africanus* thermostable DNA polymerase analogous to the pTMA15-encoded protein of Example 3. The DNA polymerase activity is purified as in Example 3. The purified protein is deficient in 5' to 3' exonuclease activity, is more thermoresistant than the corresponding native enzyme and is particularly useful in PCR of G+C-rich templates.

| Primer | SEQ ID NO: | SEQUENCE |
|---|---|---|
| TAFI285 | SEQ ID NO:37 | GTCGGCATATGATTAAAGAACTTAATTTACA-AGAAAAATTAGAAAAGG |
| TAFR01 | SEQ ID NO:38 | CCTTTACCCCAGGATCCTCATTCCCACTCTT-TTCCATAATAAACAT |

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposits of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown and described herein will become apparent to those skilled in the art from the foregoing description and fall within the scope of the appended claims.

What is claimed is:

1. A recombinant thermostable DNA polymerase enzyme that is a mutant form of a full-length thermostable DNA polymerase, wherein said full-length thermostable DNA polymerase has an amino acid sequence comprising a first amino acid subsequence that is SEQ ID NO:15 (Ala Xaa Tyr Gly, wherein Xaa is Val or Thr) and a second amino acid subsequence that is SEQ ID NO:20 (Xaa Xaa Xaa Xaa Tyr Lys Ala, wherein the first Xaa is lie or Leu), wherein said mutant form is an N-terminal deletion mutant of said amino acid sequence, wherein said N-terminal deletion extends at least through said first amino acid subsequence and not beyond said second amino acid subsequence, wherein said mutant form has a lesser amount of 5' to 3' exonuclease activity than that of said full-length thermostable DNA polymerase.

2. The recombinant thermostable DNA polymerase enzyme of claim 1 wherein said enzyme is selected from the group consisting of mutant forms of Thermus species sps17, Thermus species Z05, *Thermus aquaticus*, *Thermus thermophilus*, *Thermosipho africanus*, and *Thermotoga maritima* DNA polymerases.

3. The recombinant thermostable DNA polymerase enzyme of claim 2 wherein said enzyme is a mutant form of Thermus species sps17 comprising amino acids 74–830 of SEQ ID NO:6.

4. The recombinant thermostable DNA polymerase enzyme of claim 2 wherein said enzyme is a mutant form of *Thermus aquaticus* comprising amino acids 77–832 of SEQ ID NO:2.

5. The recombinant thermostable DNA polymerase enzyme of claim 2 wherein said enzyme is a mutant form of *Thermus aquaticus* comprising amino acids 47–832 of SEQ ID NO:2.

6. The recombinant thermostable DNA polymerase enzyme of claim 2 wherein said enzyme is a mutant form of *Thermotocra maritima* comprising amino acids 38–893 of SEQ ID NO:4.

7. The recombinant thermostable DNA polymerase enzyme of claim 2 wherein said enzyme is a mutant form of *Thermotoga* maritima comprising amino acids 74–893 of SEQ ID NO:4.

8. The recombinant thermostable DNA polymerase enzyme of claim 2 wherein said enzyme is a mutant form of Thermus species sps17 comprising amino acids 44–830 of SEQ ID NO:6.

9. The recombinant thermostable DNA polymerase enzyme of claim 2 wherein said enzyme is a mutant form of Thermus species Z05 comprising amino acids 47–834 of SEQ ID NO:8.

10. The recombinant thermostable DNA polymerase enzyme of claim 2 wherein said enzyme is a mutant form of Thermus species Z05 comprising amino acids 78–834 of SEQ ID NO:8.

11. The recombinant thermostable DNA polymerase enzyme of claim 2 wherein said enzyme is a mutant form of *Thermus thermophilus* comprising amino acids 47–834 of SEQ ID NO:10.

12. The recombinant thermostable DNA polymerase enzyme of claim 2 wherein said enzyme is a mutant form of *Thermus thermophilus* comprising amino acids 78–834 of SEQ ID NO:10.

13. The recombinant thermostable DNA polymerase enzyme of claim 2 wherein said enzyme is a mutant form of *Thermosipho africanus* comprising amino acids 38–892 of SEQ ID NO:12.

* * * * *